US012233242B2

(12) United States Patent
O'Connell et al.

(10) Patent No.: US 12,233,242 B2
(45) Date of Patent: Feb. 25, 2025

(54) SYSTEMS AND METHODS FOR INTERACTIVE EXERCISE THERAPY

(71) Applicant: Fitscript LLC, New Haven, CT (US)

(72) Inventors: Charles O'Connell, New Haven, CT (US); Keivon Jones, Hamden, CT (US); Matt Walton, New Haven, CT (US); Andrew Wood, Bridgeport, CT (US)

(73) Assignee: FITSCRIPT LLC, New Haven, CT (US)

( * ) Notice: Subject to any disclaimer, the term of this patent is extended or adjusted under 35 U.S.C. 154(b) by 155 days.

(21) Appl. No.: 18/184,361

(22) Filed: Mar. 15, 2023

(65) Prior Publication Data
US 2023/0338655 A1   Oct. 26, 2023

Related U.S. Application Data

(63) Continuation of application No. 16/408,044, filed on May 9, 2019, now abandoned, which is a continuation
(Continued)

(51) Int. Cl.
*A61B 5/0205* (2006.01)
*A61B 5/00* (2006.01)
(Continued)

(52) U.S. Cl.
CPC ......... *A61M 5/1723* (2013.01); *A61B 5/0205* (2013.01); *A61B 5/1128* (2013.01);
(Continued)

(58) Field of Classification Search
None
See application file for complete search history.

(56) References Cited

U.S. PATENT DOCUMENTS

| 5,474,552 A | 12/1995 | Palti |
| 5,591,104 A | 1/1997 | Andrus et al. |

(Continued)

FOREIGN PATENT DOCUMENTS

| WO | WO-2004084976 A1 | 10/2004 |
| WO | WO-2006105146 A2 | 10/2006 |

(Continued)

OTHER PUBLICATIONS

Berg, E. The Artificial Pancreas Aces New Tests. "Bionic" volunteers venture into the real world of ice cream and red wine. Diabetes Forecast: The Healthy Living Magazine, Mar. 2014. Accessed online Nov. 3, 2015. http://www.diabetesforecast.org/2014/mar/the-artificial-pancreas-aces.html.
(Continued)

*Primary Examiner* — Kesha Frisby
(74) *Attorney, Agent, or Firm* — Wilson Sonsini Goodrich & Rosati

(57) ABSTRACT

Safe and effective exercise poses a specific set of challenges for subjects diagnosed with diabetes. These challenges include the coordination of exercise with blood glucose monitoring and insulin administration. Failure to coordinate these factors effectively can lead to various pathologies related to aberrant blood glucose levels. Presented herein are methods, systems, algorithms, computer program products, web portals, real-time live instruction, and computer-executable code for exercise guidance and instruction specific to diabetes relief and management. The systems as disclosed herein can help ameliorate, slow, or reduce a likelihood of developing a diabetic condition.

21 Claims, 18 Drawing Sheets

Related U.S. Application Data of application No. 16/241,936, filed on Jan. 7, 2019, now abandoned.

(60) Provisional application No. 62/614,782, filed on Jan. 8, 2018.

(51) Int. Cl.
    | | |
    |---|---|
    | A61B 5/11 | (2006.01) |
    | A61B 5/145 | (2006.01) |
    | A61M 5/172 | (2006.01) |
    | A63B 24/00 | (2006.01) |
    | G06Q 30/0251 | (2023.01) |
    | G16H 20/30 | (2018.01) |
    | A61B 5/024 | (2006.01) |

(52) U.S. Cl.
    CPC ........ *A61B 5/14532* (2013.01); *A61B 5/4836* (2013.01); *A61B 5/4839* (2013.01); *A61B 5/7275* (2013.01); *A61B 5/743* (2013.01); *A63B 24/0062* (2013.01); *G06Q 30/0251* (2013.01); *G16H 20/30* (2018.01); *A61B 5/0002* (2013.01); *A61B 5/024* (2013.01); *A61B 2503/10* (2013.01); *A61M 2205/3553* (2013.01); *A61M 2205/3584* (2013.01); *A61M 2205/50* (2013.01); *A61M 2230/201* (2013.01); *A61M 2230/63* (2013.01); *A63B 2024/0081* (2013.01); *A63B 2230/04* (2013.01); *A63B 2230/202* (2013.01)

(56) References Cited

U.S. PATENT DOCUMENTS

| | | | |
|---|---|---|---|
| 6,039,688 | A | 3/2000 | Douglas et al. |
| 7,931,563 | B2 | 4/2011 | Shaw et al. |
| 7,949,382 | B2 | 5/2011 | Jina |
| 8,135,624 | B1 | 3/2012 | Ramalingam et al. |
| 8,585,593 | B2 | 11/2013 | Kovatchev et al. |
| 8,725,534 | B2 | 5/2014 | Settimi |
| 9,861,310 | B2 | 1/2018 | O'Connell |
| 10,548,525 | B2 | 2/2020 | O'Connell |
| 2004/0054263 | A1 | 3/2004 | Moerman et al. |
| 2006/0219576 | A1 | 10/2006 | Jina |
| 2007/0093750 | A1 | 4/2007 | Jan et al. |
| 2007/0113725 | A1 | 5/2007 | Oliver et al. |
| 2007/0122780 | A1 | 5/2007 | Moon et al. |
| 2008/0139907 | A1 | 6/2008 | Rao et al. |
| 2008/0262469 | A1 | 10/2008 | Brister et al. |
| 2009/0089098 | A1 | 4/2009 | Schoenberg |
| 2009/0112694 | A1 | 4/2009 | Jung et al. |
| 2010/0184565 | A1 | 7/2010 | Avellino |
| 2010/0250285 | A1 | 9/2010 | Shelton |
| 2010/0286601 | A1 | 11/2010 | Yodfat et al. |
| 2010/0331652 | A1 | 12/2010 | Groll et al. |
| 2011/0077956 | A1 | 3/2011 | Kapu et al. |
| 2011/0184342 | A1 | 7/2011 | Pesach et al. |
| 2012/0226259 | A1 | 9/2012 | Yodfat et al. |
| 2012/0254907 | A1 | 10/2012 | Serdiuk |
| 2012/0302990 | A1 | 11/2012 | de Paula |
| 2013/0097715 | A1 | 4/2013 | Fourman |
| 2013/0165901 | A1 | 6/2013 | Ruchti et al. |
| 2013/0275230 | A1 | 10/2013 | Sawyer et al. |
| 2014/0052722 | A1 | 2/2014 | Bertsimas et al. |
| 2014/0129330 | A1 | 5/2014 | Fuller |
| 2017/0216671 | A1 | 8/2017 | Wisbey et al. |
| 2017/0229149 | A1 | 8/2017 | Rothschild et al. |

FOREIGN PATENT DOCUMENTS

| | | |
|---|---|---|
| WO | WO-2015135066 A1 | 9/2015 |
| WO | WO-2016061550 A1 | 4/2016 |

OTHER PUBLICATIONS

Breton et al., Adding Heart Rate Signal to a Control-to-Range Artificial Pancreas System Improves the Protection Against Hypoglycemia During Exercise in Type 1 Diabetes, Diabetes Technology & Therapeutics, 2014; vol. 16(8), pp. 506-511.

Castle, et al. Novel Use of Glucagon in a Closed-Loop System for Prevention of Hypoglycemia in Type 1 Diabetes. Diabetes Care, Jun. 2010, vol. 33, No. 6, pp. 1282-1287.

Charlie O'Connell Youtube Video with Transcript. Accessed online Nov. 3, 2015. https://www.youtube.com/watch?v=z70-5j_IgFA.

D-Fight! Total Body Exercise for Diabetes DVD Set with Transcript. Accessed Nov. 3, 2015.

DLife TV Episode—Exercising with a Disability Youtube Video with Transcript. Accessed online Nov. 3, 2015. https://www.youtube.com/watch?v=I8PffGRgMvg.

Figueira et al., Aerobic and Combined Exercise Sessions Reduce Glucose Variability in Type 2 Diabetes: Crossover Randomized Trial, Mar. 2013, PLOS ONE, vol. 8, Issue 3, e57733,pp. 1-10.

Fitscript Website: Fitness Prescriptions for Diabetes Prevention and Management. Accessed online Nov. 3, 2015. http://www.fitscript.com/.

Glucosezone: Youtube. Accessed online Nov. 3, 2015. https://www.youtube.com/user/GLUCOSEZONE.

International Search Report and Written Opinion dated Jan. 8, 2016 for International PCT Application No. PCT/US2015/056089.

International Search Report and Written Opinion dated Apr. 23, 2019 for International PCT Application No. PCT/US2019/012579.

Jacobs, et al. Incorporating an Exercise Detection, Grading, and Hormone Dosing Algorithm Into the Artificial Pancreas Using Accelerometry and Heart Rate. J Diabetes Sci Technol Oct. 5, 2015.

Kapitza et al., Continuous Glucose Monitoring during Exercise in Patients with Type 1 Diabetes on Continuous Subcutaneous Insulin Infusion, Jan. 2010; vol. 4(1), pp. 123-131.

Modules and Elements: Controller, CoreMD and Pancreum Wedges. Pancreum: The Wearable Artificial Pancreas Company Website. Accessed online Nov. 3, 2015. http://pancreum.com/modules-bionic-artificial-pancreas.html.

National Exercise Guidelines for Adults. dLife Website. Accessed online Nov. 3, 2015. http://www.dlife.com/diabetes-food-and-fitness/diabetes_and_exercise/exercise_guidelines?utm_source=dLife&utm_medium=dLifeTV&utm_content=TVThrow&utm_campaign=exerciseguide.

Scheiner, G. Getting Down to Basals. Diabetes Self-Management Website. Published Jul. 24, 2006. Accessed online Nov. 3, 2015. http://www.diabetesselfmanagement.com/managing-diabetes/treatment-approaches/getting-down-to-basals/.

Stenerson, et al., The Impact of Accelerometer Use in Exercise-Associated Hypoglycemia Prevention in Type I Diabetes, Journal of Diabetes Science and Technology, 2015, vol. 9(1) pp. 80-85.

Weinstock, R. Closing the Loop: Another Step Forward. Diabetes Care, Sep. 2011, vol. 34, No. 9, pp. 2136-2137.

Main + Program Buttons (Continue)

SYSTEMS AND METHODS FOR INTERACTIVE EXERCISE THERAPY

CROSS REFERENCE

This Application is a Continuation Application of U.S. Ser. No. 16/408,044 filed May 9, 2019, which is a Continuation Application of U.S. application Ser. No. 16/241,936 filed Jan. 7, 2019, which claims the benefit of U.S. Provisional Application No. 62/614,782 filed Jan. 8, 2018, each of which is incorporated herein by reference in its entirety.

BACKGROUND OF THE INVENTION

Safe and effective exercise poses a specific set of challenges for subjects diagnosed with diabetes. These challenges include the coordination of exercise with glucose monitoring and administration of medications. Failure to coordinate these factors effectively can lead to various pathologies, including headache, seizure, faintness, withdrawal, depression, and hypoglycemia.

INCORPORATION BY REFERENCE

Each patent, publication, and non-patent literature cited in the application is hereby incorporated by reference in its entirety as if each was incorporated by reference individually.

SUMMARY OF THE INVENTION

In some embodiments, the invention provides a system comprising: a media device configured to present: a) an instructional exercise electronic communication based on a biometric measurement detected in a subject by a biometric device; and b) an advertisement electronic communication based on the biometric measurement detected in the subject.

In some embodiments, the invention provides a method comprising: a) presenting by a media device to a subject an instructional exercise electronic communication that provides instruction for physical exercise based on a biometric measurement detected in the subject by a biometric device; and b) presenting by the media device to the subject an advertisement electronic communication that provides an advertisement based on the biometric measurement detected in the subject.

In some embodiments, the invention provides a computer program product comprising a non-transitory computer-readable medium having computer-executable code encoded therein, the computer-executable code adapted to be executed to implement a method of advertising to a subject, the method comprising: a) processing an advertisement system, wherein the advertisement system comprises: i) an instructional exercise communication module; ii) an advertisement communication module; and iii) an output module; b) generating by the instructional exercise communication module an instructional exercise communication based on a reading of a biometric measurement detected in the subject by a biometric device; c) generating by the advertisement communication module an advertisement based on the reading of the biometric measurement detected in the subject; d) communicating by the output module the instructional exercise communication to an output media device; and e) communicating by the output module the advertisement to the output media device.

In some embodiments, the invention provides a method comprising: a) reviewing by a user from a media device an instructional exercise electronic communication; b) performing by the user an exercise suggested by the instructional exercise electronic communication; and c) receiving by the user from the media device an advertisement electronic communication that provides an advertisement based on a biometric measurement detected in the user by a biometric device.

In some embodiments, the invention provides a method comprising: a) performing by a user an exercise; b) receiving by the user from a media device an instructional exercise electronic communication based on a biometric measurement detected in the user by a biometric device; and c) receiving by the user from the media device an advertisement electronic communication that provides an advertisement based on the biometric measurement detected in the user by the biometric device.

In some embodiments, the invention provides a system comprising: a) a heart rate monitoring device configured to detect a heart rate in a subject; and b) a media device configured to present an advertisement electronic communication based on the heart rate detected in the subject by the heart rate monitoring device, wherein the heart rate monitoring device is configured to transmit to the media device a reading of the heart rate in the subject, wherein the media device is configured to present the advertisement electronic communication upon determination that the heart rate in the subject detected by the heart rate monitoring device is in a zone from 40% to 100% of a maximum heart rate in the subject.

In some embodiments, the invention provides a method comprising presenting to a subject by a media device an advertisement electronic communication that provides an advertisement based on a heart rate detected in the subject by a heart rate monitoring device, wherein the subject is performing an exercise in a zone from 40% to 100% of a maximum heart rate in the subject.

In some embodiments, the invention provides a computer program product comprising a non-transitory computer-readable medium having computer-executable code encoded therein, the computer-executable code adapted to be executed to implement a method of advertising to a subject, the method comprising: a) processing an advertisement system, wherein the advertisement system comprises: i) a biometric data receiving module; ii) an advertisement communication module; and iii) an output module; b) receiving by the biometric data receiving module a reading of a heart rate detected in the subject by a heart rate monitoring device and determining that the heart rate detected in the subject is from 40% to 100% of a maximum heart rate in the subject; c) generating by the advertisement communication module an advertisement based on the reading of the heart rate detected in the subject; and d) communicating by the output module the advertisement to an output media device.

In some embodiments, the invention provides a method comprising: a) reviewing by a user from a media device an instructional exercise electronic communication; b) performing by the user an exercise suggested by the instructional exercise electronic communication; and c) receiving by the user from the media device an advertisement electronic communication that provides an advertisement upon determination that a heart rate in the user detected by a heart rate monitoring device is in a zone from 40% to 100% of a maximum heart rate in the user.

In some embodiments, the invention provides a system comprising: a media device configured to present: a) an instructional exercise electronic communication based on a biometric measurement detected in a subject by a biometric device; and b) a clinical trial electronic communication based on the biometric measurement detected in the subject.

In some embodiments, the invention provides a method comprising: a) presenting by a media device to a subject an instructional exercise electronic communication based on a biometric measurement detected in the subject by a biometric device; and b) determining eligibility of the subject in a clinical trial based on the biometric measurement detected in the subject.

In some embodiments, the invention provides a computer program product comprising a non-transitory computer-readable medium having computer-executable code encoded therein, the computer-executable code adapted to be executed to implement a method of recruiting a subject in a clinical trial, the method comprising: a) processing a clinical trial recruitment system, wherein the clinical trial recruitment system comprises: i) an instructional exercise communication module; ii) an clinical trial communication module; and iii) an output module; b) generating by the instructional exercise communication module an instructional exercise communication based on a reading of a biometric measurement detected in the subject by a biometric device; c) generating by the clinical trial communication module a clinical trial electronic communication based on the reading of the biometric measurement in the subject; d) communicating by the output module the instructional exercise communication to an output media device; and e) communicating by the output module the clinical trial electronic communication to the output media device.

In some embodiments, the invention provides a method comprising: a) receiving by the user from a media device an instructional exercise electronic communication; b) performing by the user an exercise provided by the instructional exercise electronic communication; and c) receiving by the user from the media device a clinical trial communication that provides a notification of a clinical trial based on a biometric measurement in the user by a biometric device.

In some embodiments, the invention provides a system comprising: a media device configured to present: a) an instructional exercise electronic communication based on a biometric measurement detected in a subject by a biometric device; and b) a non-exercise health recommendation to the subject based on the biometric measurement detected in the subject.

In some embodiments, the invention provides a method comprising: a) receiving by a user from a media device an instructional exercise electronic communication; b) performing by the user an exercise provided by the instructional exercise electronic communication; and c) receiving by the user from the media device a non-exercise health recommendation based on a biometric measurement detected in a user by a biometric device.

DETAILED DESCRIPTION OF THE INVENTION

The disclosure provides methods, systems, algorithms, computer programs, kits, devices, and computer-executable code for exercise guidance and instruction specific to diabetes relief and management, and the slowing or reducing a likelihood of developing a diabetic condition. The methods, systems, algorithms, computer programs, kits, devices, and computer-executable code are based in part on correlations and interrelationships among variables associated with glucose and insulin levels during exercise. The systems include real-time access to online exercise portals and communities. The portals can provide exercise instruction and counseling and rescue from diabetic episodes that occur during exercise. The portals also assist in avoiding such episodes. Live, interactive online exercise is possible among a number of remote users.

Figure 13:
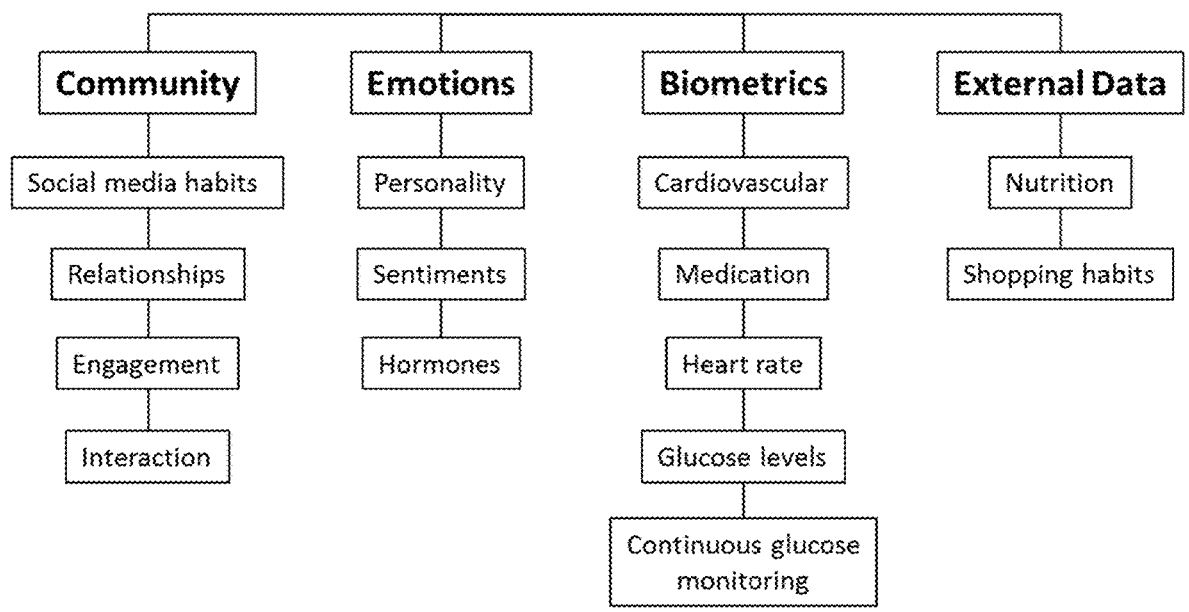
FIG. 13 illustrates a schematic of various factors associated with diabetes management.

Effective diabetes management requires more than simply modulation of blood glucose levels. Challenges related to diabetes management can vary based on, for example, diabetes type, genetics, diabetes comorbidities, lifestyle habits, fitness level, and personality, which differ among individuals. Thus, diabetes management systems are more effective when tailored to the specific needs of an individual. The present disclosure provides dynamic and comprehensive systems and methods of diagnosing and managing diabetes in a subject by accounting for a variety of physiological and psychological factors that contribute to the progression of diabetes. The disclosed systems and methods can guide diabetics to adhere to behavioral and long-term lifestyle habits for effective diabetes management. As shown in FIG. 13, physiological and psychological factors include, for example, emotional states, community interactions, external environmental influences, biometrics, nutrition, and medical interventions. Lifestyle factors can further include, for example, sleeping habits and psychological state.

The present disclosure further provides intelligent and relevant real-time advertisement content to users based on the various physiological and psychological factors.

Diabetes

In some embodiments, a subject using a method, system, algorithm, computer program, kit, device, or computer-executable code of the disclosure is diagnosed with diabetes. Non-limiting examples of diabetes include diabetes mellitus, type-1 diabetes, type-2 diabetes, prediabetes, gestational diabetes, latent autoimmune diabetes of adults, congenital diabetes, cystic fibrosis-related diabetes, steroid diabetes, and monogenic diabetes.

Diabetes is a group of metabolic diseases in which high blood sugar levels persist over a prolonged period. Symptoms of high blood sugar include frequent urination, increased thirst, and increased hunger. If left untreated, diabetes can cause many complications. Acute complications include diabetic ketoacidosis and non-ketotic hyperosmolar coma. Chronic complications include cardiovascular disease, stroke, chronic kidney failure, foot ulcers, and damage to the eyes.

Diabetes is caused by either failure of the pancreas to produce sufficient insulin, or the cells of the body not responding properly to the insulin produced. Type-1 diabetes results from the inability of the pancreas to produce enough insulin. Type-2 diabetes begins with insulin resistance, a condition in which cells and tissues fail to respond to insulin properly. As the disease progresses, a lack of insulin can also develop. A primary cause is excessive body weight and insufficient exercise. Gestational diabetes is the third main form, and occurs when pregnant women without a previous history of diabetes develop a high blood sugar level.

Non-limiting examples of symptoms of diabetes include weight loss, increased urination or polyuria, increased thirst or polydipsia, increased hunger or polyphagia, blurry vision, headache, fatigue, slow healing of cuts, itchy skin, changes in the shape of the lens of the eye, and skin rashes or dermadromes. Low blood sugar or hypoglycemia is prevalent in subjects with type-1 and type-2 diabetes. Non-limiting examples of hypoglycemic symptoms include feelings of unease, sweating, trembling, increased appetite, confusion, changes in behavior, seizures, unconsciousness, and permanent brain damage. Subjects, such as those diagnosed with type-1 diabetes, can also experience episodes of diabetic ketoacidosis, a metabolic disturbance characterized by nausea, vomiting and abdominal pain, the scent of acetone on the breath, deep breathing known as Kussmaul breathing, and in severe cases, reduced consciousness. Subjects, such as those diagnosed with type-2 diabetes, can also experience a hyperosmolar non-ketotic state, which is the result of dehydration.

Non-limiting examples of long-term complications due to diabetes include damage to blood vessels, cardiovascular disease, coronary artery disease, stroke, peripheral vascular disease, and damage to blood vessels of the eyes, kidneys, and nerves. Damage to blood vessels of the eyes, also known as diabetic retinopathy, can result in gradual vision loss and blindness. Damage to blood vessels of the kidneys, known as diabetic nephropathy, can result in tissue scarring, urine protein loss, and eventually chronic kidney disease. Damage to blood vessels of the nerves, known as diabetic neuropathy, can result in numbness, tingling, pain, altered pain sensation, leading to damage of the skin, and painful muscle wasting and weakness. Diabetes-related foot problems, such as diabetic foot ulcers, can occur and result in amputation.

Non-limiting examples of possible risks that can occur during exercise include hypoglycemia, hyperglycemia, insulin shock, diabetic shock, low heart rate, high heart rate, fainting, unconsciousness, and death.

Co-Medications of Insulin and Diabetes Comorbidities

In some embodiments, the methods, systems, algorithms, computer programs, kits, devices, and computer-executable code include administration of an insulin. Non-limiting examples of insulins include regular insulin, insulin glulisine, insulin lispro, insulin aspart, insulin lispro protamine, insulin aspart protamine, insulin neutral protamine Hagedorn (NPH), insulin glargine, and insulin detemir. In some embodiments, the insulin is a mixture of insulin. Non-limiting examples of mixtures of insulin include about 30% regular insulin and about 70% insulin NPH; about 50% insulin lispro and about 50% insulin lispro protamine; about 25% insulin lispro and about 75% insulin lispro protamine; and about 30% insulin aspart and about 70% insulin aspart protamine.

In some embodiments, the methods, systems, algorithms, computer programs, kits, devices, and computer-executable code provided herein can incorporate information relating to a medication taken by the subject that can alter how an exercise instruction of the disclosure modulates blood sugar. Non-limiting examples of medications include anti-diabetic medications, blood pressure medications, anti-inflammatory medications, acid reflux medications, and anti-arthritic medications. Non-limiting examples of anti-diabetic medications include biguanides, sulfonylureas, meglitinides, thiazolidinediones, dipeptidyl peptidase-4 (DPP-4) inhibitors, glucagon-like peptide-1 receptor (GLP-1) agonists, sodium glucose co-transporter 2 (SGLT2) inhibitors, a-glucosidase inhibitors, metformin, phenformin, buformin, rosiglitazone, pioglitazone, troglitazone, canagliflozin, dapagliflozin, miglitol, acarbose, voglibose, repaglinide, nateglinide, gliquidone, glimepiride, gliclazide, glipizide, sitagliptin, liraglutide, dulaglutide, and canagliflozin.

In some embodiments, the present invention includes systems and methods for reducing an amount or dosage of a medication taken by the subject based on user adherence to an exercise guidance provided herein. Non-limiting examples of medications include anti-diabetic drugs, blood pressure drugs, anti-inflammatory drugs, acid reflux drugs, and anti-arthritic drugs. Non-limiting examples of anti-diabetic drugs include insulins, DPP-4 inhibitors, GLP-1 agonists, SGLT2 inhibitors, α-glucosidase inhibitors, metformin, phenformin, buformin, rosiglitazone, pioglitazone, troglitazone, canagliflozin, dapagliflozin, miglitol, acarbose, voglibose, repaglinide, nateglinide, gliquidone, glimepiride, gliclazide, glipizide, sitagliptin, liraglutide, dulaglutide, and canagliflozin.

In some embodiments, a subject of the disclosure engaging in exercise exhibits comorbidities that, along with diabetes, can affect how exercise modulates blood glucose. Non-limiting examples of comorbidities include heart disease, respiratory disease, hypertension, kidney problems, liver problems, strokes, and joint disease.

Non-limiting examples of suitable variables include established safety guidelines for glucose levels before during and after exercise; time of day and duration of activity; heart rate level and perceived exertion level; muscle fiber recruitment and activity performed; presence of insulin and medication; and food consumed.

Each variable can have a unique and distinguishable impact on glucose levels during exercise. In some embodiments, based on different implementations of combinations of the variables, the disclosure can provide exercise recommendations and instruction targeting specific and desired diabetes metrics outcomes. Non-limiting examples of such outcomes include A1C reduction; increase in insulin sensitivity; decrease in insulin resistance; increased fat metabolism and weight loss; real-time reduction of blood glucose levels; real-time elevation of blood glucose levels; and reduction of anti-diabetic medication dependence. In some embodiments, the disclosure can provide exercise recommendations and instruction targeting specific and desired cardiovascular and pulmonary outcomes. Non-limiting examples of such outcomes include increased muscle tone; increased cardiac stress resistance; and increased lung function.

Exercise Guidance Based Upon Target Heart Rates

In some embodiments, the methods of the disclosure are adaptable and are designed to achieve specific outcomes related to type-1 diabetes, such as reduced insulin dependence. In some embodiments, the methods of the disclosure are adaptable and are designed to achieve specific outcomes related to type-2 diabetes. Non-limiting examples of such outcomes include A1C reduction; increased fat metabolism; increased weight loss; real-time decrease of blood glucose levels; increase in insulin sensitivity; and decrease in insulin resistance.

In some embodiments, a collection of exercises is preselected to achieve the desired diabetes metrics listed above. Each suggested exercise is pre-selected to meet at least one of the following criteria: be performed in a heart rate zone from 50% to 100% of a maximum heart rate and correlating exertion level that does not cross the anaerobic threshold and does not stimulate the raising of glucose levels; utilizes either aerobic glycolysis or fat oxidization as the metabolic pathway for the provision of energy; causes the systematic depletion of glycogen stores within specific skeletal muscle without stimulating a glycolytic response from the liver, such as release of stored glycogen into the blood stream resulting in a rise in glucose levels, resulting in an increase in insulin sensitivity and decrease in insulin resistance; and be performed for an amount of time that stimulates the systematic depletion of glycogen stores within selected skeletal musculature.

Based on the subject's level of physical fitness, severity of diabetic symptoms, and exercise preferences, the subject can choose a target heart rate for an exercise session. The target heart rate can be determined as a percentage of the subject's maximum heart rate. The heart rate can also be chosen based on the level of physical exertion that the subject chooses to experience. Once the subject has chosen a target heart rate, the subject can plan for the glucose and insulin levels that are suitable for the target heart zone. The subject can thus establish target ranges or target values for various biometric parameters, such as heart rate, glucose level, and insulin level. The subject can also establish rates of administration for insulin and glucagon.

For example, a subject can find that exercise that promotes a heart rate of from 50% to 60% of the subject's maximum heart rate is easy and comfortable. This heart rate can cause a small decrease in glucose levels, as most of the subject's energy consumed is carbohydrate. The subject should maintain a level of insulin that is appropriate for the subject's carbohydrate consumption.

A subject can find that exercise that promotes a heart rate of from 60% to 70% of the subject's maximum heart rate is challenging and beneficial. This heart rate functions as a fat-burning zone. Significant decreases in glucose levels are possible. The subject should maintain a level of insulin that is appropriate for the subject's carbohydrate consumption.

A subject can find that exercise that promotes a heart rate of from 70% to 80% of the subject's maximum heart rate is hard. In this zone, the subject's energy consumption is approximately half carbohydrate and half fat. A subject can experience a risk of hypoglycemia, and a significant drop in blood glucose levels is possible. A subject can reduce insulin levels to aid in avoiding hypoglycemia.

A subject can find that exercise that promotes a heart rate of from 80% to 90% of the subject's maximum heart rate is very hard. The subject's energy expenditure is approximately 85% carbohydrate, 15% fat, and a small amount of protein. The subject's glucose levels can fluctuate, and the ability to store and produce glycogen can vary significantly based on physical fitness.

A subject can find that exercise that promotes a heart rate of from 90% to 100% of the subject's maximum heart rate is the subject's maximum possible effort. The subject's energy expenditure is approximately 90% carbohydrate, 10% fat, and a small amount of protein. The subject's glucose levels can rise, possibly to an unsafe level, especially if the subject simultaneously consumes a food containing a high carbohydrate content.

The maximum heart rate of the subject can be estimated in several ways. In some embodiments, the maximum heart rate is estimated by the following:

Maximum heart rate(in beats per minute[bpm])
=220−(age of the subject[age]);

In some embodiments, the maximum heart rate is estimated by the following:

Maximum heart rate(in bpm)=208−(0.7×age);

In some embodiments, the maximum heart rate is estimated by the following:

Maximum heart rate(in bpm)=207−(0.7×age);

In some embodiments, the maximum heart rate is estimated by a treadmill test. The treadmill test entails a subject running on a treadmill while connected to heart rate monitors and blood pressure monitors. At various periods of time, the treadmill accelerates and the incline rises, until the subject reaches the maximum sustained effort. The measured heart rate of the subject at the maximum sustained effort is the maximum heart rate of the subject.

Rather than choosing a target heart rate, a subject can also choose a desired exercise to perform, and input the desired exercise into any system herein. Based on the subject's choice of exercise, and other factors, a system of the invention can approve, disapprove, or modify the desired exercise. A system herein can also modulate the subject's insulin administration rate or glucagon administration rate based on choice of exercise; heart rate, for example, real time heart rate as detected during exercise; glucose level, for example, real time blood glucose level as detected during exercise; or electronically-stored records of the subject's past exercise performance and diabetes risk factors, such as nutrition, time of day, and general level of physical fitness.

In some embodiments, prior to the subject being in a state of physical exercise, while the subject is in a state of physical rest, a heart rate of the subject at a resting level is from about 10% to about 50% of the maximum heart rate of the subject. In some embodiments, the heart rate of the subject at the resting level is from about 10% to about 15%, from about 15% to about 20%, from about 20% to about 25%, from about 25% to about 30%, from about 30% to about 35%, from about 35% to about 40%, from about 40% to about 45%, or from about 45% to about 50% of the maximum heart rate of the subject.

In some embodiments, subsequent to the subject being in the state of physical rest, while the subject is in the state of physical exercise, the heart rate of the subject is elevated to an active level that is from about 50% to about 100% of the maximum heart rate of the subject. In some embodiments, the heart rate of the subject is elevated to the active level that is from about 50% to about 55%, from about 55% to about 60%, from about 60% to about 65%, from about 65% to about 70%, from about 70% to about 75%, from about 75% to about 80%, from about 80% to about 85%, from about 85% to about 90%, from about 90% to about 95%, or from about 95% to about 100% of the maximum heart rate of the subject.

A subject can also approximate heart rate based on comparison to a physical activity. A subject can plan to exercise or perform a physical activity at a heart rate level that is comparable to the heart rate experience, for example, during walking, jogging, running, stair climbing, swimming, cycling, golfing, dancing, stretching, or playing a sport. In some embodiments, the exercise is aerobic exercise, endurance exercise, muscle resistance training, or flexibility and balance training.

In some embodiments, the subject receives or is administered a dose of a hormone at a basal rate. Non-limiting examples of hormones to be administered include insulin, glucagon, adrenaline, and corticosteroids, such as cortisol. In some embodiments, the basal rate of the dose of hormone is from about 2 units per day (U/d) to about 50 U/d. In some embodiments, the basal rate of the dose of hormone is from about 2 U/d to about 20 U/d, from about 5 U/d to about 50 U/d, from about 5 U/d to about 40 U/d, or from about 10 U/d to about 50 U/d. In some embodiments, the basal rate of the dose of hormone is from about 2 U/d to about 3 U/d, from about 3 U/d to about 4 U/d, from about 4 U/d to about 5 U/d, from about 5 U/d to about 6 U/d, from about 6 U/d to about 7 U/d, from about 7 U/d to about 8 U/d, from about 8 U/d to about 9 U/d, from about 9 U/d to about 10 U/d, from about 10 U/d to about 11 U/d, from about 11 U/d to about 12 U/d, from about 12 U/d to about 13 U/d, from about 13 U/d to about 14 U/d, from about 14 U/d to about 15 U/d, from about 15 U/d to about 16 U/d, from about 16 U/d to about 17 U/d, from about 17 U/d to about 18 U/d, from about 18 U/d to about 19 U/d, from about 19 U/d to about 20 U/d, from about 20 U/d to about 21 U/d, from about 21 U/d to about 22 U/d, from about 22 U/d to about 23 U/d, from about 23 U/d to about 24 U/d, from about 24 U/d to about 25 U/d, from about 25 U/d to about 26 U/d, from about 26 U/d to about 27 U/d, from about 27 U/d to about 28 U/d, from about 28 U/d to about 29 U/d, from about 29 U/d to about 30 U/d, from about 30 U/d to about 31 U/d, from about 31 U/d to about 32 U/d, from about 32 U/d to about 33 U/d, from about 33 U/d to about 34 U/d, from about 34 U/d to about 35 U/d, from about 35 U/d to about 36 U/d, from about 36 U/d to about 37 U/d, from about 37 U/d to about 38 U/d, from about 38 U/d to about 39 U/d, from about 39 U/d to about 40 U/d, from about 40 U/d to about 41 U/d, from about 41 U/d to about 42 U/d, from about 42 U/d to about 43 U/d, from about 43 U/d to about 44 U/d, from about 44 U/d to about 45 U/d, from about 45 U/d to about 46 U/d, from about 46 U/d to about 47 U/d, from about 47 U/d to about 48 U/d, from about 48 U/d to about 49 U/d, or from about 49 U/d to about 50 U/d.

In some embodiments, the basal rate of the dose of hormone is from about 0.05 units per hour (U/h) to about 2.2 U/h. In some embodiments, the basal rate of the dose of hormone is from about 0.05 U/h to about 0.9 U/h, from about 0.2 U/h to about 2.2 U/h, from about 0.2 U/h to about 1.8 U/h, or from about 0.3 U/h to about 2.2 U/h. In some embodiments, the basal rate of the dose of hormone is from about 0.05 U/h to about 0.1 U/h, from about 0.1 U/h to about 0.15 U/h, from about 0.15 U/h to about 0.2 U/h, from about 0.2 U/h to about 0.25 U/h, from about 0.25 U/h to about 0.3 U/h, from about 0.3 U/h to about 0.35 U/h, from about 0.35 U/h to about 0.4 U/h, from about 0.4 U/h to about 0.45 U/h, from about 0.45 U/h to about 0.5 U/h, from about 0.5 U/h to about 0.55 U/h, from about 0.55 U/h to about 0.6 U/h, from about 0.6 U/h to about 0.65 U/h, from about 0.65 U/h to about 0.7 U/h, from about 0.7 U/h to about 0.75 U/h, from about 0.75 U/h to about 0.8 U/h, from about 0.8 U/h to about 0.85 U/h, from about 0.85 U/h to about 0.9 U/h, from about 0.9 U/h to about 0.95 U/h, from about 0.95 U/h to about 1 U/h, from about 1 U/h to about 1.05 U/h, from about 1.05 U/h to about 1.1 U/h, from about 1.1 U/h to about 1.15 U/h, from about 1.15 U/h to about 1.2 U/h, from about 1.2 U/h to about 1.25 U/h, from about 1.25 U/h to about 1.3 U/h, from about 1.3 U/h to about 1.35 U/h, from about 1.35 U/h to about 1.4 U/h, from about 1.4 U/h to about 1.45 U/h, from about 1.45 U/h to about 1.5 U/h, from about 1.5 U/h to about 1.55 U/h, from about 1.55 U/h to about 1.6 U/h, from about 1.6 U/h to about 1.65 U/h, from about 1.65 U/h to about 1.7 U/h, from about 1.7 U/h to about 1.75 U/h, from about 1.75 U/h to about 1.8 U/h, from about 1.8 U/h to about 1.85 U/h, from about 1.85 U/h to about 1.9 U/h, from about 1.9 U/h to about 1.95 U/h, from about 1.95 U/h to about 2 U/h, from about 2 U/h to about 2.05 U/h, from about 2.05 U/h to about 2.1 U/h, from about 2.1 U/h to about 2.15 U/h, or from about 2.15 U/h to about 2.2 U/h.

In some embodiments, the subject receives or is administered the dose of hormone at an adjusted rate. The adjusted rate of the dose of hormone is determined relative to the basal rate of the dose of hormone. In some embodiments, the adjusted rate of the dose of hormone is about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.9%, about 101%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200%, about 250%, about 300%, about 350%, about 400%, about 450%, about 500%, about 550%, about 600%, about 650%, about 700%, about 750%, about 800%, about 850%, about 900%, about 950%, or about 1000% of the basal rate of the dose of hormone.

In some embodiments, the adjusted rate of the dose of hormone is from about 0.1% to about 0.5%, from about 0.5% to about 1%, from about 1% to about 5%, from about 5% to about 10 from about 10% to about 15%, from about 15% to about 20%, from about 20% to about 25%, from about 25% to about 30%, from about 30% to about 35%, from about 35% to about 40%, from about 40% to about 45%, from about 45% to about 50%, from about 50% to about 55%, from about 55% to about 60%, from about 60% to about 65%, from about 65% to about 70%, from about 70% to about 75%, from about 75% to about 80%, from about 80% to about 85%, from about 85% to about 90%, from about 90% to about 91%, from about 91% to about 92%, from about 92% to about 93%, from about 93% to about 94%, from about 94% to about 95%, from about 95% to about 96%, from about 96% to about 97%, from about 97% to about 98%, from about 98% to about 99%, from about 99% to about 99.5%, from about 99.5% to about 99.9%, from about 101% to about 105%, from about 105% to about 110%, from about 110% to about 115%, from about 115% to about 120%, from about 120% to about 125%, from about 125% to about 130%, from about 130% to about 135%, from about 135% to about 140%, from about 140% to about 145%, from about 145% to about 150%, from about 150% to about 155%, from about 155% to about 160%, from about 160% to about 165%, from about 165% to about 170%, from about 170% to about 175%, from about 175% to about 180%, from about 180% to about 185%, from about 185% to about 190%, from about 190% to about 195%, from about 195% to about 200%, from about 200% to about 250%, from about 250% to about 300%, from about 300% to about 350%, from about 350% to about 400%, from about 400% to about 450%, from about 450% to about 500%, from about 500% to about 550%, from about 550% to about 600%, from about 600% to about 650%, from about 650% to about 700%, from about 700% to about 750%, from about 750% to about 800%, from about 800% to about 850%, from about 850% to about 900%, from about 900% to about 950%, or from about 950% to about 1000% of the basal rate of the dose of hormone.

In some embodiments, the adjusted rate of the dose of insulin is about 15% of the basal rate of the dose of insulin, and the heart rate of the subject is elevated to an active level that is from about 50% to about 60% of the maximum heart rate of the subject. In some embodiments, the adjusted rate of the dose of insulin is about 15% of the basal rate of the dose of insulin, and the heart rate of the subject is elevated to an active level that is from about 60% to about 70% of the maximum heart rate of the subject. In some embodiments, the adjusted rate of the dose of insulin is about 50% of the basal rate of the dose of insulin, and the heart rate of the subject is elevated to an active level that is from about 70% to about 80% of the maximum heart rate of the subject. In some embodiments, the adjusted rate of the dose of insulin is about 85% of the basal rate of the dose of insulin, and the heart rate of the subject is elevated to an active level that is from about 80% to about 90% of the maximum heart rate of the subject. In some embodiments, the adjusted rate of the dose of insulin is about 90% of the basal rate of the dose of insulin, and the heart rate of the subject is elevated to an active level that is from about 90% to about 100% of the maximum heart rate of the subject.

In some embodiments, the adjusted rate of the dose of hormone is received by or administered to the subject for a time period while the heart rate of the subject is at the resting level. In some embodiments, the time period is at least about 5 minutes, at least about 10 minutes, at least about 15 minutes, at least about 20 minutes, at least about 25 minutes, at least about 30 minutes, at least about 35 minutes, at least about 40 minutes, at least about 45 minutes, at least about 50 minutes, at least about 55 minutes, at least about one hour, at least about 90 minutes, at least about two hours, at least about 150 minutes, at least about three hours, at least about four hours, at least about five hours, or at least about six hours.

In some embodiments, the time period is from about 5 minutes to about 6 hours. In some embodiments, the time period is from about 5 minutes to about 90 minutes. In some embodiments, the time period is from about 5 minutes to about 10 minutes, from about 10 minutes to about 15 minutes, from about 15 minutes to about 20 minutes, from about 20 minutes to about 25 minutes, from about 25 minutes to about 30 minutes, from about 30 minutes to about 35 minutes, from about 35 minutes to about 40 minutes, from about 40 minutes to about 45 minutes, from about 45 minutes to about 50 minutes, from about 50 minutes to about 55 minutes, from about 55 minutes to about 60 minutes, from about 60 minutes to about 65 minutes, from about 65 minutes to about 70 minutes, from about 70 minutes to about 75 minutes, from about 75 minutes to about 80 minutes, from about 80 minutes to about 85 minutes, from about 85 minutes to about 90 minutes, from about 90 minutes to about 120 minutes, from about 120 minutes to about 150 minutes, from about 150 minutes to about 180 minutes, from about 180 minutes to about 240 minutes, from about 240 minutes to about 300 minutes, or from about 300 minutes to about 360 minutes.

In some embodiments, the methods of the disclosure include measuring the glucose level of the subject during the state of physical exercise. In some embodiments, the glucose level measured during the state of physical exercise is outside of a critical glucose range. In some embodiments, the critical glucose range is from about 70 mg/dL to about 250 mg/dL. In some embodiments, the critical glucose range is from about 100 mg/dL to about 250 mg/dL. In some embodiments, the critical glucose range is from about 70 mg/dL to about 140 mg/dL. In some embodiments, the critical glucose range is from about 100 mg/dL to about 140 mg/dL. In some embodiments, the critical glucose range is from about 70 mg/dL to about 75 mg/dL, from about 75 mg/dL to about 80 mg/dL, from about 80 mg/dL to about 85 mg/dL, from about 85 mg/dL to about 90 mg/dL, from about 90 mg/dL to about 95 mg/dL, from about 95 mg/dL to about 100 mg/dL, from about 100 mg/dL to about 105 mg/dL, from about 105 mg/dL to about 110 mg/dL, from about 110 mg/dL to about 115 mg/dL, from about 115 mg/dL to about 120 mg/dL, from about 120 mg/dL to about 125 mg/dL, from about 125 mg/dL to about 130 mg/dL, from about 130 mg/dL to about 135 mg/dL, from about 135 mg/dL to about 140 mg/dL, from about 140 mg/dL to about 145 mg/dL, from about 145 mg/dL to about 150 mg/dL, from about 150 mg/dL to about 155 mg/dL, from about 155 mg/dL to about 160 mg/dL, from about 160 mg/dL to about 165 mg/dL, from about 165 mg/dL to about 170 mg/dL, from about 170 mg/dL to about 175 mg/dL, from about 175 mg/dL to about 180 mg/dL, from about 180 mg/dL to about 185 mg/dL, from about 185 mg/dL to about 190 mg/dL, from about 190 mg/dL to about 195 mg/dL, from about 195 mg/dL to about 200 mg/dL, from about 200 mg/dL to about 205 mg/dL, from about 205 mg/dL to about 210 mg/dL, from about 210 mg/dL to about 215 mg/dL, from about 215 mg/dL to about 220 mg/dL, from about 220 mg/dL to about 225 mg/dL, from about 225 mg/dL to about 230 mg/dL, from about 230 mg/dL to about 235 mg/dL, from about 235 mg/dL to about 240 mg/dL, from about 240 mg/dL to about 245 mg/dL, or from about 245 mg/dL to about 250 mg/dL.

In some embodiments, based upon a measurement of the glucose level of the subject outside of the critical glucose range, an action is performed to restore the glucose level to within the critical glucose range. In some embodiments, the glucose level is below the critical glucose range, and the action is the consumption of a carbohydrate by the subject. Non-limiting examples of carbohydrates include slow-acting carbohydrates, fast-acting carbohydrates, chewable carbohydrates, dissolvable carbohydrates, glucose carbohydrates, sucrose carbohydrates, and fructose carbohydrates. In some embodiments, the glucose level is outside the critical glucose range, and the action is the adjustment of the dose of hormone to a second adjusted rate. In some embodiments, the glucose level is outside of the critical glucose range, and the action is a second state of physical exercise.

In some embodiments, the second adjusted rate of the dose of hormone is determined relative to the adjusted rate of the dose of hormone. In some embodiments, the second adjusted rate of the dose of hormone is about 0.1%, about 0.5%, about 1%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, about 99.5%, about 99.9%, about 101%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200%, about 250%, about 300%, about 350%, about 400%, about 450%, about 500%, about 550%, about 600%, about 650%, about 700%, about 750%, about 800%, about 850%, about 900%, about 950%, or about 1000% of the adjusted rate of the dose of hormone.

In some embodiments, the second adjusted rate of the dose of hormone is from about 0.1% to about 0.5%, from about 0.5% to about 1%, from about 1% to about 5%, from about 5% to about 10% from about 10% to about 15%, from about 15% to about 20%, from about 20% to about 25%, from about 25% to about 30%, from about 30% to about 35%, from about 35% to about 40%, from about 40% to about 45%, from about 45% to about 50%, from about 50% to about 55%, from about 55% to about 60%, from about 60% to about 65%, from about 65% to about 70%, from about 70% to about 75%, from about 75% to about 80%, from about 80% to about 85%, from about 85% to about 90%, from about 90% to about 91%, from about 91% to about 92%, from about 92% to about 93%, from about 93% to about 94%, from about 94% to about 95%, from about 95% to about 96%, from about 96% to about 97%, from about 97% to about 98%, from about 98% to about 99%, from about 99% to about 99.5%, from about 99.5% to about 99.9%, from about 101% to about 105%, from about 105% to about 110%, from about 110% to about 115%, from about 115% to about 120%, from about 120% to about 125%, from about 125% to about 130%, from about 130% to about 135%, from about 135% to about 140%, from about 140% to about 145%, from about 145% to about 150%, from about 150% to about 155%, from about 155% to about 160%, from about 160% to about 165%, from about 165% to about 170%, from about 170% to about 175%, from about 175% to about 180%, from about 180% to about 185%, from about 185% to about 190%, from about 190% to about 195%, from about 195% to about 200%, from about 200% to about 250%, from about 250% to about 300%, from about 300% to about 350%, from about 350% to about 400%, from about 400% to about 450%, from about 450% to about 500%, from about 500% to about 550%, from about 550% to about 600%, from about 600% to about 650%, from about 650% to about 700%, from about 700% to about 750%, from about 750% to about 800%, from about 800% to about 850%, from about 850% to about 900%, from about 900% to about 950%, or from about 950% to about 1000% of the adjusted rate of the dose of hormone.

In some embodiments, subsequent to the subject being in the state of physical exercise, while the subject is in the second state of physical exercise, the heart rate of the subject is modified to a second active level that is from about 50% to about 100% of the maximum heart rate of the subject. In some embodiments, the heart rate of the subject is elevated to the active level that is from about 50% to about 55%, from about 55% to about 60%, from about 60% to about 65%, from about 65% to about 70%, from about 70% to about 75%, from about 75% to about 80%, from about 80% to about 85%, from about 85% to about 90%, from about 90% to about 95%, or from about 95% to about 100% of the maximum heart rate of the subject.

In some embodiments, the glucose level of the subject during the state of physical exercise is above the critical glucose range and the heart rate of the subject is modified to the second active level that is from about 50% to about 60%, from about 60% to about 70%, or from about 70% to about 80% of the maximum heart rate of the subject. In some embodiments, the glucose level of the subject during the state of physical exercise is below the critical glucose range and the heart rate of the subject is modified to the second active level that is from about 90% to about 100% of the maximum heart rate of the subject.

In some embodiments, an exercise instruction of the disclosure is based upon a time of day. Non-limiting examples of times of day include early morning, mid-morning, afternoon, and evening. In some embodiments, the exercise instruction of the disclosure is based upon a diet consumed by the subject. In some embodiments, the exercise instruction of the disclosure is based upon an activity of the state of physical exercise. In some embodiments, the activity lowers the glucose level of the subject. In some embodiments, the activity raises the glucose level of the subject. If the subject chooses and exercise to perform, the system can modify the subject's insulin or glucagon administration rate based on the time of day, the selection of exercise, and other factors, such as heart rate and glucose levels.

Media-Enhanced Exercise Instruction

A subject can receive exercise instruction for safe and effective activities for a diabetic. The subject can receive exercise instruction while using any device or system herein, or can receive exercise instruction without using any such device or system. Exercise instruction can be presented to the subject in any suitable format, for example, video, audio, email, text, in-person, presentation of words associated with an exercise instruction, presentation of sounds or symbols associated with an exercise instruction, group, one-on-one, and any combination thereof. Devices suitable for presenting exercise instruction include a media device, a communication medium, a video display device or unit, an audio device or unit, immersive virtual reality device, a hologram or holographic display medium, a device suitable for conveyance of email or text message, such as a computer, cellular telephone, or tablet, mannequins, posters, flyers, and any combination of the foregoing. In some embodiments, the subject inputs into the system a choice of exercise to perform, and receives instruction based on the subject's choice of exercise.

Figure 1:
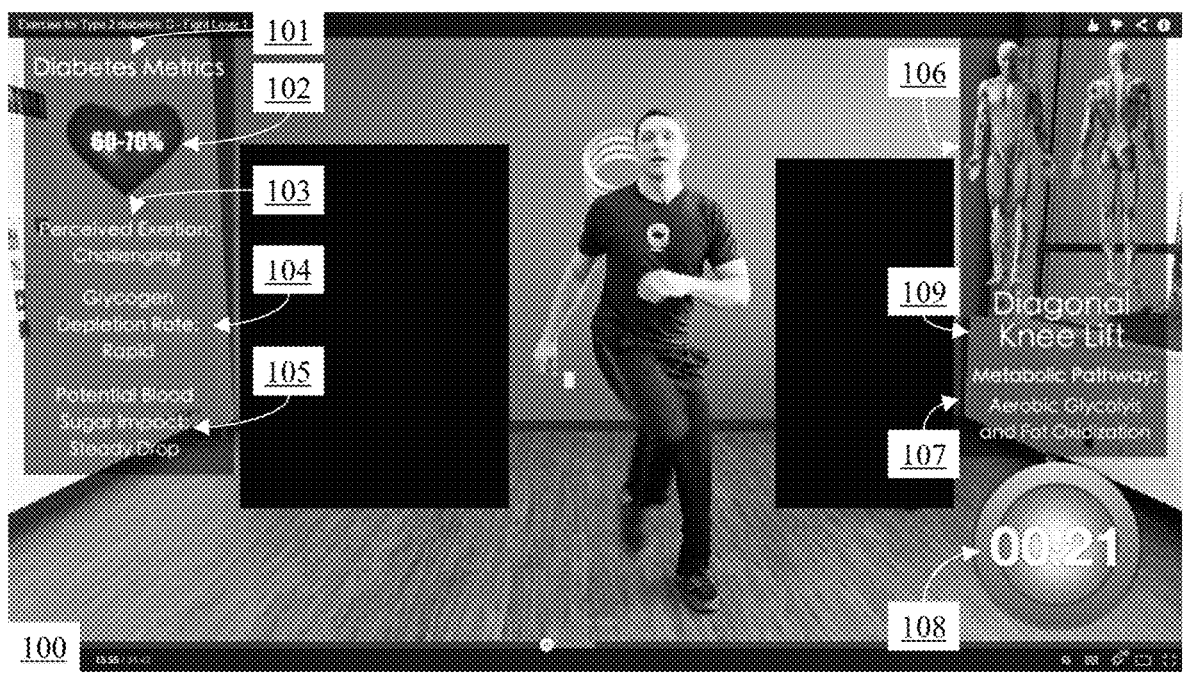
FIG. 1 illustrates an audiovisual data stream of the interactive exercise program.

FIG. 1 illustrates an example video display for exercise instruction 100. The video for exercise instruction 100 comprises multimedia video content featuring exercise instruction and correlating presentation of diabetes metrics 101, including suggested heart rate zone 102, suggested perceived exertion rate 103, suggested glycogen depletion rate 104, potential blood glucose impact 105, suggested skeletal muscle usage 106, suggested metabolic pathway 107, amount of time per exercise 108, and name of exercise performed 109.

Video instruction for each exercise is presented on an electronic device to the subject in real time, and the subject can participate by performing or learning the exercise. Non-limiting examples of electronic devices include displays, computers, televisions, projectors, smartphones, smart watches, tablets, and electronic glasses. As the video for exercise instruction proceeds, and the instructor progresses through a series of exercises, information is displayed on the video output. Each exercise instruction is accompanied by the provision of suggested information related to desired results illustrated as side bars and popups in the video for exercise instruction.

Figure 2:
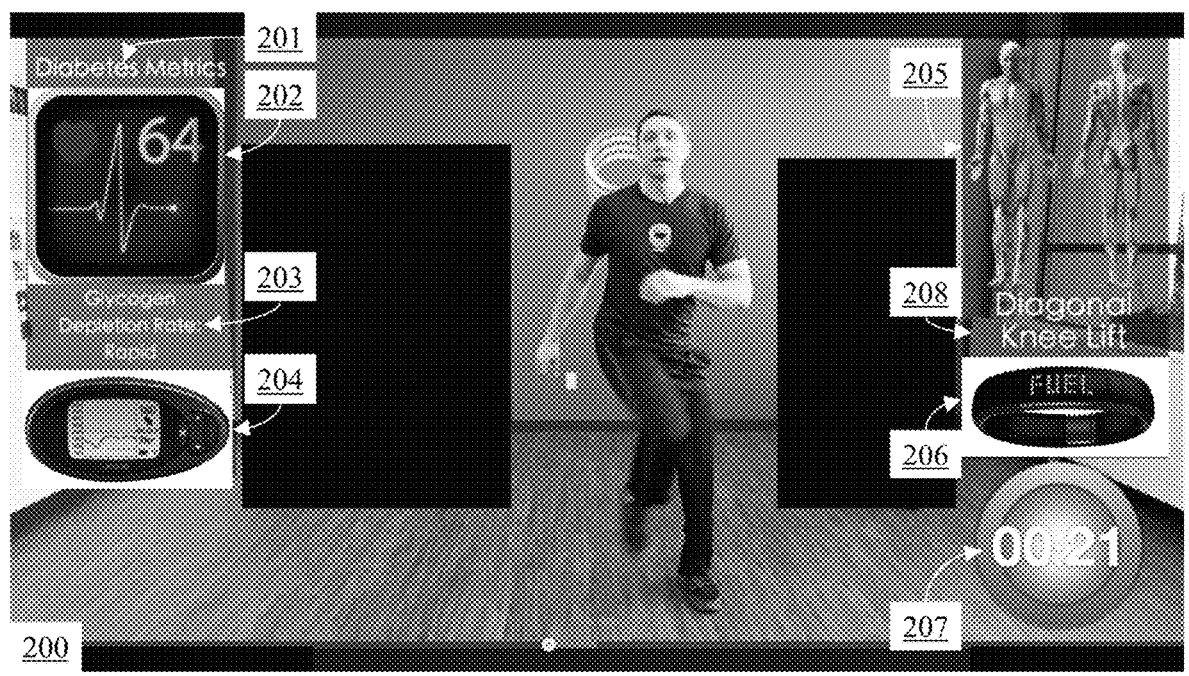
FIG. 2 illustrates an audiovisual data stream of the interactive exercise program.

FIG. 2 illustrates an example video display for exercise instruction 200. The video for exercise instruction 200 comprises: multimedia video content featuring exercise instruction integrating content with software and devices that track biometric data related to diabetes and health metrics in real time. In this embodiment, the video for exercise instruction 200 combines the presentation of suggested data and information with the presentation of diabetes metrics 201 integrating real-time biometric data, including active heart rate 202, suggested glycogen depletion rate 203, blood glucose level 204, suggested skeletal muscle usage 205, calorie expenditure and geospatial distance covered 206, amount of time per exercise 207, and name of exercise performed 208.

Biometric data can be incorporated and derived from software and wearable biometric tracking devices, sensing and image analysis data obtained from cameras on a smartphone or telecommunications device, sensing and image analysis data obtained from external cameras, including visible spectrum and infrared cameras, and smartphone applications that track distance, speed, time and geography covered. These devices are worn by the subject, and monitor the signals of the subject. Data collected from these devices are transmitted to the system of the invention, which processes the data to provide a real-time display of data generated from the subject. The subject thus has the opportunity to observe and evaluate performance and compare output to recommended standards. The data can replace or supplement the suggested data, and are displayed in real time through Application Program Interface (API) protocols and BlueTooth® integration.

Non-limiting examples of potential biometric data and smartphone application information include information derived from heart rate monitoring devices; information derived from external hormone delivery devices, such as insulin pumps and glucagon pumps; information derived from continuous glucose monitoring (CGM) devices; information derived from non-continuous glucose monitoring devices, such as blood glucose meters (BGMs); information derived from calorie expenditure devices; information derived from step counters; information derived from time and clock applications; information derived from metabolic pathway devices, such as New Leaf™ technology; and information derived from distance, speed and geospatial distance tracking devices, such as GPS technology.

In some embodiments, the disclosure herein provides methods for suggestive and responsive multimedia exercise instruction featuring, for example, a smartphone application that integrates exercise instruction and video content with biometric software and devices to make exercise suggestions based on desired diabetes metrics outcomes. Non-limiting examples of such outcomes include A1C reduction; A1C goal; increase in insulin sensitivity; decrease in insulin resistance; fat metabolism and weight loss; real-time lowering of blood glucose levels; real-time elevation of blood glucose levels; and reduction of anti-diabetic medication usage.

Utilizing the software, protocols, and algorithms described above, an application makes exercise suggestions based on factors geared towards exercise effective for a diabetes patient. Non-limiting examples of such factors include pre-exercise glucose levels; information derived from individual diabetes profile; established safety guidelines related to comorbidity conditions; real-time feedback from biometric devices; algorithms described herein; and categorization of exercise routines correlated with specific diabetes outcomes and conditions.

Figure 8:
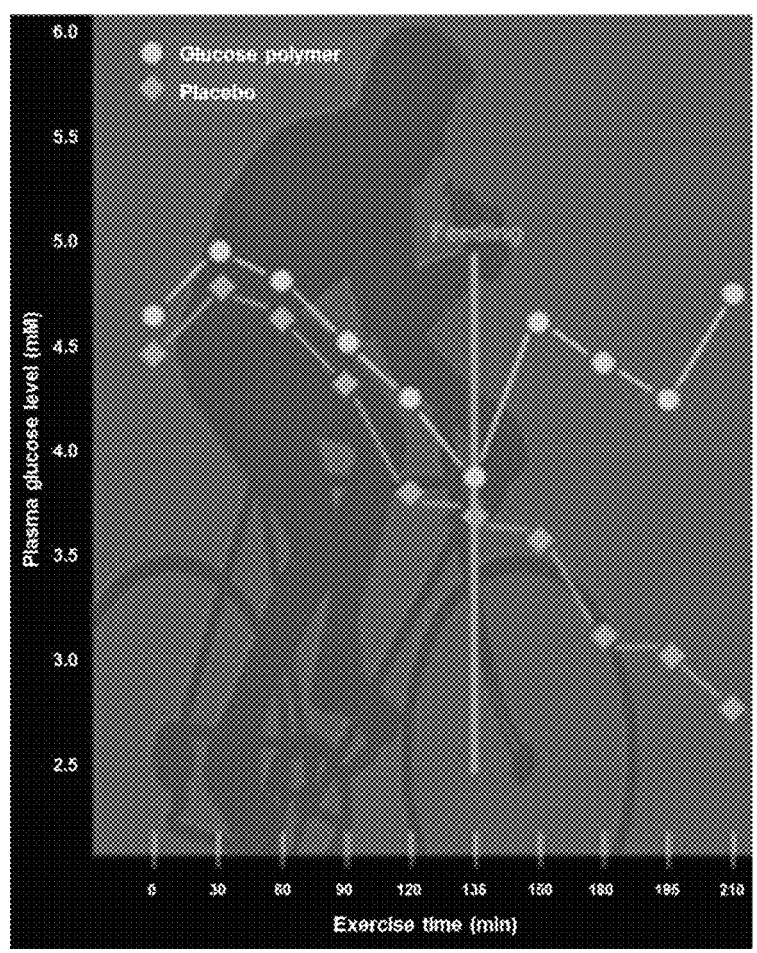
FIG. 8 illustrates a graph of plasma glucose concentration during aerobic exercise.

FIG. 8 provides a graphical depiction of average plasma (blood) glucose level in millimolar (mM) over a period of exercise time in minutes (min) in individuals consuming either placebo (diamonds) or glucose polymer (circles) during prolonged, high-intensity aerobic exercise. Using the methods, systems, algorithms, computer program products, and computer-executable code of the disclosure for exercise guidance, blood glucose levels can be monitored over an exercise time course.

In some embodiments, an application platform disclosed herein provides a portal for subjects and providers to: input diabetes-specific biometric data such as glucose level, heart rate level and medication, such as manually via a smartphone application; receive specific and responsive exercise guidance based upon real-time data entry of diabetes-related biometric data, utilizing the clinical algorithms for exercise therapy; offer care providers a structured exercise program that can be both prescribed and reviewed; and integrate the algorithms and apps with wearable devices, biometric monitoring devices, and drug delivery devices to automate the input of diabetes-related biometric data and provide responsive exercise suggestions, based on the real-time flow of automated data.

The subject can have target ranges for various parameters, including biometric parameters and device parameters, such as dosage rates for insulin and glycogen administration devices. The target parameters can be pre-determined, prescribed, or determined by the subject, a health care professional, or a fitness professional. The system can alert the subject when a parameter deviates from a target range, for example, by audio, video, text, email, or by shutting down the exercise instruction program. The system can also modify the exercise program to instruct the subject to undertake activities likely to adjust the parameter back to the target range.

Interactive Safety Monitoring

During exercise, user biometrics can be assessed in real-time to provide actionable advice to a user when the system detects measurements that suggest medical danger.

For example, when fasting blood glucose levels increase to about 240-300 mg/dL, the user can be alerted of dangerously high blood sugar. The user can be advised to administer insulin to reduce glucose levels. When blood glucose levels exceed 300 mg/dL, the system can automatically connect the user with a health care professional. Alternatively, when fasting blood glucose levels decrease to about 70-90 mg/dL the user can be alerted of dangerously low blood sugar, and can be advised to intake sugar immediately to normalize blood glucose levels.

Relative rates of biometrics variables can also suggest whether medical attention is needed. Detection of dangerous relative rates of biometrics can trigger automated alerts to and/or connection with an authorized diabetes professional (e.g., a doctor, nurse, or certified diabetes educator), caregiver, or entity. In addition to absolute biometric measurements, the system can detect biometric rates and fluctuations. Relative rates of biometrics variables can also suggest whether medical attention is needed.

Biometrics can include, for example, heart rate, glucose levels, time of day, diet, medications, and exercise type. In some embodiments, biometric variables can include genomic data of the user.

Fully-Monitored Experience

In some embodiments, the system can provide a fully-monitored experience to a user. Tier 1: a virtual support team and the user can interact with one another. For example, a user can communicate a question, concern, or comment to a support team member. User/support interactions can be facilitated through an instant messaging interface, a video conference, or a phone call. Tier 2: the system can identify a condition based on user biometrics and automatically perform an action to modify or correct that biometric of the user. The action can include, for example, alerting the user through a visual or audio notification to adjust an insulin dosage, adjustment of an insulin dosage, adjustment of a glucagon dosage, and adjustment of an exercise regimen. A user alert can include a recommendation to slow performance of an exercise, a recommendation to stop performance of an exercise, a recommendation to adjust insulin dosage, and a recommendation to consume food or beverage. For example, the system can detect very high glucose levels that suggest that the user is experiencing hyperglycemia. The system can automatically increase or decrease the user's insulin dosage. Tier 3: the system can provide access to human interaction to the user. For example, the system can connect the user to a health professional when the system detects unsafe or abnormal conditions. These conditions can include glucose levels have not been correctable after multiple attempts and exercise levels are detected to be unsafe.

Live Trainer Exercise Instruction

In some embodiments, the recommended exercises can be broadcast live from a remote location. Live broadcast provides a real-time video and audio stream of an exercise routine with a real-life trainer. Live broadcast can include multiple daily classes that can be streamed to users worldwide. Live exercise routines or classes can vary in style and difficulty depending on user biometrics.

Users can interact with a live, digital trainer in real-time. Users and digital coaches can interact through bi-directional communications. Digital trainers can receive user data from logged users and send information to users. User data can include biometric data and other user identification information. Accordingly, digital trainers can provide personalized guidance and feedback in real-time. Live broadcast can help facilitate user compliance and engagement. A digital trainer can be a fitness professional, physical therapist, or health care professional.

In addition to live interactions with the digital trainer, users can interact with other users. Users can share experiences and advice with one another to foster a supportive community.

In some embodiments, the system provides a merit-based rewards system to further promote user engagement. For example, the system can monitor daily activity of the user and distribute points.

The system can operate through and/or facilitate machine learning, deep learning, and other neural networks. Thus, prediction factors grow as the system collects more data from a wider range of users. For example, glucose level and other biometrics of a user can be input into the system. Biometrics input can be manually inputted by the user or automatically inputted through a user monitoring device. The system can determine whether the user can safely perform exercises. The system can recommend video content of exercises in real-time based on user biometrics and fluctuations thereof. The system can provide live video and audio programming based on user biometrics and fluctuations thereof. Video programming can change based on user selection and biometric measurements during exercise.

Figure 7:
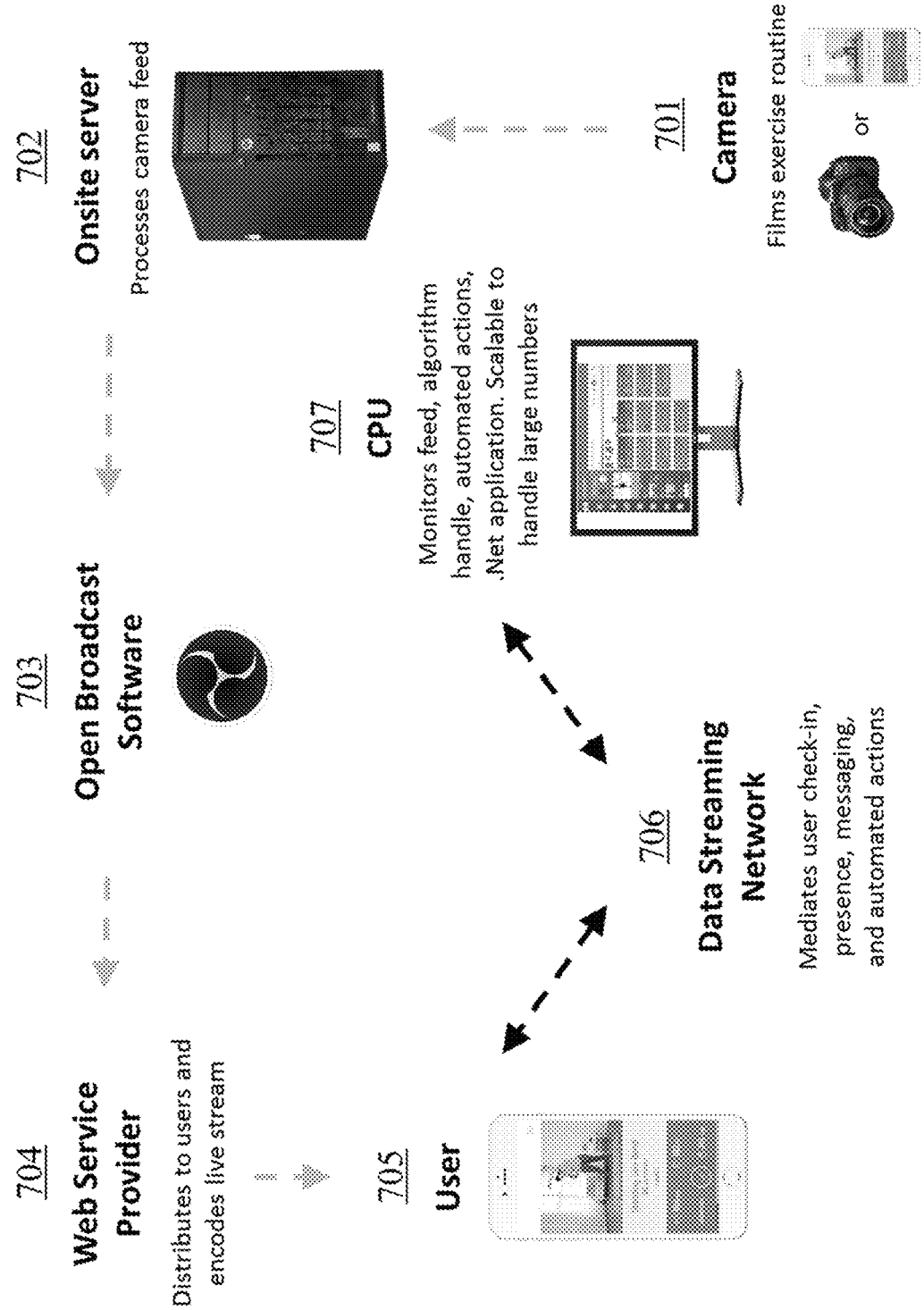
FIG. 7 depicts a live exercise monitoring system for the online sharing of a real-time camera feed of a user.

FIG. 7 illustrates an example of a live exercise monitoring system 700. The live exercise counseling can be based, for example, on a camera feed 701 that films a person performing the exercise. As illustrated in FIG. 7, the camera feed 701 can be processed by a server 702 that is onsite at the point of exercise. Open broadcast software can be used to make the camera feed 701 available to a web service provider. The web service provider can encode the camera stream, and distribute the stream to users 705 of the system using open broadcast software 703 and a web service provider 704. Users can receive the live camera feed on a telecommunications device, for example, a smartphone a cellular telephone, a computer, or any web-access display, to view the camera feed. The user 705 can then view the live exercise in real time. In some embodiments, external cameras can be used to capture the user's image for video production, broadcast, image analysis, or uni-directional and bi-directional communication. Image analysis can refer to the analysis of user images captured by cameras using automated assessment tools, screened and interpreted using human experts and/or artificial intelligence to identify a broad range of physiological, behavioral, or environmental patterns. Non-limiting examples of image patterns include changes in the user's facial complexion (flush or paleness), body posture, facial expression, respiration, perspiration, body temperature, and performance of correct or incorrect movements.

The process can work, for example, bi-directionally. In one direction, the exerciser who is filmed on the live camera feed 701 can be an instructor, whose exercise is being broadcast to users who receive an instructional exercise feed. In the reverse direction, the exerciser can be a subscriber who is in need of exercise coaching, therapy, monitoring, or risk management for diabetic episodes. The recipient or user 705 of the camera feed 701 can be an exercise professional who provides guidance, instruction, and if necessary, rescue instruction in the exerciser becomes at risk of a diabetic episode. Such a risk can be monitored and reported by a biometric device, worn by the exerciser, which feeds into the system.

Users of the system 700 can access an online portal, for example, through a check-in module. Once checked in, the system 700 can monitor the presence of the user, provide the user with a messaging platform, and provide access to automated events through a central processing unit (CPU) 707. The messaging platform can be used for messaging with other users, members of an on-line community, exercise instructors, health care providers, payers, pharmaceutical companies, research entities, IT support specialists, and emergency services. Non-limiting examples of automated events include exercise sessions, the sending or receiving of instructional material, nourishment, checking biometric signals such as heart rate and blood sugar, reminders, and journal entries.

System 700 illustrated in FIG. 7 is scalable. The system can support an individual subscriber, a population of subscribers, an individual exercise instructor, a population of exercise instructors, and any number of participants, specialists, health care providers, payers, pharmaceutical companies, research entities, IT support specialists, and users of any type.

Online Portal for Exercise Instruction

The system can provide an online portal through which users and subscribers can receive exercise instruction. The online portal can provide example exercises, recommended exercises, recommended food and drink, recommended routines, time of day to exercise, and any other information useful for guiding the exercise program. The portal can provide instruction through various media. Instruction can be through images, pictures, photographs, video clips, cartoons, voice, or audio instruction of exercise. The instructions can be designed to be used during exercise, in preparation for exercise, or for future advice.

In some embodiments, the online portal can provide live exercise instruction from a human instructor. For example, live exercise instructions can be offered daily, weekly, bi-weekly, or monthly.

A user can access the online portal through a log in. Once logged in, the user can access various personalized features, for example, a calendar, a schedule, list of preferred exercises, a community of participants, a journal, dietary advice, health quizzes, reward programs, a progress report, a history of past exercises, and a history of diabetic episodes. The user can access these features to provide a customized exercise environment.

In some embodiments, the online portal can access any biometric equipment attached to the user, such as a heart rate monitor and a glucose meter. The portal can read the biometric devices and display the readings to the user. The portal can also search a database of exercise and diabetes resources in real time to determine options for the user and possible risks. For example, the portal can identify that the user should change the current exercise based on biometric readings. The portal can suggest a different, safer exercise based on the readings. In some embodiments, the user has the option to browse a list of exercises that the portal identifies as safe for the current biometric readings. The user can scroll, swipe, or otherwise browse exercise alternatives to choose one to perform.

Upon choosing an exercise, the user can access instruction information. For example, the user can watch a video that illustrates proper exercise form. The user can also access information about the exercise itself, and any risks associated with the exercise.

In some embodiments, the online portal connects the user to a monitoring system. The monitoring system can be automated, or staffed by health care or exercise specialists. The monitoring system can identify changes in biometric parameters during use, and identify readings that are safe, effective, or risky. The portal can notify the user of the finding. When the readings show risk, the system can intervene to attenuate the risk. An automated system can automatically send intervention instructions to the user upon determining the risk. A staffed system can allow a specialist to analyze the information and determine an intervention for the user based on sound professional judgement. The intervention can be, for example, a change in exercise, a change of the pace of exercise, stopping exercise, drinking water, eating or drinking a sugary food, or activating a rescue device, such as an insulin or glucagon pump.

Augmented Reality

The system can provide an augmented (virtual) reality to create a gamified interface for users. The invention includes systems and methods for regulating and scoring user exercise milestones in a virtual reality game. For example, users can walk, run, ride a bicycle, or perform other movement-based exercises in a virtual landscape alongside other users. The virtual landscape can be a location-based parallel reality. The virtual landscape can change during the course of the exercise. For example, users can be advised to complete a virtual obstacle course while performing an exercise. The obstacle course can vary in location, landscape, and difficulty. In some embodiments, users can interact with other users based on detected user locations. A fully-immersive, interactive experience provided by the system can provide further incentive to comply with exercise recommendations.

The location-based parallel reality hosted by a game server can include a virtual gaming environment with geography that parallels real world geography. Users or players can engage in movement-based exercises while navigating through a range of coordinates that correspond to geographic space in the real world. Accordingly, users can be monitored or tracked using location-based position-tracking systems (e.g. GPS) associated with a user's mobile device.

In some embodiments, the system can monitor user progress including, for example, pace, distance, elevation, heart rate, glucose level, and insulin level. The system can generate personalized exercise plans for users based on user-inputted personal goals, user biometrics, and fitness level. In some embodiments, users can compare their progress with that of other users and compete with friends or fellow users.

In some embodiments, the system can provide personalized music playlists, Podcasts, or audio support or guidance while a user is performing an exercise.

The navigational medium can be based on user biometrics. User biometrics can be measured to predict and recommend different types of exercises to a user. For example, a user can be performing a running exercise in an augmented reality landscape and experiences a trending pattern of blood glucose readings (e.g., up or down at different rates of change) from a continuous blood glucose monitor. The landscape of the augmented reality of the user can change to increase or decrease the level of effort for navigation depending on the desired impact on the trending blood glucose level.

Exercise recommendations can be automatically displayed after user biometrics are detected. Biometrics can include, for example, heart rate, glucose levels, time of day, diet, medications, and exercise. In some embodiments, biometric variables can include genomic data of the user.

Targeted Advertising Based on Biometric Data

Biometric data can provide valuable information about a user's health and lifestyle, which can be associated with a product or service in the form of an advertisement.

Instead of random presentation of advertising and retail information to a user, an advertiser can more effectively connect with a user by targeting a particular user demographic by monitoring and analyzing user biometrics. Target advertising increases the likelihood of a user to view an advertisement more favorably and purchase the advertised product or service. Systems described herein can be used to identify, select, and present product, service, program, advertisement, or other information to a user without user intervention based on predicted compatibility with user biometrics and demographics.

Non-limiting examples of user biometrics are shown in FIG. 13. User biometrics factors include user information, such as emotional state, community interactions, hobbies, interests, occupation, environmental influences, health biometrics, diet, fitness level, exercise habits, and medical intervention. Emotional state describes the psychological or mental state of the user, which can fluctuate based on the physiological health of the user. Emotional states can affect user compliance to health recommendations, which can contribute to poor disease prognosis. Community interactions and hobbies can describe user interests and social network, which can provide information on user lifestyle preferences. User occupation can provide information about user fitness level and occupational therapy. Systems disclosed herein can process user occupational or daily activity information to generate personalized and integrated health recommendations. Environmental influences can include weather, climate, and elevation based on the location of the user. Health biometrics can include cardiovascular biometrics, blood glucose level, insulin level, heart rate, pulse rate, pulse oximetry, body fat percentage, visceral fat percentage, muscle mass percentage, respiration rate, respiratory quotient, bone mass, body water, body mass index, weight, internal body temperature, external temperature, cortisol level, ketone level, hormone levels, and medication usage. Diet is a major contributor to overall health of an individual. For metabolic diseases, such as diabetes, diet and nutrition play a crucial role in disease management. Monitoring and improving dietary habits can improve disease prognosis. Fitness level and exercise habits can provide information of the physical health of an individual. Systems disclosed herein can provide instructional exercises that match an individual's fitness level and exercise preferences, which can improve exercise adherence and prevent the likelihood of injury. Medical interventions or medications used by an individual can provide information about health state, disease prognosis, and potential side effects that can influence the type of health guidance provided by a system described herein.

Figure 14:
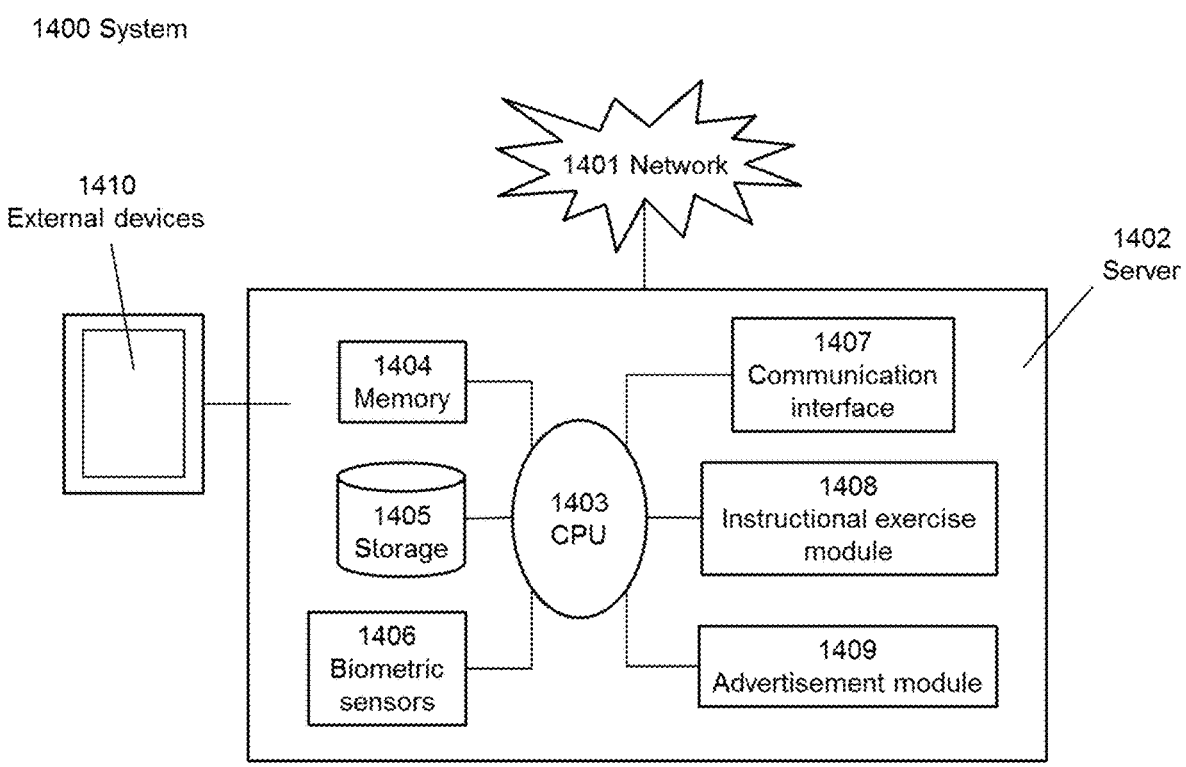
FIG. 14 illustrates a computer system for facilitating methods, systems, kits, or devices of the disclosure.

FIG. 14 illustrates a computer system 1400 programmed or otherwise configured to allow monitoring of a biometric of a subject by biometric sensors 1406 or external biometric devices 1410, presentation of an instructional exercise by instructional exercise module 1408, and presentation of an advertisement by advertisement module 1409, in accordance with various embodiments of the disclosure. The computer system 1400 includes a server 1402, a CPU 1403, a memory 1404, a storage unit 1405, biometric sensors 1406, and a communication interface 1407.

The system 1400 receives a biometric measurement of a subject from biometric sensors 1406 or external devices 1410, for example, a biometric device. The system 1400 then generates by instructional exercise module 1408 an instructional exercise for the subject to perform based on the detected or received biometric measurement. The system 1400 generates an advertisement by advertisement module 1409 that is targeted to a subject based on a subject's real-time biometrics, which can be stored in storage unit 1405 or received from external devices 1410. Communication interface 1407 presents the instructional exercise and advertisement multimedia generated from the subject's real-time biometrics.

In some embodiments, the system 1400 generates a targeted advertisement while a subject is performing the instructional exercise provided by instructional exercise module 1408. In some embodiments, the system 1400 generates a targeted advertisement based on a historical biometric measurement in the subject detected and/or received by the system.

Storage unit 1405 includes a database of instructional exercises, which can be divided by various categories based on, for example, type of exercise and the challenge level. Storage unit 1405 further includes a database of advertisements. In some embodiments, instructional exercise and advertisement multimedia can be provided via external devices.

Figure 15:
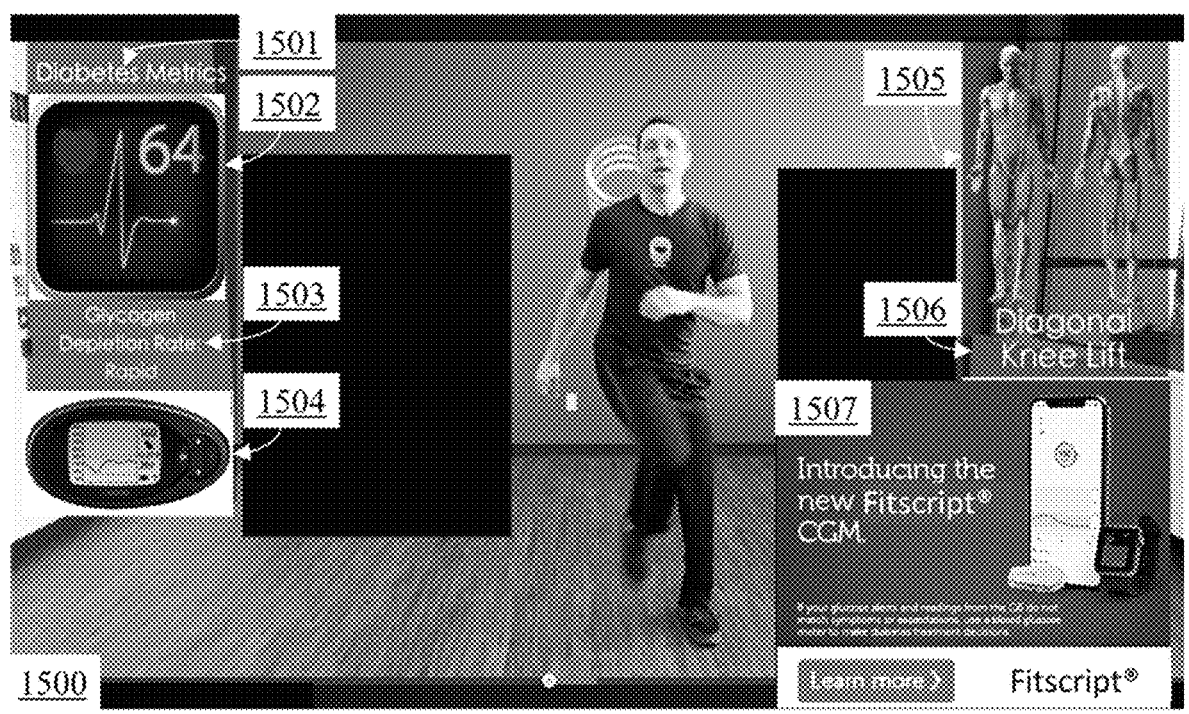
FIG. 15 illustrates an audiovisual data stream of the interactive exercise program.

FIG. 15 illustrates a system 1500 for biometrics-based instructional exercise and advertising. The system for exercise instruction 1500 includes a multimedia video content featuring exercise instruction integrating content with software and devices that track biometric data related to diabetes and/or health metrics in real-time. The system 1500 combines presentation of instructional exercise with the presentation of diabetes metrics 1501 integrating real-time biometric data, including active heart rate of a user 1502, suggested glycogen depletion rate 1503, blood glucose level 1504, graphic of instructional exercise 1505, name of exercise 1506, and biometrics-based advertisement 1507.

Systems disclosed herein can present to a user demographic group types of advertisements that match detected or predicted interests and/or biometrics. Advertisements for products, services, programs, and other information can be presented to a user through various digital communications channels, including for example, a mobile application, an e-mail, a text message, a social media account, or any other communication medium that provides access points to a user.

Further, systems disclosed herein can engage with users through multimedia communication systems to improve the quality of targeted advertising based on personal preferences of an individual user. Increasing the ability of the user to control which advertisements are received further improves user favorability of targeted advertisements and increase likelihood that the user purchases the advertised product or service. For example, a user can be presented with questionnaires to gauge the user's interest in a particular advertisement. User feedback can be integrated into the biometric data analysis to refine the targeted advertising process.

The targeted advertising systems disclosed herein can be integrated with systems of exercise guidance based upon user biometrics detected in real-time. Presentation of an advertisement can be based on the type of exercise recommended by the system to or selected by the user. For example, a user recommended to do jogging exercises can be presented an advertisement for a social running club or running accessory products. Presentation of an advertisement can be based on changes in user biometrics during performance of an exercise. For example, a user of the exercise media device can be approaching completion of an exercise routine, and the user's blood glucose level is detected to be low. The low level necessitates that the user restores blood glucose levels by food consumption. In response, the system can present to the user advertisements for a food or beverage product suitable to adjust the blood glucose level as needed.

Presentation of targeted advertising can also be based upon an exercise recommendation provided by an instructional exercise program. For example, a user performing or instructed to perform weight lifting or resistance training exercises may be interested in exercise accessory products. In response, the system can present to the user advertisements for an exercise accessory product, for example, weights, dumbbells, mats, exercise bands, or protective gear.

Further, the targeted advertising systems disclosed herein can present targeted advertising based on monitoring of user interactions with multimedia. Monitoring user interactions with multimedia enables the system to detect a user interest. User identity profiles can be used to identify user market preferences. The system can shape a user identity profile from information obtained from monitoring of user interactions with multimedia. User market preferences based on history of purchases can reflect the future user purchasing interest. A user identity profile can be determined in real-time. For example, a user who enjoys hiking can have a user identity profile listing hiking as a user market preference.

Non-limiting examples of ways in which the system can monitor user multimedia interaction include clicks, browsing history, purchase history, social media use history, calendars, e-mail, message logs, call logs, and computing cookies. A user's online presence in social media and non-social media websites can be used to identify product preferences. Non-limiting examples of social media websites include Facebook®, YouTube®, Instagram®, Twitter®, Reddit®, Pinterest®, Tumblr®, Flickr®, Google+®, Meetup®, Qzone®, Weibo®, and LinkedIn®. The monitoring can take place, for example, on a personal computer, television, mobile device, tablet, or video game console.

Prior to monitoring of user interactions and/or biometrics for target advertising, users can opt in or out of tracking and/or analysis of multimedia interaction for this purpose. In some embodiments, the monitoring can be activated upon user approval. In some embodiments, the monitoring can be activated without user approval. The output of the monitoring can reported to a central hub in which a computer system processes the output to determine the user market preferences on the user interactions with media devices.

Non-limiting examples of media devices include personal computers, mobile telecommunications devices, tablet devices, televisions, and video game consoles. Non-limiting examples of media experiences include web browsing, social media browsing, listening to sounds, music, or audio clips, watching a video or program, such as a television program, playing a game, composing an e-mail, texting, messaging, conversing, online shopping, and otherwise participating in a media entertainment experience. The advertisement can be an advertisement electronic communication medium including, for example, a video or photograph.

The targeted advertising systems disclosed herein can allow users to design the advertising experience manually. For example, a user can hide or reject a received advertisement or notification by selecting an icon on the advertisement communication. The user can specify reasons for hiding the received advertisement. Reasons can include, for example, because the advertisement is spam, offensive or inappropriate, uninteresting, repetitive, not relevant. Thus, the system can combine automatically-generated, biometrics-based advertising with manual input of user advertising preferences. In this way, the system can learn new user preferences and improve the advertising experience for the user over time.

Users can further tailor the advertising experience by creation of a user profile and select specific areas of interests, for example, hobbies, interests, and general areas of interest to guide the targeted advertising. A user can choose preferred exercise types (e.g. pilates and running) or advertisement types (e.g. services or products).

The system can present to a user a virtual catalog of various user markets that can be chosen by the user. Once a user interest has been identified, a system of the invention can launch a program, such as a module, window, or notification via the media associated with the user. The user can choose to access or ignore the program. The program can present information to the user based on a previously-identified interest. The information can relate to a user market associated with the interest previously detected by the system. For example, a user detected to have a history of diabetes product purchases can be presented with products or services related to diabetes or diabetic health management.

The program can present the user with a series of options, for example, selectable icons. The selectable icons chosen for presentation to the user relate to the user's identified interest. Each icon can represent a different aspect or niche of the user market, which suggests a product or service, or class of products or services chosen by the user. The user can select any of the icons to learn more about the products or services, and gain information about how to purchase items or services of the desired category. Upon selection of an icon, the user can be presented with a second, third, or further series of icons, each delving more narrowly and specifically into a market of interest to assist the user with finding products/services of interest. Selecting a selectable icon can be performed, for example, by clicking a clickable icon, dragging and dropping an icon, sliding a selectable icon, or by voice recognition of an icon to a command. The user can navigate the system by selecting one or a plurality of selectable icons. Each successive query module can probe deeper into a user market and provide options and information at higher levels of specificity to provide the user the most beneficial and productive product or service search experience. The query module can also detect that a selectable icon has been selected.

The user can select an icon, whereupon a system of the invention recognizes that an icon has been selected. The computer system associates the selected icon, for example, with a market, a user market, a submarket, or a niche market, and uses the association to guide a search for advertising likely to appeal to the user. The computer system searches a database of advertisements to identify those associated with the icons selected by the user. Ultimately, the search finds advertisements associated with the user's interest.

Once the desired advertisements have been identified, the advertisements can be presented to the user over multimedia devices. The user can browse and make selections for determination of future types of targeted advertising. In doing so, the user can learn about products of potential interest and contemplate purchase. The user can be presented with advertisements for desired products, and advertisements for products that the user might not have considered previously, but may consider based on the user's selections and the interest detected by the system.

For example, users can select "medical devices" as an interest and subsequently choose "continuous glucose monitor" as a preferred subcategory within the category of medical devices. Users, advertisers, merchants, and publishers can select on any number of selectable icons that are associated with a user market associated with the media entertainment experience.

The efficiency and quality of the process can be improved by monitoring the same user's media experiences across multiple media devices. Monitoring can take place across two, three, or more media devices. Non-limiting examples of media devices include a personal computer, television, telephone, mobile device, tablet, and a video game console. In some embodiments, the media devices are in communication with a common host, such as a hub, a network, an internet, an intranet, a server, a domain, or a computer system. In some embodiments, communication takes place via a communication module. The system can function on smartphones, tablets, desktop computers, laptop computers, and a plurality of mobile devices with a plurality of different interfaces and operating systems. This versatility allows a user to have access to the system of the invention on a plurality of distinct devices.

In some embodiments, the invention is provided in the form of a computer program product comprising a computer-readable medium having computer-executable code encoded therein, the computer-executable code adapted to be executed to implement a method for targeting advertising to a media user. Non-limiting examples of computer-readable media include hard disk, floppy disk, magnetic tape, flash drive, USB, CD, DVD, and Blu-ray Disc. Non-limiting examples of computer-executable code include bytecodes and portable codes such as Java, Small Talk, JIT, Python, PUP, CSS, HTML5, DHTML, Forth, LLVM, and C++.

The system can comprise a computer program product that is constantly received by and presented to an end-user while being delivered by a provider, for example, by streaming media, and live streaming. A system of the invention can use a plurality of different network protocols, for example, user-datagram-protocols (UDP), real time-streaming-protocols (RTSP), real-time-transport-protocols (RTP), the real-time-transport-control-protocols (RTCP), adaptive bitrate streaming, and transmission-control-protocols (TCP) to deliver advertisement.

For example, a user can be watching a cooking show associated with the food, beverage, and nutritional supplement industry. A system of the invention can match the user interest in food/cooking, and offer industry-relevant product information as an advertisement on the television screen. A user can choose to ignore the advertisement or request further product information. A user can choose to save the product information for later review. A user can choose to review and purchase the advertised product or service. In the case of purchase, a user can review the cost, and provide information for shipping and complete payment as appropriate.

The system can archive the data browsing activities performed on devices associated with the system of the invention. The system can also archive the data on a centralized data source. For example, if a customer selects one or more icons with information on "glucose monitors," the system can archive the data to create a library with the interests of that customer. The archive can guide future product suggestions and provide more rapid advertising delivery. The archive can store information related to viewed icons, selected icons, and purchased items, which can be used to establish user profiles over time.

Targeted advertising content can contain, for example, product or service information, event information, purchase information, sales information, virtual and in-store offers, virtual and in-store events, information on loyalty programs, educational information, religious information, travel information, and a plurality of niche advertisement specified by the user. For example, an advertising output module can guide a user to purchase a product or service. An advertising module can inform a user of an upcoming in-store sales event or promotional period.

In some embodiments, the system can connect with a third party market channel, including third party websites. Users can receive targeted advertisement from the system of the invention while navigating a third party market channel. The user can effectuate purchases and subscriptions at a third party market channel. In some embodiments, the user can effectuate purchases and subscriptions through an interface of the system.

Clinical Trial Recruitment Based on Biometric Data

Patient candidate recruitment is a critical bottleneck in the clinical trials process. Recruitment of adequate numbers of patients ("cohorts") for clinical trials can be challenging. The problem is even more severe for clinical studies of therapies used for treatment of rare or complex diseases, and the diseases and treatments that are influenced by multiple factors including, for example, age, gender, ethnicity, comorbidities, behavioral issues, and additional treatment programs, including the use of one or more medications, devices, or therapeutic regimens. For these reasons, clinical trial recruitment is often laborious, expensive, time consuming, and inefficient. In addition, patients who are interested in participating in clinical trials are seldom directly informed about clinical trials that fit the specific demographics and biometric profile of the patient. Targeted advertising of clinical trials to eligible patients can lead to improved rates of clinical trial recruitment.

Clinical trial recruitment systems disclosed herein can obtain and compile biometric data from multiple users through multimedia devices communicatively coupled to an external server. Compiled biometric data can be analyzed to determine patient eligibility for clinical trial studies. For example, patient electronic health records and biometric data can be used to determine clinical trial eligibility. Patient candidates must meet certain static criteria and/or dynamic criteria to qualify for a particular study. Static criteria can include, for example, disease diagnosis, medical history, gender, age, sex, ethnicity, location, body mass index (BMI), and genotype. Dynamic criteria can include, for example, biometric fluctuations in real-time, fluctuations in blood glucose levels over different lengths of time, fluctuations in blood glucose levels based on different types of exercise, fluctuations in blood glucose levels based on the time and dosing of different types of medications, and fluctuations in blood glucose levels based on food intake.

Clinical researchers, principal investigators, or other clinical trial designers can specify patient eligibility requirements that are used to identify patient biometrics that match the eligibility requirements of a particular clinical trial. A patient database can include users of an instruction exercise program described herein.

The system can analyze compiled patient databases to determine eligible patient participants for a particular clinical trial study. After determining patient eligibility, the system can present to eligible patients targeted multimedia notifications about a relevant clinical trial and provide a connection to eligible patients with clinicians or researchers for further consultation. The system can also provide clinicians or researchers with eligible patient information, for example, the number of eligible patients, patient medical history and other health biometrics, and patient contact information.

In some embodiments, the system can analyze compiled clinical trial databases to determine available clinical trial studies for a patient seeking to participate in a clinical trial. Non-limiting examples of users of the systems described herein include clinical researchers, principal investigators, physicians, health care professionals, and patients.

The clinical trial recruitment system can begin with a patient accessing an exercise guidance program on a media device. The exercise guidance program can monitor and record user biometrics in real-time. The recorded biometric data can be transmitted to the clinical trial recruitment system for analysis. Patient eligibility can change based on a change in a user biometric. Non-limiting examples of media devices include personal computers, mobile devices, televisions, and video game consoles. Non-limiting examples of user biometrics include disease diagnosis, medical conditions, electronic health records, medical history, family medical history, patient medications, exercise history, risk factors, age, sex, demographics, and other criteria relevant to clinical trial eligibility.

Prior to analysis of user biometrics for identification of clinical trial eligibility, users can opt in or out of tracking and/or analysis of user biometrics for this purpose. Furthermore, users can opt in or out of receiving notifications regarding open clinical trials.

Figure 16:
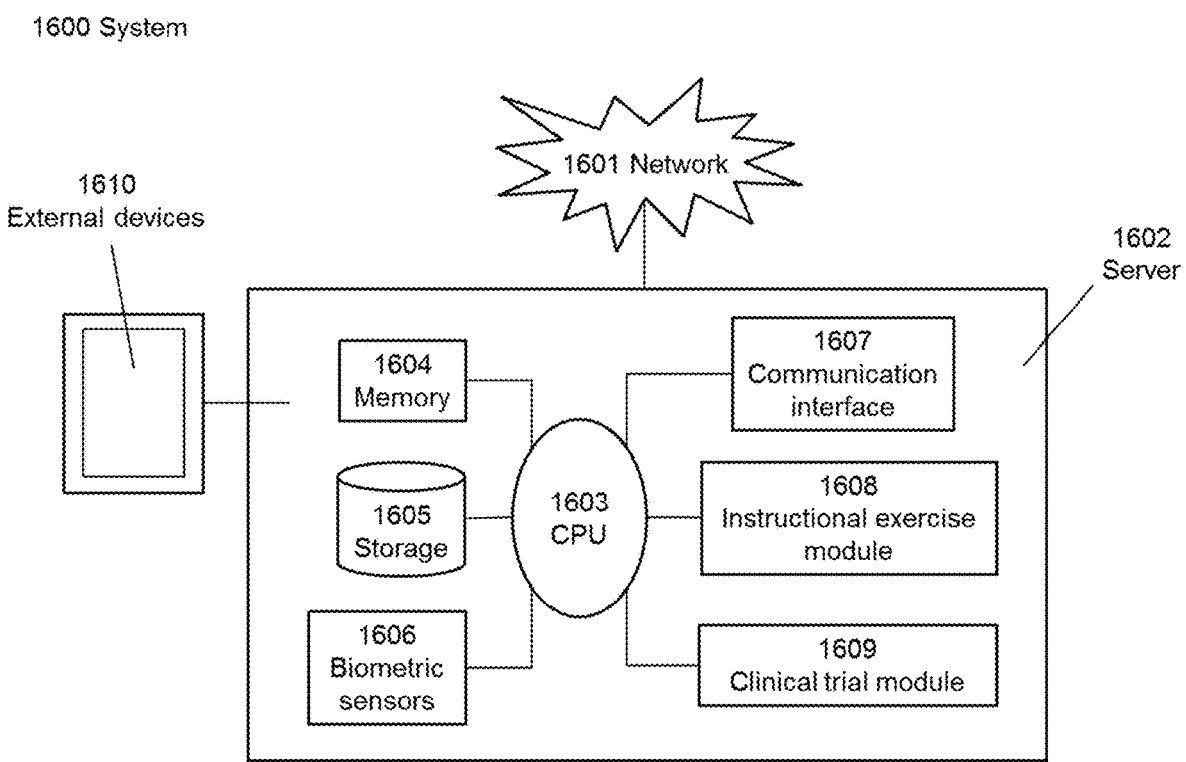
FIG. 16 illustrates a computer system for facilitating methods, systems, kits, or devices of the disclosure.

FIG. 16 illustrates a computer system 1600 programmed or otherwise configured to allow monitoring of a biometric of a subject by biometric sensors 1606 or external biometric devices 1610, presentation of an instructional exercise by instructional exercise module 1608, and presentation of a clinical trial notification by clinical trial module 1609, in accordance with various embodiments of the disclosure. The computer system 1600 includes a server 1602, a CPU 1603, a memory 1604, a storage unit 1605, biometric sensors 1606, and a communication interface 1607.

The system 1600 receives a biometric measurement of a subject from biometric sensors 1606 or from external devices 1614, for example, a biometric device. The system 1600 then generates by instructional exercise module 1608 an instructional exercise for the subject to perform based on the detected or received biometric measurement. The system 1600 further generates by clinical trial module 1609 a notification about a clinical trial study that may be relevant to the subject based on the subject's real-time biometrics. Communication interface 1607 presents the instructional exercise and advertisement multimedia generated from the subject's real-time biometrics, which can be stored in storage unit 1405 or received from external devices 1410. Communication interface 1607 can further provide a connection to the subject with a clinician or researcher for further consultation.

In some embodiments, clinical trial module 1609 determines eligibility of the subject for a particular clinical trial based on subject biometrics received during performance of the instructional exercise. In some embodiments, the system 1600 determines clinical trial eligibility based on a historical biometric measurement in the subject detected and/or received by the system.

Storage unit 1605 includes a database of instructional exercises, which can be divided by various categories based on, for example, type of exercise and the challenge level. Storage unit 1605 further includes a database of clinical trials and associated patient eligibility filters, for example, disease type and comorbidities. In some embodiments, instructional exercise and clinical trial multimedia can be provided via external devices.

Figure 17:
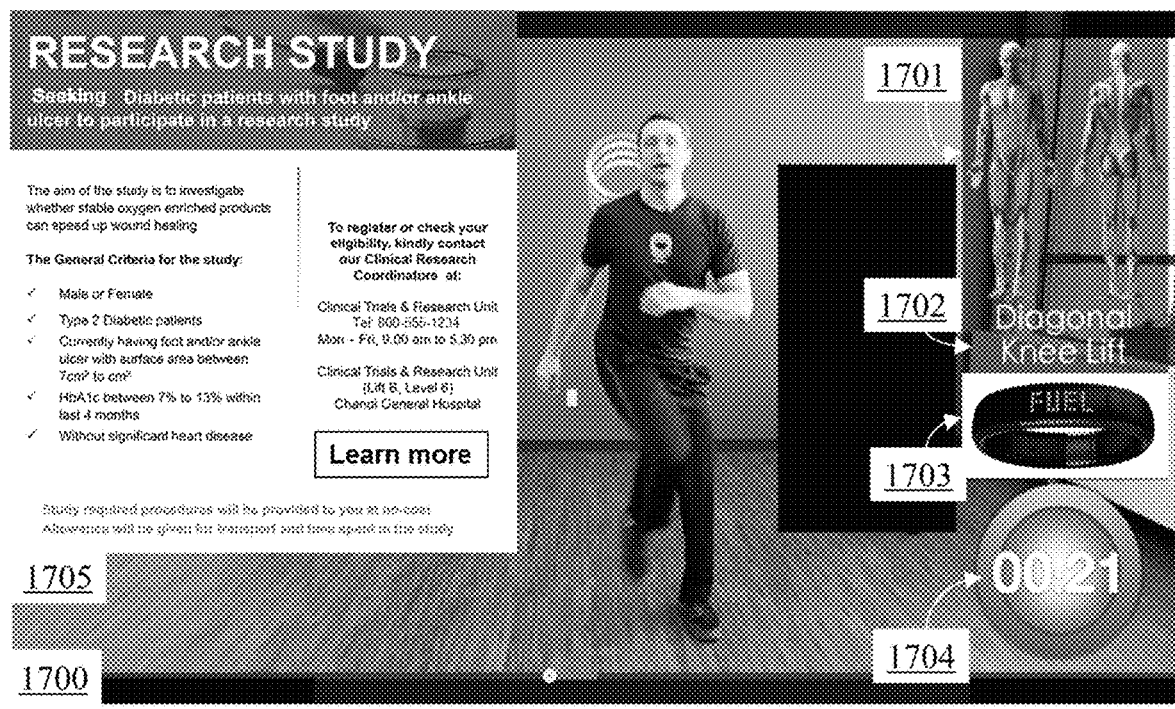
FIG. 17 illustrates an audiovisual data stream of the interactive exercise program.

FIG. 17 illustrates a system 1700 for biometrics-based instructional exercise and clinical trial recruitment. The system for exercise instruction 1700 includes a multimedia video content featuring exercise instruction integrating content with software and devices that track biometric data related to diabetes and/or health metrics in real-time. The system 1700 combines presentation of instructional exercise with the presentation of diabetes metrics 1701 integrating real-time biometric data, graphic of instructional exercise 1701, name of exercise 1702, calorie expenditure and geospatial distance covered 1703, amount of time per exercise 1704, and biometrics-based clinical trial notification 1705.

Biometrics Monitoring

Systems described herein can be configured to receive biometric data from a broad array of multimedia devices, for example, sensors, wearable devices, and/or medication delivery devices (e.g., insulin pumps and glucagon pumps). Biometric data can be collected from manual, periodic user input. Biometric data can be collected from continuous, real-time data received from a biometric sensing device with automated data interfaces. Manual and automated data are unique to individual users. Biometric data can be used to determine types of products, services, programs, or information that may interest a user. Accordingly, systems described herein can be used to identify, select, and present product, service, program, advertisement, or other information to a user without user intervention.

Biometric data can include, for example, cardiovascular biometrics, blood glucose level, insulin level, heart rate, pulse rate, pulse oximetry, body fat percentage, visceral fat percentage, muscle mass percentage, respiration rate, respiratory quotient, bone mass, body water, body mass index, weight, internal body temperature, external temperature, cortisol level, catecholamine level (e.g., epinephrine, norepinephrine, and dopamine), ketone level, hormone level, and medication usage. In some embodiments, biometric data can include sleeping habits, emotional states, and psychological state.

Integration of Diabetes Exercise Algorithms into Closed-Loop Systems

Disclosed herein are methods, kits, systems, and devices incorporating algorithms for exercise guidance and instruction specific to diabetes relief and management into closed-loop or artificial pancreas systems. Such closed-loop systems include a device configured to monitor glucose levels and a device configured to deliver a compound to a subject. The loop begins with assessment of glucose levels in the subject. This assessment, if measured to be outside of a pre-determined range, is followed by transmission of a notification by the glucose monitoring device to the compound delivery device. This notification is followed by adjustment of the rate of compound delivery based upon the measured glucose level. The loop is closed by subsequent measurement of glucose levels by the glucose monitoring device.

A glucose monitoring device can include continuous glucose monitoring (CGM) devices or non-continuous glucose monitoring devices, for example, blood glucose meters (BGM). A CGM device can be a Bluetooth®-enabled device that electronically transmits glucose monitoring data from a glucose sensing device to a telecommunications device.

In some embodiments, the disclosure provides methods for adjusting the interaction of the components of a closed-loop system based upon an exercise recommendation. In some embodiments, the rate of insulin delivery is decreased based upon the exercise recommendation. In some embodiments, the rate of insulin delivery is increased based upon the exercise recommendation. In some embodiments, the rate of glucagon delivery is decreased based upon the exercise recommendation. In some embodiments, the rate of glucagon delivery is increased based upon the exercise recommendation.

Figure 3:
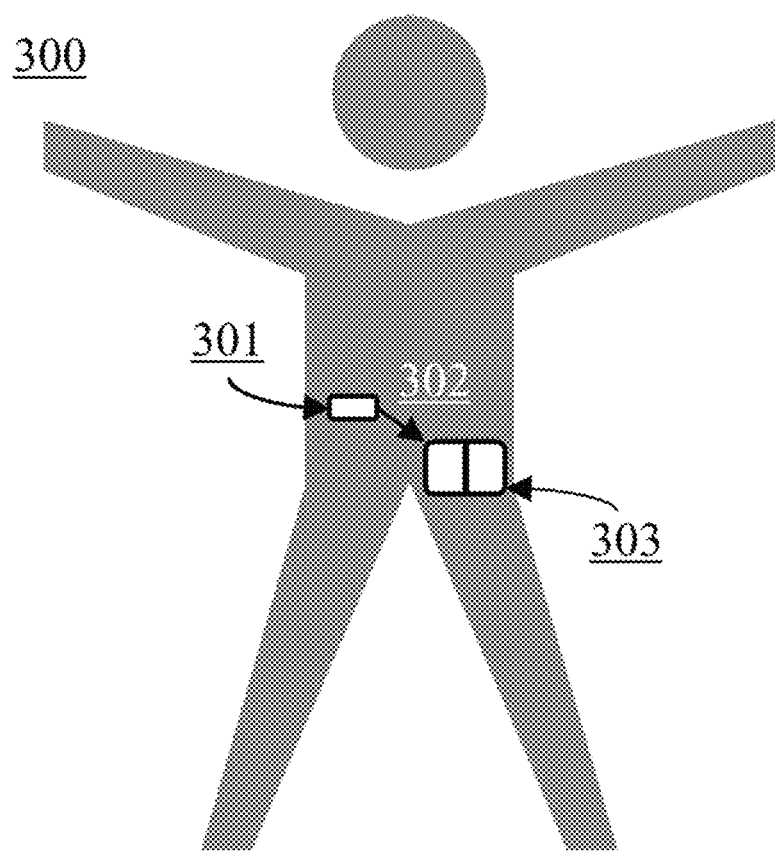
FIG. 3 illustrates a closed-loop system for insulin delivery to a subject.

FIG. 3 illustrates an embodiment of a closed-loop system 300 of the disclosure. The closed-loop system 300 comprises a continuous glucose monitor 301. When the continuous glucose monitor 301 measures a glucose value outside of a pre-determined range, the continuous glucose monitor 301 transmits a notification 302 to an insulin pump 303. The insulin pump 303 incorporates information relating to the exercise algorithms disclosed herein to adjust the insulin rate to return the glucose value to within an acceptable range based upon the calculated impact of the exercise activity on the glucose value. For example, if an exercise activity that would lower the blood glucose level, such as moderately paced hiking, was suggested by the algorithm, the closed-loop system 300 would account for this exercise activity to deliver a reduced rate of insulin to the subject.

Figure 4:
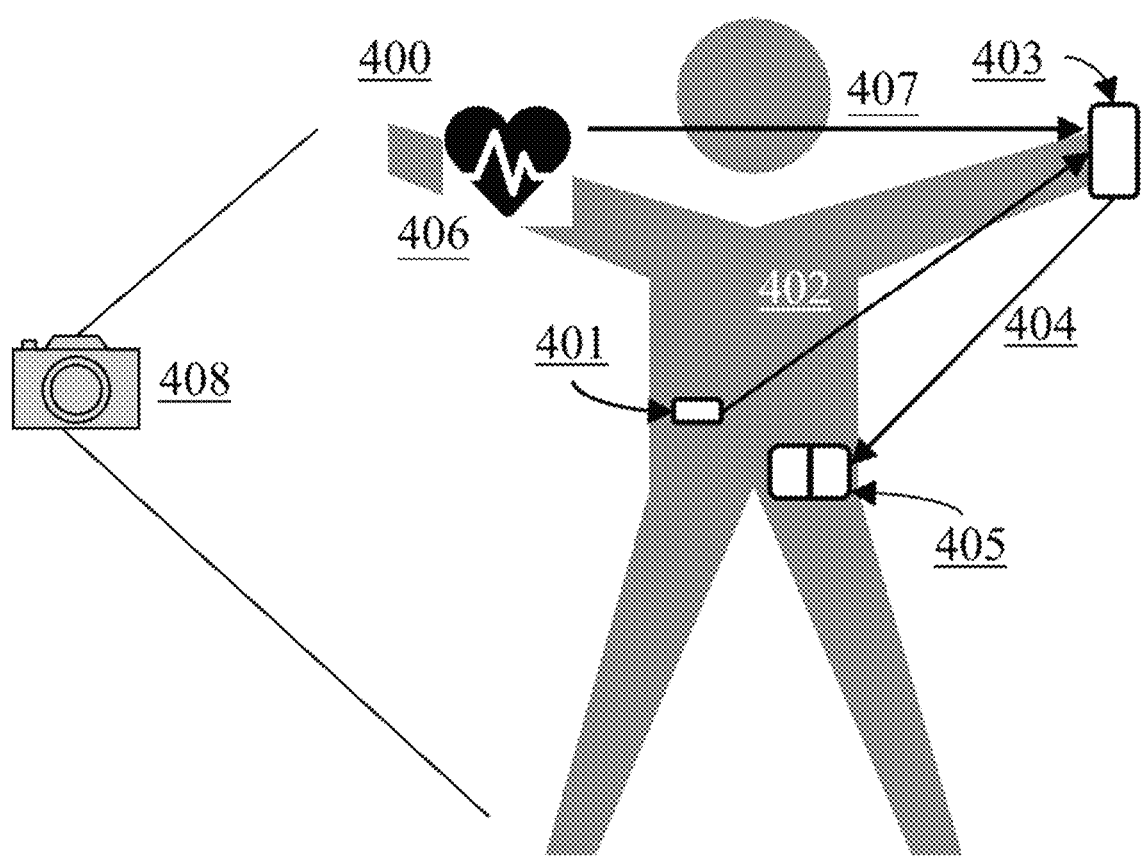
FIG. 4 illustrates a closed-loop system for insulin delivery to a subject.

FIG. 4 illustrates an embodiment of a closed-loop system 400 of the disclosure. The closed-loop system 400 comprises a continuous glucose monitor 401. When the continuous glucose monitor 401 measures a glucose value outside of a pre-determined range, the continuous glucose monitor 401 transmits a notification 402 to a telecommunications device with a processor, such as a telecommunications device 403.

The telecommunications device 403 receives the notification 402 and incorporates the exercise algorithms disclosed herein to provide an instruction 404 to a dual insulin/glucagon pump 405. The dual insulin/glucagon pump 405 alters the rate of insulin and glucagon delivery to return the glucose value to within an acceptable range based upon the calculated impact of the exercise activity on the glucose value.

A heart rate monitor 406 is also in communication with telecommunications device 403. The heart rate monitor 406 can detect the subject's heart rate prior to, during, and after exercise, and communicate 407 the heart rate to telecommunications device 403. The heart rate that is communicated to telecommunications device 403 can influence the determination of other important factors, including the type of exercise instruction given to the subject, the dose of insulin to administer, the dose of glucagon to administer, whether to warn the subject of an unsafe circumstance, whether to advise the subject to consume a source of carbohydrates, or whether to terminate exercise. An external camera 408 record the subject's motions during exercise to provide a real-time camera feed. External cameras can be used to capture the user's image for video production, broadcast, image analysis, or uni-directional and bi-directional communication. Image analysis can refer to the analysis of user images captured by cameras using automated assessment tools, screened and interpreted using human experts and/or artificial intelligence to identify a broad range of physiological, behavioral, or environmental patterns. Non-limiting examples of image patterns include changes in the user's facial complexion, body posture, facial expression, respiration, perspiration, body temperature, and performance of correct or incorrect movements.

For example, if an exercise activity that would raise the blood glucose level or alter heart rate, such as heavy weightlifting, was suggested by the algorithm, the closed-loop system 400 would account for this exercise activity to deliver an increased rate of insulin and decreased rate of glucagon to the subject.

In some embodiments, devices utilizing algorithms of the disclosure communicate instructions to, or receive instructions from, other devices as a component of a kit or system of the disclosure. All communications can be performed as disclosed herein, in the reverse, or in both directions.

In some embodiments, a glucose monitoring device, utilizing an algorithm of the disclosure, communicates an instruction to an insulin delivery device to administer insulin. In some embodiments, a glucose monitoring device, utilizing an algorithm of the disclosure, communicates an instruction to a glucagon delivery device to administer glucagon.

In some embodiments, a glucose monitoring device, utilizing an algorithm of the disclosure, communicates an instruction to a telecommunications device, which communicates the instruction to an insulin delivery device to administer insulin. In some embodiments, a glucose monitoring device, utilizing an algorithm of the disclosure, communicates an instruction to a telecommunications device, which communicates the instruction to a glucagon delivery device to administer glucagon. In some embodiments, a glucose monitoring device, utilizing an algorithm of the disclosure, communicates an instruction to a telecommunications device, which communicates the instruction to an insulin delivery device, which communicates the instruction to a glucagon delivery device to administer glucagon. In some embodiments, a glucose monitoring device, utilizing an algorithm of the disclosure, communicates an instruction to a telecommunications device, which communicates the instruction to a glucagon delivery device, which communicates the instruction to an insulin delivery device to administer insulin.

In some embodiments, a glucose monitoring device, utilizing an algorithm of the disclosure, communicates an instruction to an insulin delivery device, which communicates the instruction to a glucagon delivery device to administer glucagon. In some embodiments, a glucose monitoring device, utilizing an algorithm of the disclosure, communicates an instruction to a glucagon delivery device, which communicates the instruction to an insulin delivery device to administer insulin. In some embodiments, a glucose monitoring device, utilizing an algorithm of the disclosure, communicates an instruction to an insulin delivery device, which communicates the instruction to a telecommunications device, which communicates the instruction to a glucagon delivery device to administer glucagon. In some embodiments, a glucose monitoring device, utilizing an algorithm of the disclosure, communicates an instruction to a glucagon delivery device, which communicates the instruction to a telecommunications device, which communicates the instruction to an insulin delivery device to administer insulin.

In some embodiments, a telecommunications device, utilizing an algorithm of the disclosure, communicates an instruction to an insulin delivery device to administer insulin. In some embodiments, a telecommunications device, utilizing an algorithm of the disclosure, communicates an instruction to a glucagon delivery device to administer glucagon. In some embodiments, a telecommunications device, utilizing an algorithm of the disclosure, communicates an instruction to a glucose monitoring device to measure a glucose level. In some embodiments, a telecommunications device, utilizing an algorithm of the disclosure, communicates an instruction to a glucose monitoring device, which communicates the instruction to an insulin delivery device to administer insulin. In some embodiments, a telecommunications device, utilizing an algorithm of the disclosure, communicates an instruction to a glucose monitoring device, which communicates the instruction to a glucagon delivery device to administer glucagon.

In some embodiments, a telecommunications device, utilizing an algorithm of the disclosure, communicates an instruction to a glucose monitoring device, which communicates the instruction to an insulin delivery device, which communicates the instruction to a glucagon delivery device to administer glucagon. In some embodiments, a telecommunications device, utilizing an algorithm of the disclosure, communicates an instruction to a glucose monitoring device, which communicates the instruction to a glucagon delivery device, which communicates the instruction to an insulin delivery device to administer insulin. In some embodiments, a telecommunications device, utilizing an algorithm of the disclosure, communicates an instruction to an insulin delivery device, which communicates the instruction to a glucose monitoring device, which communicates the instruction to a glucagon delivery device to administer glucagon. In some embodiments, a telecommunications device, utilizing an algorithm of the disclosure, communicates an instruction to a glucagon delivery device, which communicates the instruction to a glucose monitoring device, which communicates the instruction to an insulin delivery device to administer insulin.

In some embodiments, a telecommunications device, utilizing an algorithm of the disclosure, communicates an instruction to a glucagon delivery device, which communicates the instruction to a glucose monitoring device to measure a glucose level. In some embodiments, a telecommunications device, utilizing an algorithm of the disclosure, communicates an instruction to an insulin delivery device, which communicates the instruction to a glucose monitoring device to measure a glucose level. In some embodiments, a telecommunications device, utilizing an algorithm of the disclosure, communicates an instruction to a glucagon delivery device, which communicates the instruction to an insulin delivery device, which communicates the instruction to a glucose monitoring device to measure a glucose level. In some embodiments, a telecommunications device, utilizing an algorithm of the disclosure, communicates an instruction to an insulin delivery device, which communicates the instruction to a glucagon delivery device, which communicates the instruction to a glucose monitoring device to measure a glucose level.

In some embodiments, a glucagon delivery device, utilizing an algorithm of the disclosure, communicates an instruction to an insulin delivery device to administer insulin. In some embodiments, a glucagon delivery device, utilizing an algorithm of the disclosure, communicates an instruction to a glucose monitoring device to measure a glucose level.

In some embodiments, a glucagon delivery device, utilizing an algorithm of the disclosure, communicates an instruction to a telecommunications device, which communicates the instruction to an insulin delivery device to administer insulin. In some embodiments, a glucagon delivery device, utilizing an algorithm of the disclosure, communicates an instruction to a telecommunications device, which communicates the instruction to a glucose monitoring device to measure a glucose level. In some embodiments, a glucagon delivery device, utilizing an algorithm of the disclosure, communicates an instruction to a telecommunications device, which communicates the instruction to an insulin delivery device, which communicates the instruction to a glucose monitoring device to measure a glucose level. In some embodiments, a glucagon delivery device, utilizing an algorithm of the disclosure, communicates an instruction to a telecommunications device, which communicates the instruction to a glucose monitoring device, which communicates the instruction to an insulin delivery device to administer insulin.

In some embodiments, a glucagon delivery device, utilizing an algorithm of the disclosure, communicates an instruction to an insulin delivery device, which communicates the instruction to a glucose monitoring device to measure a glucose level. In some embodiments, a glucagon delivery device, utilizing an algorithm of the disclosure, communicates an instruction to a glucose monitoring device, which communicates the instruction to an insulin delivery device to administer insulin. In some embodiments, a glucagon delivery device, utilizing an algorithm of the disclosure, communicates an instruction to an insulin delivery device, which communicates the instruction to a telecommunications device, which communicates the instruction to a glucose monitoring device to measure a glucose level. In some embodiments, a glucagon delivery device, utilizing an algorithm of the disclosure, communicates an instruction to a glucose monitoring device, which communicates the instruction to a telecommunications device, which communicates the instruction to an insulin delivery device to administer insulin.

In some embodiments, a glucagon delivery device, utilizing an algorithm of the disclosure, communicates an instruction to an insulin delivery device to administer insulin. In some embodiments, a glucagon delivery device, utilizing an algorithm of the disclosure, communicates an instruction to a glucose monitoring device to measure a glucose level.

In some embodiments, a glucagon delivery device, utilizing an algorithm of the disclosure, communicates an instruction to a telecommunications device, which communicates the instruction to an insulin delivery device to administer insulin. In some embodiments, a glucagon delivery device, utilizing an algorithm of the disclosure, communicates an instruction to a telecommunications device, which communicates the instruction to a glucose monitoring device to measure a glucose level. In some embodiments, a glucagon delivery device, utilizing an algorithm of the disclosure, communicates an instruction to a telecommunications device, which communicates the instruction to an insulin delivery device, which communicates the instruction to a glucose monitoring device to measure a glucose level. In some embodiments, a glucagon delivery device, utilizing an algorithm of the disclosure, communicates an instruction to a telecommunications device, which communicates the instruction to a glucose monitoring device, which communicates the instruction to an insulin delivery device to administer insulin.

In some embodiments, a glucagon delivery device, utilizing an algorithm of the disclosure, communicates an instruction to an insulin delivery device, which communicates the instruction to a glucose monitoring device to measure a glucose level. In some embodiments, a glucagon delivery device, utilizing an algorithm of the disclosure, communicates an instruction to a glucose monitoring device, which communicates the instruction to an insulin delivery device to administer insulin. In some embodiments, a glucagon delivery device, utilizing an algorithm of the disclosure, communicates an instruction to an insulin delivery device, which communicates the instruction to a telecommunications device, which communicates the instruction to a glucose monitoring device to measure a glucose level. In some embodiments, a glucagon delivery device, utilizing an algorithm of the disclosure, communicates an instruction to a glucose monitoring device, which communicates the instruction to a telecommunications device, which communicates the instruction to an insulin delivery device to administer insulin.

In some embodiments, an insulin delivery device, utilizing an algorithm of the disclosure, communicates an instruction to a glucagon delivery device to administer glucagon. In some embodiments, an insulin delivery device, utilizing an algorithm of the disclosure, communicates an instruction to a glucose monitoring device to measure a glucose level.

In some embodiments, an insulin delivery device, utilizing an algorithm of the disclosure, communicates an instruction to a telecommunications device, which communicates the instruction to a glucagon delivery device to administer glucagon. In some embodiments, an insulin delivery device, utilizing an algorithm of the disclosure, communicates an instruction to a telecommunications device, which communicates the instruction to a glucose monitoring device to measure a glucose level. In some embodiments, an insulin delivery device, utilizing an algorithm of the disclosure, communicates an instruction to a telecommunications device, which communicates the instruction to a glucagon delivery device, which communicates the instruction to a glucose monitoring device to measure a glucose level. In some embodiments, an insulin delivery device, utilizing an algorithm of the disclosure, communicates an instruction to a telecommunications device, which communicates the instruction to a glucose monitoring device, which communicates the instruction to a glucagon delivery device to administer glucagon.

In some embodiments, an insulin delivery device, utilizing an algorithm of the disclosure, communicates an instruction to a glucagon delivery device, which communicates the instruction to a glucose monitoring device to measure a glucose level. In some embodiments, an insulin delivery device, utilizing an algorithm of the disclosure, communicates an instruction to a glucose monitoring device, which communicates the instruction to a glucagon delivery device to administer glucagon. In some embodiments, an insulin delivery device, utilizing an algorithm of the disclosure, communicates an instruction to a glucagon delivery device, which communicates the instruction to a telecommunications device, which communicates the instruction to a glucose monitoring device to measure a glucose level. In some embodiments, an insulin delivery device, utilizing an algorithm of the disclosure, communicates an instruction to a glucose monitoring device, which communicates the instruction to a telecommunications device, which communicates the instruction to a glucagon delivery device to administer glucagon.

Figure 5:
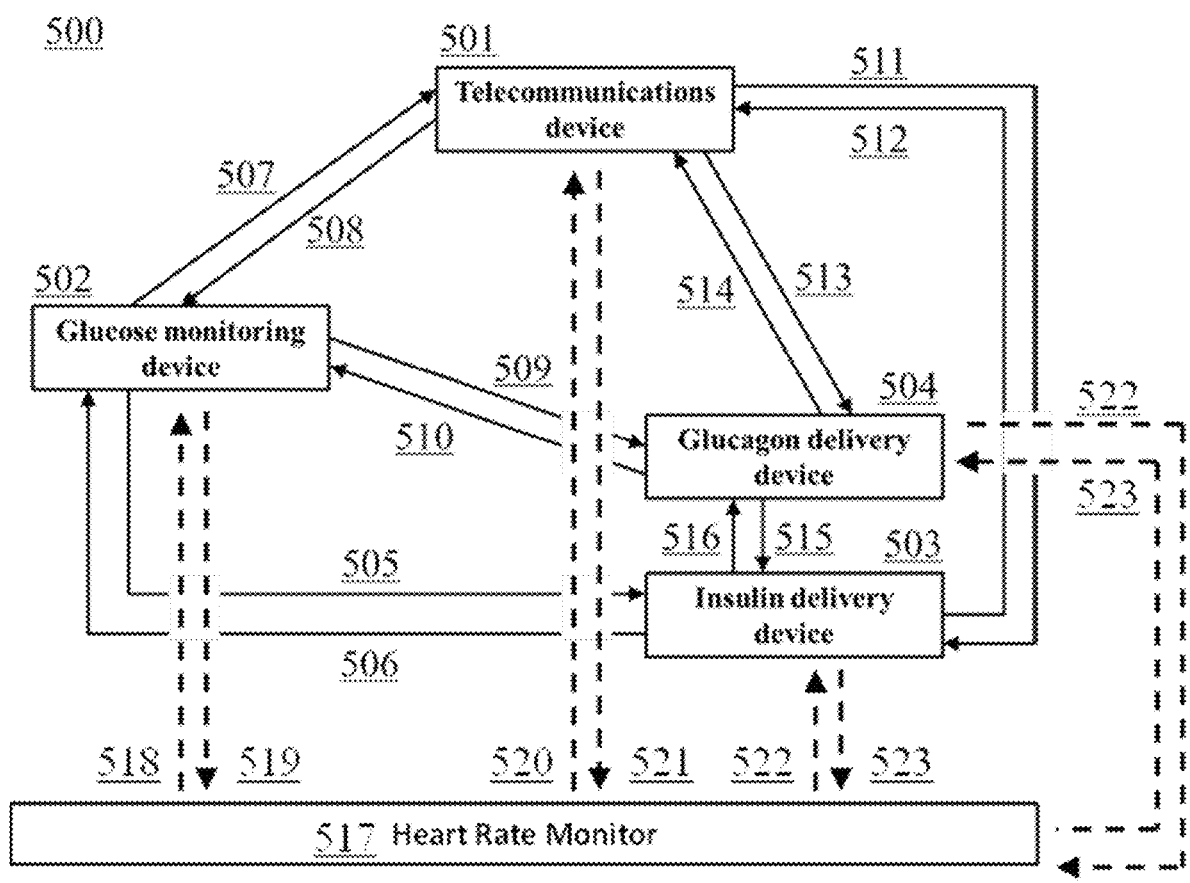
FIG. 5 depicts communications among components of a closed-loop system.

FIG. 5 depicts communications among components of a closed-loop system 500. The closed-loop system 500 includes a telecommunications device 501, a glucose monitoring device 502, an insulin delivery device 503, and a glucagon delivery device 504. The glucose monitoring device 502, utilizing an algorithm of the disclosure, can transmit an instruction 505 to the insulin delivery device 503, and the insulin delivery device 503, utilizing an algorithm of the disclosure, can transmit an instruction 506 to the glucose monitoring device 502. The glucose monitoring device 502 can transmit an instruction 507, utilizing an algorithm of the disclosure, to the telecommunications device 501, and the telecommunications device 501, utilizing an algorithm of the disclosure, can transmit an instruction 508 to the glucose monitoring device 502. The glucose monitoring device 502 can transmit an instruction 509, utilizing an algorithm of the disclosure, to the glucagon delivery device 504, and the glucagon delivery device 504, utilizing an algorithm of the disclosure, can transmit an instruction 510 to the glucose monitoring device 502. The telecommunications device 501, utilizing an algorithm of the disclosure, can transmit an instruction 511 to the insulin delivery device 503, and the insulin delivery device 503, utilizing an algorithm of the disclosure, can transmit an instruction 512 to the telecommunications device 501. The telecommunications device 501 can transmit an instruction 513, utilizing an algorithm of the disclosure, to the glucagon delivery device 504, and the glucagon delivery device 504, utilizing an algorithm of the disclosure, can transmit an instruction 514 to the telecommunications device 501. The insulin delivery device 503 can transmit an instruction 515, utilizing an algorithm of the disclosure, to the glucagon delivery device 504, and the glucagon delivery device 504, utilizing an algorithm of the disclosure, can transmit an instruction 516 to the insulin delivery device 503. Any or all of the components of the system can be present in a single housing. Any or all of the components, or the single housing can be implantable or implanted in the subject.

FIG. 5 further depicts a heart rate monitor 517, connected to the other components by dashed lines. The heart rate monitor 517, utilizing an algorithm of the disclosure, can transmit an instruction 522 to the insulin delivery device 503, and the insulin delivery device 503, utilizing an algorithm of the disclosure, can transmit an instruction 523 to the heart rate monitor 517. The heart rate monitor 517 can transmit an instruction 520, utilizing an algorithm of the disclosure, to the telecommunications device 501, and the telecommunications device 501, utilizing an algorithm of the disclosure, can transmit an instruction 521 to the heart rate monitor 517. The heart rate monitor 517 can transmit an instruction 523, utilizing an algorithm of the disclosure, to the glucagon delivery device 504, and the glucagon delivery device 504, utilizing an algorithm of the disclosure, can transmit an instruction 522 to the heart rate monitor 517. The heart rate monitor 517 can transmit an instruction 518, utilizing an algorithm of the disclosure, to the glucose monitoring device 502, and the glucose monitoring device 502, utilizing an algorithm of the disclosure, can transmit an instruction 519 to the heart rate monitor 517. Any or all of the components of the system can be present in a single housing. Any or all of the components, or the single housing can be implantable or implanted in the subject.

Computer Processing for Diabetes Exercise Algorithms

Figure 6:
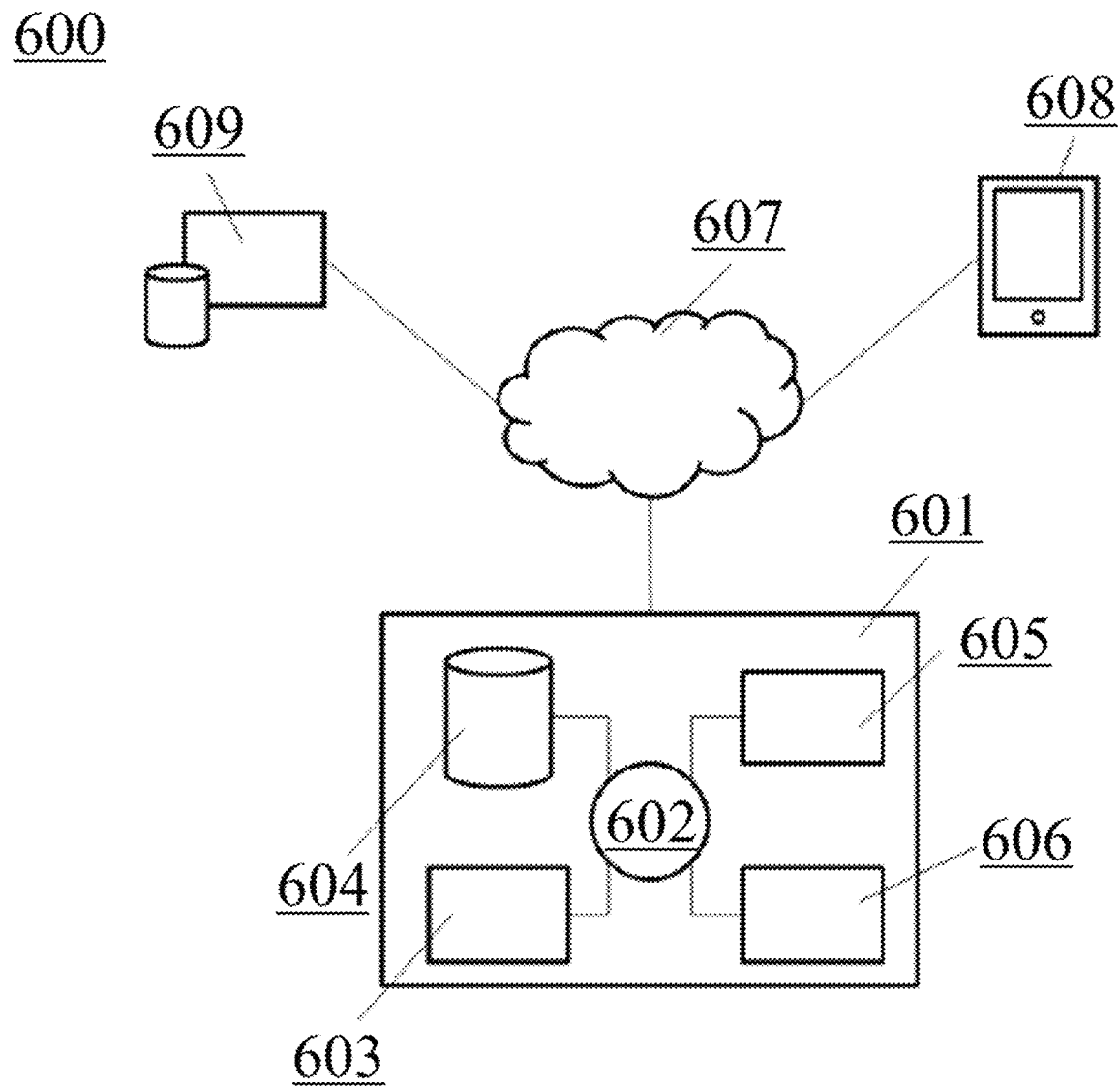
FIG. 6 illustrates a computer system for facilitating methods, systems, kits, or devices of the disclosure.

FIG. 6 shows a computer system 600 programmed or otherwise configured to allow a subject to monitor a glucose level and transmit a reading of the glucose level; to instruct administration of hormone to the subject; to instruct a state of physical exercise through an exercise instructional video; to display a reading of a biometric data of the subject; or to instruct an exercise instructional video to stop and to present an alternative exercise instructional video, in accordance with various embodiments of the present disclosure. The system 600 includes a computer server ("server") 601 that is programmed to implement methods disclosed herein. The server 601 includes a central processing unit 602, which can be a single core or multi core processor, or a plurality of processors for parallel processing. The server 601 also includes: memory 603, such as random-access memory, read-only memory, and flash memory; electronic storage unit 604, such as a hard disk; communication interface 605, such as a network adapter, for communicating with one or more other systems; and peripheral devices 606, such as cache, other memory, data storage, and electronic display adapters. The memory 603, storage unit 604, interface 605 and peripheral devices 606 are in communication with the CPU 602 through a communication bus, such as a motherboard. The storage unit 604 can be a data storage unit or data repository for storing data. The server 601 can be operatively coupled to a computer network (hereinafter "network") 607 with the aid of the communication interface 605. The network 607 can be the Internet, an internet or extranet, or an intranet or extranet that is in communication with the Internet. The network 607 in some cases is a telecommunications network or data network. The network 607 can include one or more computer servers, which can allow distributed computing, such as cloud computing. The network 607, in some cases with the aid of the server 601, can implement a peer-to-peer network, which can allow devices coupled to the server 601 to behave as a client or an independent server.

The storage unit 604 can store files, such as files related to biometric data, glucose level readings, basal and adjusted rates of hormone administration, body weight, time of day of physical exercise, type of physical exercise, and duration of physical exercise. The storage unit 604 can store media items, such as exercise instruction videos of the disclosure. The storage unit 604 can store subject data, such as biometric data, glucose level readings, basal and adjusted rates of hormone administration, body weight, time of day of physical exercise, type of physical exercise, and duration of physical exercise at various points in time. The server 601 in some cases can include one or more additional data storage units that are external to the server 601, such as located on a remote server that is in communication with the server 601 through an intranet or the Internet. The storage unit 604 can store videos that provide exercise instruction, as well as items included in videos that provide exercise instruction, such as real-time biometric data collected during the performance of physical exercise with the video.

The server 601 can communicate with one or more remote computer systems through the network 607. In some embodiments, the server 601 is in communication with a first computer system 608 and a second computer system 609 that are located remotely with respect to the server 501. The first computer system 608 can be the computer system of a first subject, and the second computer system 609 can be that of a second subject, such as a personal trainer or third-party healthcare provider, such as a doctor, a nurse, or a dietician. The first computer system 608 and second computer system 609 can be, for example, personal computers, such as a portable PC; slate and tablet PC, such as Apple® iPad and Samsung® Galaxy Tab; telephones; smartphones, such as Apple® iPhone, Android-enabled device, Google® Pixel, Windows® Phone, and Blackberry®; smart watches, such as Apple® Watch; smart glasses, such as Google® Glass; or personal digital assistants. The first or second subject can access the server 601 via the network 607 to view or manage an exercise instruction video.

In some situations, the system 600 includes a single server 601. In other situations, the system 600 includes multiple servers in communication with one another through an intranet or the Internet. The server 601 can be adapted to store subject profile information, such as, for example, a name, physical address, email address, telephone number, instant messaging (IM) handle, educational information, work information, social likes or dislikes and historical information, such as information that can relate to the progress of a subject in exercise instruction, and other information of potential relevance to the subject. Such profile information can be stored on the storage unit 604 of the server 601.

Methods as described herein can be implemented by way of a machine- or computer-executable code or software stored on an electronic storage location of the server 601, such as, for example, on the memory 603 or electronic storage unit 604. During use, the code can be executed by the processor 602. In some cases, the code can be retrieved from the storage unit 604 and stored on the memory 603 for ready access by the processor 602, for example, computer-executable code for hormone administration while a subject is in a state of physical rest prior to the subject being in a state of physical exercise. In some situations, the electronic storage unit 604 can be precluded, and machine-executable instructions are stored on memory 603. Alternatively, the code can be executed on the second computer system 609. The code can be pre-compiled and configured for use with a processor adapted to execute the code, or can be compiled during runtime. The code can be supplied in a programming language that can be selected to allow the code to execute in a precompiled or as-compiled fashion.

All or portions of the software can at times be communicated through the Internet or various other telecommunications networks. Such communications can support loading of the software from one computer or processor into another, for example, from a management server or host computer into the computer platform of an application server. Another type of media that can bear the software elements includes optical, electrical and electromagnetic waves, such as those used across physical interfaces between local devices, through wired and optical landline networks and over various air-links. The physical elements that carry such waves, such as wired or wireless links, or optical links, also can be considered as media bearing the software.

A machine-readable medium, incorporating computer-executable code, can take many forms, including a tangible storage medium, a carrier wave medium, and physical transmission medium. Non-limiting examples of non-volatile storage media include optical disks and magnetic disks, such as any of the storage devices in any computer, such as can be used to implement the databases of FIG. 6. Volatile storage media include dynamic memory, such as a main memory of such a computer platform. Tangible transmission media include coaxial cables, copper wire and fiber optics, including wires that comprise a bus within a computer system. Carrier-wave transmission media can take the form of electric or electromagnetic signals, or acoustic or light waves such as those generated during radio frequency (RF) and infrared (IR) data communications.

Common forms of computer-readable media include: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, and any other medium from which a computer can read programming code or data. Many of these forms of computer readable media can be involved in carrying one or more sequences of one or more instructions to a processor for execution.

The server 601 can be configured for: data mining; extract, transform and load (ETL); or spidering operations, including Web Spidering where the system retrieves data from remote systems over a network and access an Application Programming Interface or parses the resulting markup, which can permit the system to load information from a raw data source or mined data into a data warehouse. The data warehouse can be configured for use with a business intelligence system, such as Microstrategy® and Business Objects®. The system can include a data mining module adapted to search for media items in various source locations, such as email accounts and various network sources, such as social networking accounts, such as Facebook®, Foursquare®, Google+®, and LinkedIn®, or on publisher sites, such as weblogs.

An exercise instruction video can be presented to a subject on a subject interface (UI) of an electronic device of the subject. Non-limiting examples of UIs include a graphical subject interface (GUI) and web-based subject interface. A GUI can allow a subject to access an exercise instruction video. The GUI can allow a subject to edit the exercise instruction video, such as upload items to the exercise instruction video to display to other subjects in a manner selected by the subject. The UI, such as GUI, can be provided on a display of an electronic device of the subject. The display can be a capacitive or resistive touch display, or a head-mountable display, such as a Google® Glass. Such displays can be used with other systems and methods of the disclosure.

Methods of the disclosure can be facilitated with the aid of applications, or apps, that can be installed on an electronic device of the subject. An app can include a GUI on a display of the electronic device of the subject. The app can be programmed or otherwise configured to perform various functions of the system, such as, for example, permitting a subject to manage, such as create and edit, an exercise instructional program. GUIs of apps can display on an electronic device of the subject. Non-limiting examples of electronic devices include computers, televisions, smartphones, tablets, and smart watches. The electronic device can include, for example, a passive screen, a capacitive touch screen, or a resistive touch screen. The electronic device can include a network interface and a browser that allows the subject to access various sites or locations, such as web sites, on an intranet or the Internet. The app is configured to allow the mobile device to communicate with a server, such as the server 601.

Diabetes Exercise Algorithm Integration into External Devices

Methods, systems, kits, and devices of the disclosure can incorporate diabetes exercise algorithms into external devices. Non-limiting examples of external devices that can incorporate diabetes exercise algorithms include external insulin delivery devices, external glucagon delivery devices, and external glucose monitoring devices.

In some embodiments, the subject receives or is administered the dose of hormone through an external hormone delivery device in contact with the subject. In some embodiments, the external hormone delivery device is configured to pump hormone. In some embodiments, the external hormone delivery device is configured to inject hormone. In some embodiments, the external insulin delivery device and external glucagon delivery device are contained within a common housing.

In some embodiments, a hormone pump is capable of automatic injection a fixed amount of hormone at defined rates or time points by driving a piston in a state where an injection needle is inserted into a body fat region of the abdomen of the subject. In the pump, an injector is mounted on a side of a box-type housing in a longitudinal direction, and a push member is mounted at a lower section of the injector to drive the injector. The injector includes a cylindrical syringe for containing hormone therein and a piston inserted into the syringe for pushing the hormone through a tube. A disk-type push member is mounted on the lower end of the piston, and a female screw is formed at the center of the push member.

A motor and a power supply, which has a number of deceleration gear lines for decelerating a rotational speed of the motor, are mounted on the lower portion of the box-type housing, and a rotary shaft is mounted on a final gear of the deceleration gear lines. The rotary shaft has a male screw of the circumferential surface thereof, and the male screw is coupled with the female screw of the push member. As a result, the push member advances according to the rotation of the rotary shaft, the piston advances inside the syringe, and thereby, the hormone corresponding to an advanced amount of the piston is injected into the subject through the tube and an injection needle. In some embodiments, the hormone pump includes a cover to allow the injector to be drawn to the outside of the box-type housing when the hormone is loaded into the pump. In some embodiments, the hormone pump includes a connector for connecting the tube to the syringe. In some embodiments, the hormone pump includes a sealing cap for preventing penetration of moisture into the power supply.

In some embodiments, the subject measures a glucose level of the subject through an external glucose monitoring device in contact with the subject. In some embodiments, the external glucose monitoring device is a glucose meter device. In some embodiments, the external glucose monitoring device is a continuous glucose monitoring device. In some embodiments, the continuous glucose monitoring device is implanted underneath the skin.

Two major classes of glucose monitoring devices are used by subjects: (1) non-continuous or single-point glucose monitoring devices, such as blood glucose meters and blood glucose test strips; and (2) continuous glucose monitoring devices. Non-continuous glucose monitoring devices consist of meters and test strips that require blood samples to be drawn from fingertips, forearms, or legs. These glucose monitoring devices rely on lancing and manipulation of the blood draw site.

Continuous glucose monitoring devices are implanted, for example, subcutaneously, and measure glucose levels in the interstitial fluid at various time points throughout the day, to show trends in glucose levels over a period of time. As these devices are implanted, use of a continuous glucose monitoring devices requires the assistance of a health care professional. Continuous glucose monitoring devices also require frequent, for example, daily calibration using blood glucose results obtained from non-continuous glucose monitoring devices. This repeated calibration is helpful for maintaining sensor accuracy and sensitivity.

In some embodiments, a continuous glucose monitoring device has an array of hollow microneedles or other tissue piercing elements extending through the stratum corneum of a subject into the interstitial fluid beneath the stratum corneum. The microneedles in the array are hollow and have open distal ends, and their interiors communicate with a sensing area within a sensor channel. The sensing area is therefore in fluid communication with interstitial fluid through the microneedle array. The sensing area and the microneedle array are pre-filled with sensing fluid prior to the first use of the device. Thus, when the device is implanted into the skin of the subject and the microneedles pierce the stratum corneum of the skin, substantially no net fluid transfers from the interstitial fluid into the microneedles, but instead glucose diffuses from the interstitial fluid into the sensing fluid within the needles.

Disposed above and in fluid communication with sensor channel is a glucose sensor. In some embodiments, the glucose sensor is an electrochemical glucose sensor that generates an electrical signal, such as current, voltage and charge, whose value depends on the concentration of glucose in the fluid within the sensing area. A sensor electronics element receives the voltage signal from the glucose sensor. In some embodiments, the sensor electronics element uses the sensed signal to compute a glucose concentration and display it. In other embodiments, sensor electronics element transmits the sensed signal, or information derived from the sensed signal, to a remote device, such as through wireless communication. The continuous glucose monitoring device is held in place on the skin by one or more adhesive pads.

In some embodiments, the continuous glucose monitoring device has a built-in sensor calibration system. A reservoir comprises a sensing fluid with, for example, a glucose concentration from about 1 mg/dL to about 400 mg/dL. In some embodiments, the glucose concentration in the sensing fluid is selected to be below the glucose sensing range of the sensor. The sensing fluid can comprise buffers, preservatives, or other substances in addition to glucose. Upon actuation of a manual or automatic pump, plunger or other actuator, sensing fluid is forced from the reservoir through a first check valve, such as a flap valve, into a sensing channel. The sensing fluid within the sensing channel is forced through a second check valve, such as a flap valve, into a waste reservoir. Check valves or similar gating systems are used to reduce the likelihood of contamination. Because the fresh sensing fluid has a known glucose concentration, the sensor is calibrated at this value to set a baseline. After calibration, the sensing fluid in the sensing channel remains stationary, and glucose from the interstitial fluid diffuses through microneedles into the sensing area. Changes in the glucose concentration over time reflect differences between the calibration glucose concentration of the sensing fluid in the reservoir and the glucose concentration of the interstitial fluid, which can be correlated with the actual blood glucose concentration of the subject. Because of possible degradation of the sensor or loss of sensor sensitivity over time, the continuous glucose monitoring device can be periodically recalibrated by manual or automatic operation of the actuator to send fresh sensing fluid from the reservoir into the sensing area.

In some embodiments, the glucose monitoring device can measure other analytes, such as electrolytes, for example, sodium, calcium, magnesium, zinc, iron, and potassium. In some embodiments, the glucose monitoring device can use any suitable sensor including, for example, an electrochemical sensor and an optical sensor.

Virtual Health Assistant

Integrated analysis of user biometrics can be used to promote positive lifestyle changes for effective, long-term health management. Systems and methods disclosed herein can be integrated with a virtual health assistant powered by artificial intelligence and machine learning. Similar to digital trainers disclosed herein, virtual assistants can receive and process user biometric data to provide personalized health guidance and feedback in real-time. A virtual health assistant can receive and analyze user biometric data using artificial intelligence platforms including, for example, machine learning, natural language processing, and speech recognition.

A virtual health assistant can provide step-by-step guidance, for example, for a newly diagnosed diabetes patient who can benefit from individualized guidance with adapting to new lifestyle changes. A virtual health assistant can provide notifications or reminders to complete diabetes management tasks based on a user's personalized routine in real-time. Health management tasks can include, for example, completing an exercise routine, administering a medication, administering insulin, administering glycogen, monitoring blood glucose level, monitoring blood pressure, and consuming a food or beverage.

A virtual health assistant can provide 24/7, round-the-clock access to a lifestyle coach to enhance health management. The virtual assistant can track user progress and maintain a personalized daily schedule of health management tasks. The virtual assistant can provide continuous virtual health check-ups, for example, by monitoring user biometrics in real-time. Progress tracking can include logging compliance with a scheduled regimen by time-stamping and date-stamping completion of a task by a user in real-time. Progress tracking can further include information about adequacy of user performance of an exercise, for example, based on user comfort and challenge level before, after, and during an exercise regimen. User performance can be determined by real-time biometrics. For example, real-time detection of heart rate and pulmonary metrics during user performance of an exercise can be determining factors of exercise performance, as well as the fitness level of the user. Progress tracking can further include recordation of user biometrics before, after, and during an exercise regimen. User biometric information can be processed in real-time to provide continuous improvements to the user's personalized health regimen.

In some embodiments, the virtual health assistant can offer provide lifestyle recommendations to improve the progress of the user on a daily, weekly, monthly, or yearly basis. The virtual assistant can recommend lifestyle recommendations in real-time based on changes in user biometrics over time. Lifestyle recommendations can include, for example, modifying sleeping habits, exercise habits, diet, medication dosage, and social media habits.

The system can also provide a communication medium between the user and a healthcare provider. For example, when a user biometrics is detected to be at a dangerous range, the system can notify a healthcare provider.

In some embodiments, the virtual health systems described herein can be integrated with other virtual assistant systems, for example, Amazon® Alexa, Apple® Siri, Google® Now, or Microsoft® Cortana.

Mental Health Assistant

Diabetic patients can be at a high risk for mental health issues including, for example, stress, depression, anxiety, and anger. Negative thoughts, feelings, beliefs, and attitudes can adversely affect the progress of diabetes management. Undiagnosed and untreated mental health issues can lead to unhealthy diabetes management habits, which can worsen diabetes prognosis and further exacerbate mental health issues. In some embodiments, a virtual health assistant described herein can monitor a user's mental state and provide psychological support to resolve or reduce the likelihood of mental health issues.

A user's mental state can be monitored by analysis of real-time user biometrics, for example, hormone levels, menstrual cycles, exercise patterns, sleeping habits, social media presence. In addition, the virtual health assistant can assess the psychological state of a user based on user response to mental health questionnaires. In some embodiments, the virtual health assistant can connect a user with a health care professional if determined to be necessary based on the assessment. For example, the virtual health assistant can provide a communication medium between a user and a health care professional.

For example, a virtual health assistant can provide guided meditation routines as an example mechanism for relieving stress and promoting healthy psychological state.

Dietary Health Assistant

Diet and nutrition are critical factors in effective diabetes management. For example, diabetic patients are recommended to monitor carbohydrate intake carefully to avoid adverse medical reactions due to sudden changes in glucose levels in response to food intake. The virtual health assistant program described herein can provide a mechanism for monitoring dietary habits of a user using multimedia devices and systems that monitor user biometrics. Thus, the system described herein provides a personalized nutritional guide for health and diet management.

For example, users can record or log daily food intake using the system described. User food intake can be recorded in the system by manual input by the user of descriptions, keywords, photographs, videos, social media, or other types of multimedia. The input can be time-stamped and date-stamped to associate the food intake to a specific time. Accordingly, the system can create a timeline of user food intake.

User food intake data can also be associated with one or more biometrics of the user in real-time before, during, and after intake of the food. For example, consumption of a high carbohydrate food by a user can lead to a rapid spike in blood glucose level in the user. Accordingly, the system can associate the metabolic effect of a food to a user based on changes to the user's biometrics following consumption of the food. Over time, the system can learn and predict future metabolic effects in a user in response to consumption of a particular food by the user.

In some embodiments, the user food metabolism data can be used to provide dietary recommendations to the user. For example, if the system detects that user consumption of a high carbohydrate containing food leads to a spike in glucose levels, the system can provide a future recommendation to the user to consume a lower carbohydrate containing food.

In some embodiments, the system can associate a food intake data with a user's schedule or calendar. For example, if the system detects that a user has a scheduled exercise, the system can recommend to the user prior to the scheduled exercise to consume a food due to the anticipated decrease in glucose level of the user during exercise. If the system detects that a user has a scheduled meal, the system can recommend to the user prior to the scheduled meal to administer insulin due to the anticipated increase in glucose level of the user during the meal. For example, if a user has a series of meetings that may intervene with predicted glucose levels, the system can recommend to the user to consume a snack at a pre-determined time to reduce the likelihood of a predicted reduction in glucose levels at a future time point. The pre-determined time can be predicted by the system based on historical monitoring of metabolic rates or real-time biometrics of the user.

In some embodiments, the system can associate a food intake data with a user's health goals. For example, a user can have a goal of losing weight over a period of time. The system can determine a feasible dietary regimen and eating schedule to meet the user's goal by analyzing real-time biometrics of the user and lifestyle habits of the user. For example, lifestyle habits can include dietary habits, dietary preferences, exercise habits, sleeping habits, work schedule, and hobbies. For example, for a user who typically consumes large meals a few times a day, the system can recommend eating smaller meals and more frequently. For example, if the system detects that a user has a scheduled vacation, the system can recommend to the user to take a walk or a jog to sightsee. The system can recommend a specific tourist route. For example, if the system detects that a user is dining at a specific restaurant, the system can recommend to the user specific food recommendations based on the nutritional facts of menu items at the restaurant. For example, the system can recommend choosing more healthful, nutrient-dense foods that promote weight loss or control glycemic levels.

Food multimedia received from the user can be analyzed and evaluated based on a food database that estimates nutritional content and caloric content based on portion size and nutritional facts. For example, the system can estimate carbohydrate content of a food to monitor the effect on the glucose level in the user after consumption of the food by the user. In some embodiments, the system can access nutritional facts of restaurant menus or grocery items from online databases.

In some embodiments, the system can predict the carbohydrate content of a food based on multimedia received from the user. For example, the user can upload a photograph or video of a food consumed or to be consumed by the user. The system can analyze the multimedia depiction of the food and determine nutritional content, for example, carbohydrate content.

Further, the system described herein can provide a nutritional rating of a food based on the predicted nutritional content. Based on historical biometric measurements of the user after consumption of the food or food having similar nutritional content, the system can further provide a nutritional rate of the food or provide a recommendation to the user whether or not to consume the food.

Improving Patient Adherence

Patient adherence to treatment regimens is a common issue among diabetes patients, which can make glycemic control difficult to attain. Inability to adhere to treatment recommendations increases the risk of diabetes complications. However, adherence to treatment regimens can be challenging because diabetes is a complex, dynamic disease that varies based on patient genetics and lifestyle choices, for example, dietary habits to exercise habits to psychological factors. Thus, collaborative systems for managing diabetes are needed to improve therapeutic efficacy for diabetes patients. Systems and methods disclosed herein can incite a behavioral change in a user of the systems or methods. Non-limiting examples of behavioral change include exercise compliance, dietary compliance, and medication compliance.

Diabetes management systems and methods disclosed herein provide an integrated and supportive system to help diabetics maintain a healthful lifestyle and achieve personal health goals. These systems and methods can help diabetics, for example, monitor blood glucose levels, manage glycemic index, keep track of dietary habits, adhere to regular exercise recommendations, provide medical knowledge, reduce stress associated with chronic disease management, and maintain psychological well-being. As a result, systems and method disclosed herein empower patients to take control of their disposition and encourage feelings of independence and positivity, which, in turn, helps improve patient adherence to treatment regimens. Implementation of systems and methods disclosed herein over a time period can result in measurable improvements to rates of patient adherence to recommended diabetes health protocols compared to patient adherence prior to implementation of the systems and methods.

For example, implementation of systems and methods disclosed herein over a period of one month can result in at least about 10%, about 20%, about 30%, about 40%, about 50%, about 60%, about 70%, about 80%, about 90%, about 100%, about 150%, about 200%, about 250%, about 300%, about 350%, about 400%, about 450%, about 500%, or greater improvement in patient adherence to recommended diabetes health protocols compared to patient adherence prior to implementation of the systems and methods.

External Devices

In some embodiments, the interactive exercise systems and methods disclosed herein can be integrated with diabetes-monitoring devices. Diabetes-monitoring devices can include, for example, smart watches, glucose monitoring devices, and pulse oximeters. Non-limiting examples of CGM devices include glucose sensing patches (e.g. FreeStyle Libre®), glucose sensing earlobe clips (e.g. GlucoWatch®), subcutaneous implants (e.g. Eversense®), and smart contact lens. In some embodiments, the glucose monitoring device is an electronic intraocular device, for example, electronic contact lenses that monitor glucose levels in a subject by sensing glucose levels in ocular fluid. CGM devices can measure glucose by ultrasonic waves, electromagnetic waves, thermal waves, radio waves, chemical reactions (e.g. fluorescent glucose polymer technology), and laser technology. Diabetes-monitoring devices can be invasive or non-invasive devices.

EXAMPLES

Example 1. Use of Algorithms for Diabetes Exercise Therapy to Improve Diabetic Outcomes A subject was a 52 year-old male diagnosed with type-2 diabetes for about 8 years. Prior to beginning the exercise therapy, the subject was on a combination anti-diabetic therapy comprising injection with insulin. The subject engaged in exercise guidance based on the methods disclosed herein, including exercise suggestions based on desired diabetes metrics outcomes, including A1C reduction, weight loss, and reduction of anti-diabetic medication usage. Having engaged the exercises based on the methods disclosed herein, the subject achieved several diabetes metrics outcomes, including: a reduction of A1C from about 9.3% to about 6.0%; a weight loss of 58 pounds; and a reduction of insulin therapy from 116 units per day to about 59 units per day.

Example 2. Use of Algorithms for Diabetes Exercise Therapy to Improve Diabetic, Cardiovascular, and Pulmonary Outcomes A subject was an elderly male that was diagnosed with type-2 diabetes and required an oxygen tank for breathing. Several years prior to beginning the exercise therapy, the subject had experienced substantial liver failure that limited the ability of the subject to exercise. The subject engaged in exercise guidance based on the methods disclosed herein, including exercise suggestions based on desired diabetic, cardiovascular, and pulmonary outcomes and capacities of the subject. Non-limiting examples of such outcomes include increased muscle tone, increased cardiac stress resistance, increased lung function, and increased sexual function.

Example 3. Use of Algorithms for Design of Targeted Type-1 Diabetes Exercise Therapy and Insulin Administration A subject is a 31 year-old female diagnosed with type-1 diabetes for 26 years. The subject measures a glucose level with a continuous glucose monitoring device and enters a resting glucose level reading into the application. The resting glucose level is 128 mg/dL. The subject selects a desired diabetes outcome in the application of A1C goal. The subject receives instruction for an exercise routine to be performed in a gym based upon weight lifting selected to create an active heart rate from 90% to 100% of the maximum heart rate of the subject. The maximum heart rate is estimated by subtracting the age of the subject from 220, to yield a maximum heart rate of 188 beats per minute (bpm).

As the instructed exercise routine creates an active heart rate from 90% to 100% of the maximum heart rate of the subject, which increases the glucose level of the subject, the application suggests adjusting the dose of insulin from a basal rate of 1 unit per hour (U/h) to an adjusted rate of 1.2 U/h. The application further utilizes real-time data from biometric devices, including a heart rate monitor and a continuous glucose monitoring device, to make further suggestions in real time related to the desired diabetes outcome, including changes in routine, and warnings to stop and or test blood sugar, or changes in hormone administration.

Example 4. Use of Algorithms for Real-Time Tracking of Type-2 Diabetes Exercise Therapy A subject is a 47 year-old female diagnosed with type-2 diabetes for 3 years. The subject is currently taking the oral medication metformin. The subject measures a glucose level with a single-point glucose monitoring device and enters a resting glucose level reading into the application. The resting glucose level is 150 mg/dL. The subject selects a desired diabetes outcome in the application of real-time reduction of blood glucose levels. The subject enters a critical glucose range of 100 mg/dL to 250 mg/dL. The subject receives instruction for a lower body cardiovascular exercise, such as jogging on a treadmill; cycling on a stationary bicycle; or running on an elliptical, utilizing slow twitch muscle fibers for 25 minutes. The exercise routine is selected to create an active heart rate from 60% to 70% of the maximum heart rate of the subject. The maximum heart rate was estimated by multiplying the age of the subject by 0.7 and subtracting the value from 208, to yield a maximum heart rate of 175.1 bpm. The application utilizes real-time data from biometric devices, including an activity tracker that monitors calorie expenditure and the single-point glucose monitoring device.

Based upon a reading of the glucose level from the single-point glucose monitoring device that the glucose level of the subject is below the critical glucose range, the application provides a warning to the subject in real time to stop the exercise routine and consume a carbohydrate to restore the glucose level to within the critical glucose range. Upon consumption of a fast-acting glucose chewable, the subject re-tests the glucose level with the single-point glucose monitoring device, which is transmitted to the application. Upon reading of the glucose level within the critical glucose range, the application suggests continuing the brisk walk with continued monitoring of the glucose level.

Example 5. Use of Algorithms for Real-Time Modification of Type-2 Diabetes Exercise Therapy A subject is a 52 year-old male diagnosed with type-2 diabetes for 7 years. The subject has previously performed several exercise routines based upon the suggestions of the application. The subject measures a glucose level with a blood glucose meter and enters a resting glucose level reading into the application. The resting glucose level is 110 mg/dL. The subject selects a desired diabetes outcome in the application of increased fat metabolism. The subject receives instruction from the application for an exercise routine based on high-intensity interval training combined with weight lifting selected to create an active heart rate from 90% to 100% of the maximum heart rate of the subject. The maximum heart rate of the subject has previously been measured through the treadmill test to be 172 bpm.

The application utilizes real-time data from biometric devices, including a heart rate monitoring device and the blood glucose meter. Based upon a reading of the glucose level from the blood glucose meter that the glucose level of the subject is above the critical glucose range of 100 mg/dL to 140 mg/dL, the application provides a warning to the subject in real time to stop the current exercise routine of high-intensity interval training combined with weight lifting. The application suggests an exercise routine based upon cycling on an exercise bicycle, along with re-testing of the glucose level with the blood glucose meter, to restore the glucose level to within the critical glucose range. The subject stops the current exercise routine of high-intensity interval training combined with weight lifting and begins the suggested exercise routine of cycling on the exercise bicycle. The subject further re-tests the glucose level with the blood glucose meter device, which is transmitted to the application. Upon reading of the glucose level within the critical glucose range, the application suggests returning to the initial exercise routine of high-intensity interval training combined with weight lifting, along with continued monitoring of the glucose level.

Example 6. Use of Algorithms for Type-1 Diabetes Exercise Therapy and Real-Time Modification of Insulin and Glucagon Administration in a Closed-Loop System A subject is a 28 year-old male diagnosed with type-1 diabetes for 23 years. The subject uses a closed-loop system including a continuous glucose monitoring device, a dual insulin/glucagon pump contained within a common housing, and a telecommunications device. The continuous glucose monitoring device transmits a resting glucose level reading into the application on the telecommunications device. The resting glucose level is 139 mg/dL. The subject selects a desired diabetes outcome in the application of A1C reduction. The subject receives instruction for an exercise routine to be performed with an exercise instruction video to reach a target heart rate from 60% to 70% of the maximum heart rate of the subject. The subject sets the critical glucose range to be from 100 mg/dL to 140 mg/dL. The maximum heart rate is estimated by subtracting the age of the subject from 220, to yield a maximum heart rate of 192 bpm.

As the instructed exercise routine creates an active heart rate from 60% to 70% of the maximum heart rate of the subject, which decreases the glucose level of the subject, the application suggests adjusting the dose of insulin from a basal rate of 1 U/h to an adjusted rate of 0.9 U/h and adjusting the dose of glucagon from a basal rate of 0.4 U/h to an adjusted rate of 0.5 U/h. The application further utilizes real-time data from the continuous glucose monitoring device of the closed-loop system and displays the glucose level readings with the exercise instruction video in real time. During the exercise instruction video, the glucose level rises above the critical glucose range, which is displayed on the exercise instruction video. The closed-loop system responds to the glucose level reading to increase the rate of the dose of insulin to 0.95 U/h and decrease the rate of the dose of glucagon to 0.45 U/h. The closed-loop system continues to monitor the glucose level with the continuous glucose monitoring device, transmitting the readings to the application and displaying the readings on the exercise instruction video.

Example 7. Interactive Diabetes Exercise Program Dashboard

Figure 9:
FIG. 9 illustrates a display of the interactive exercise program.

FIG. 9 shows an example display of the main page dashboard of the interactive exercise program.

The main menu icon (1) slides open from the left side of the display when selected by the user. The main menu icon leads the user to various menu tabs that provide user options. User options can include, for example, accessing user profile, data settings, and messages.

The program/workout calendar icon (2) can slide open from the right side of the display when selected by the user. The program/workout calendar icon opens a specific program designed for the user. The workouts can be outlined week by week.

The Hours below Live Workout icon (3) can be used to search a specific Live Workout video based on start time. The bar works as slider that moves from left to right. The user can select a specific Live Workout video by selecting the start time. The right panel shows a zoomed out schematic of videos that can be selected when the user scrolls up and down.

Figure 10:
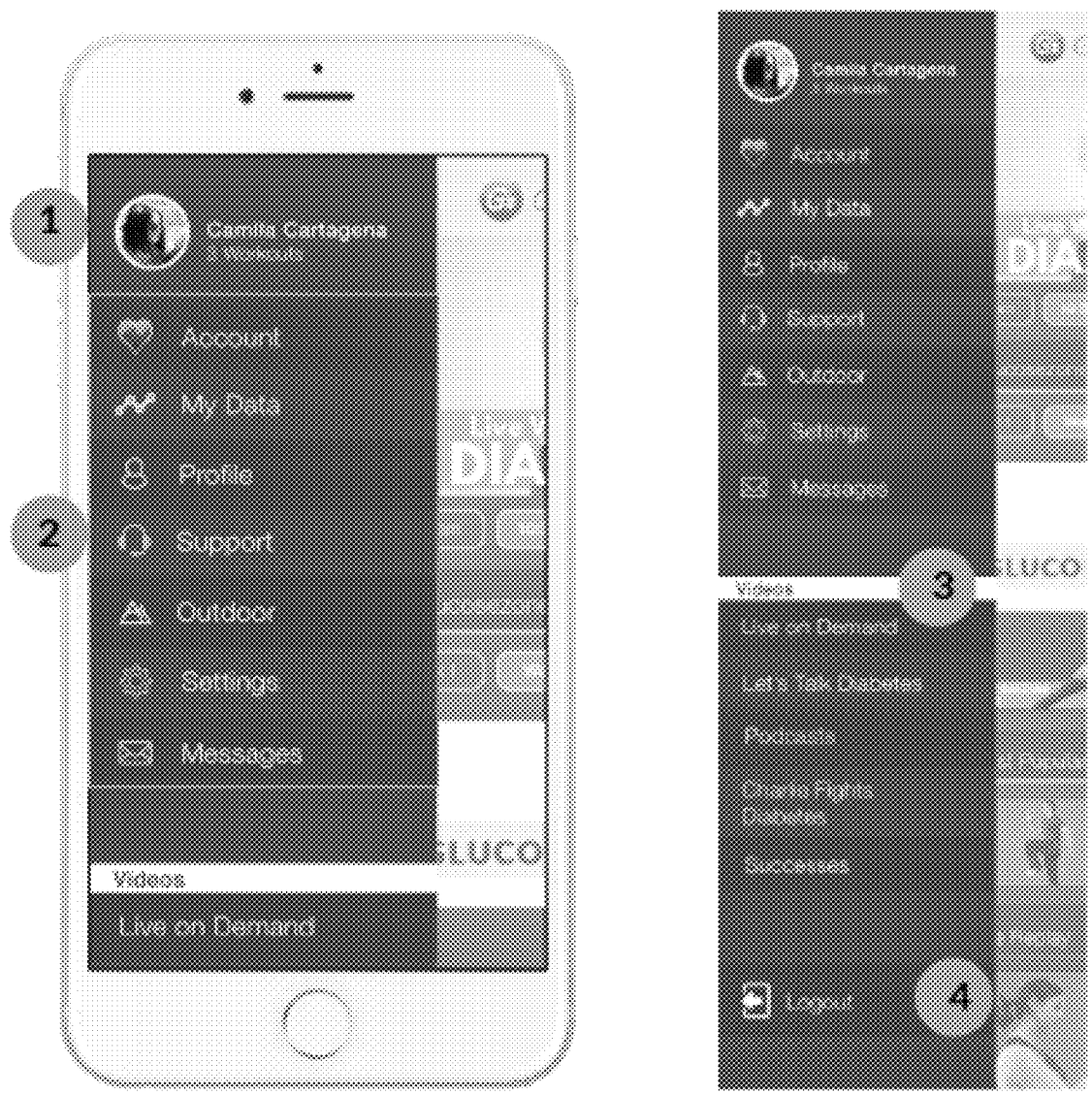
FIG. 10 illustrates a display of the interactive exercise program.

FIG. 10 shows an example display of the main page dashboard of the interactive exercise program when the main menu icon (1) shown in FIG. 9 is selected. The menu bar can display a user profile image (1) and the number of workouts completed by the user. Menu options (2) can provide specific functions for the user. Menu options can include, for example, account information, user biometric data, user profile, support options, outdoor exercise routines, settings, messages, and live on-demand exercise routines. User can access live or recorded media (3), for example, live on-demand routines, podcasts, and other information about the program. The logout icon (4) allows users to log off of an account.

Figure 11:
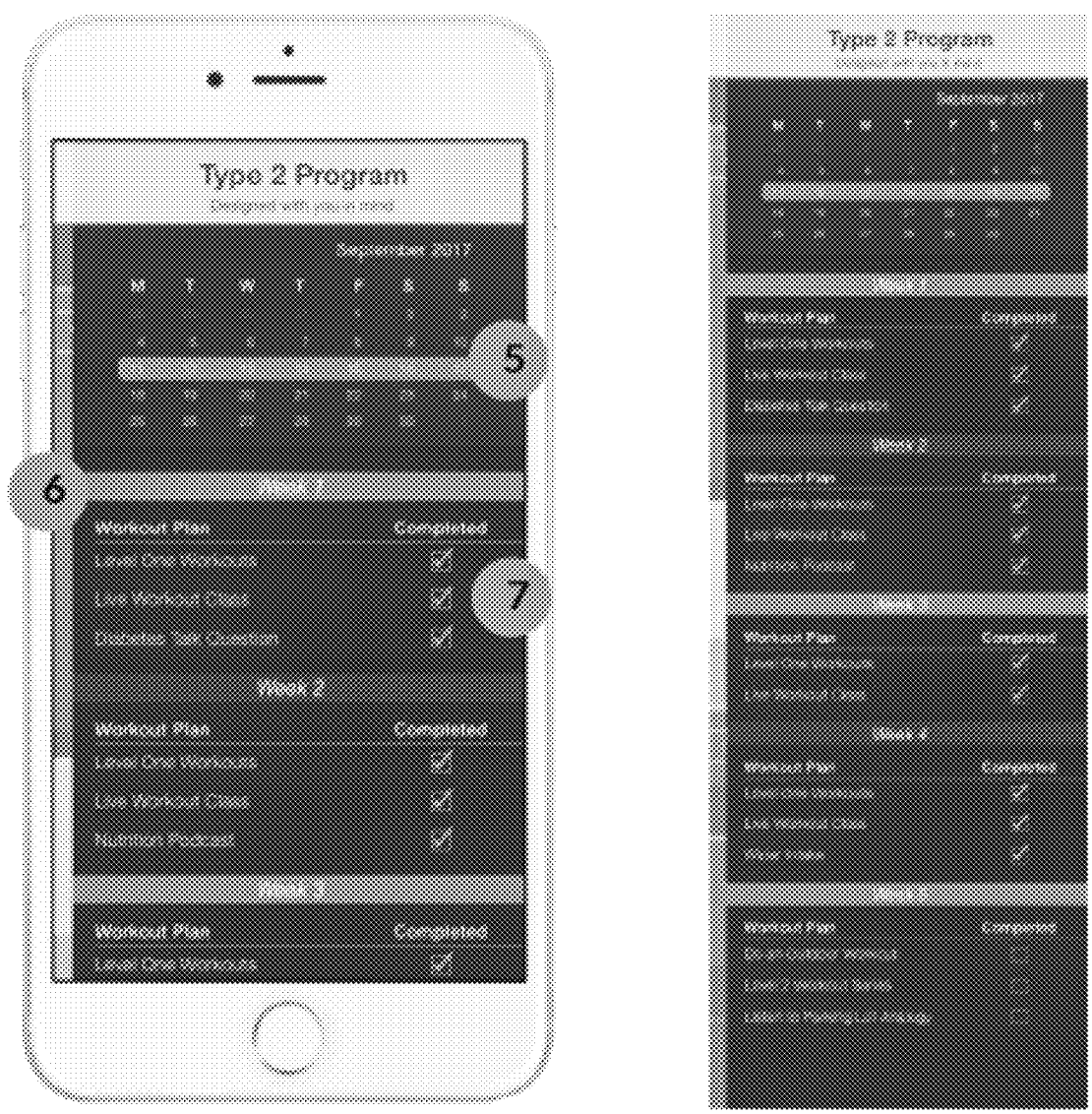
FIG. 11 illustrates a display of the interactive exercise program.

FIG. 11 shows an example display of the main page dashboard of the interactive exercise program. User can display a calendar of the program (5) to track user progress. Highlighted dates can indicate user completion of exercises. In the calendar interface, the user can view the week of a program (6) that details a specific workout routine and completion status. As the user completes a workout, the program automatically checks off the completed box (7) to indicate completion. The right panel shows a zoomed out schematic of detailed weekly exercise routines and completion status that can be viewed when the user scrolls up and down.

Figure 12:
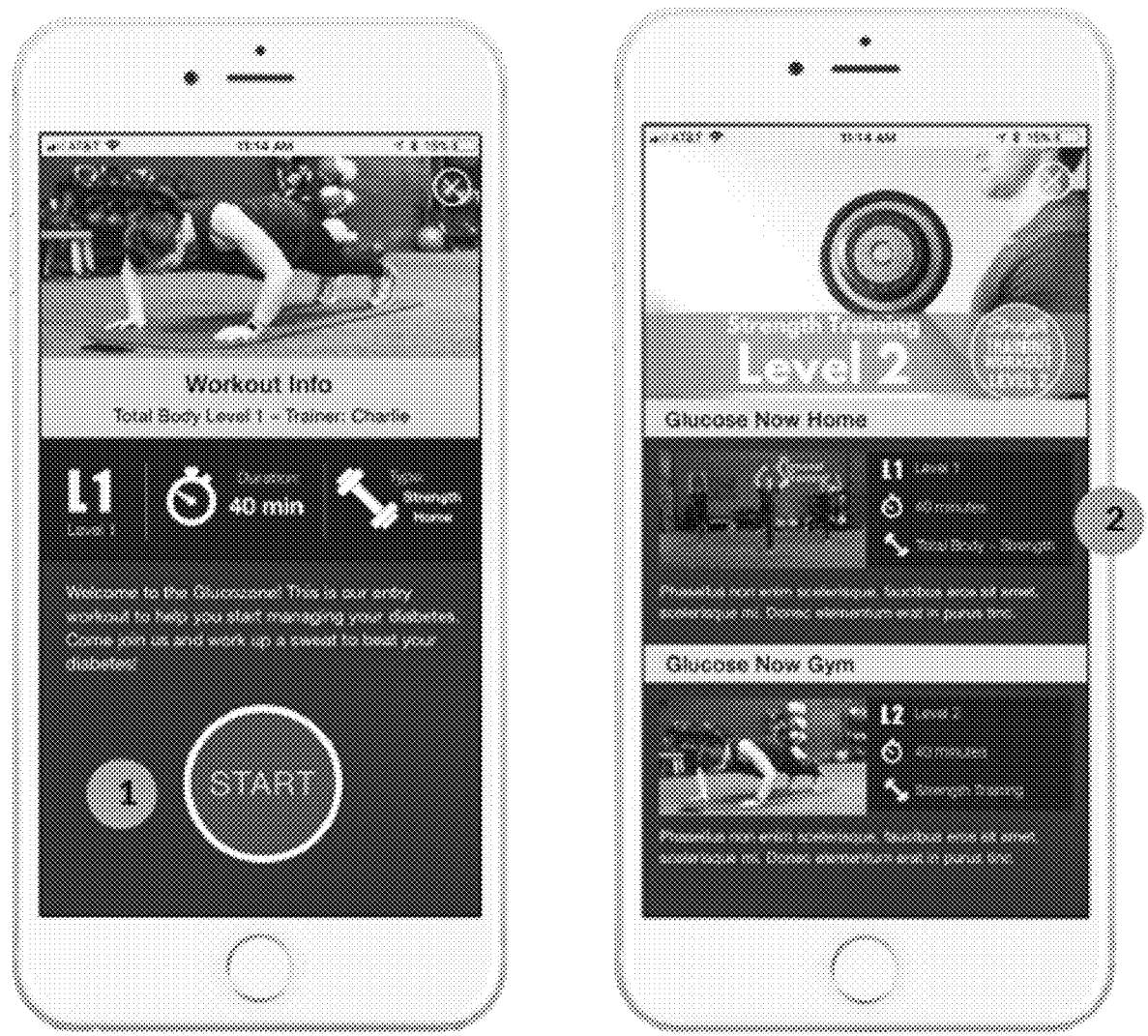
FIG. 12 illustrates a display of the interactive exercise program.

FIG. 12 shows an example display of the workout pages. The workout pages can be accessed from the main page dashboard. When a user selects a desired workout, the workout pages are displayed. The workout information pages (2) can provide detailed information about the workout, for example, level of difficulty, duration, exercise type, performance location (e.g., outdoors or at home). To begin an exercise, a user can select the start button (1).

Example 8. Targeted Advertising Using Real-Time Biometrics

A system of the invention is used to detect a user's biometrics during performance of a physical exercise. The exercise can be based on an instructional exercise provided by the system, for example, a biometrics-driven exercise program described herein.

A system of the invention monitors a diabetic patient's real-time biometrics while the patient is performing a high intensity aerobic exercise. The system can monitor, for example, the patient's heart rate, blood glucose level, insulin level, and lipoprotein levels. The system can detect that the patient is nearing completion of the exercise and will likely require consumption of a food or beverage to restore blood glucose levels to normal. In response, the system can present to the patient an advertisement for a food, for example, an energy beverage.

A system of the invention monitors a diabetic patient's real-time biometrics and detects an abnormal rate of decrease in blood glucose level in the patient. In response, the system can present to the patient an advertisement for a food product that would reduce the likelihood of such precipitous variations in blood glucose level in the future. The system can provide recommendations for a product or service that can guide the patient on dosing and administration of a medication. Changes in the patient's biometrics can also trigger the system to present to the patient different types of wearable devices, equipment, or programs that relate to monitoring, controlling, and managing biometric conditions.

The system can also detect shopping habits of the user. For example, the system detects that a user that purchases blood glucose test strips. In response, the system can present to the patient advertisements for products or services related to diabetes.

Example 9. Virtual Health Assistant Using Real-Time Biometrics

A user of the system is a type-2 diabetic patient recommended to modify lifestyle habits to increase insulin sensitivity and lose weight by performing regular exercise and adjusting dietary habits. The system can monitor the patient's daily exercise and dietary habits, and provide step-by-step instruction and performance feedback.

The system can detect that a patient is skipping the instructional exercises recommended by the instructional exercise system, for example, due to schedule conflicts. The system can recommend a tailored exercise schedule for the patient to adhere to the exercise recommendations. For a patient who does not have time to exercise during the week due to a work schedule, the system can recommend that the patient take a certain route to work to increase activity levels, for example, walking instead of taking the bus or taking stairs instead of taking the elevator.

The system can detect the patient's location to recommend local restaurant options or types of foods that are compatible with the patient's health goals. The patient can monitor dietary habits by taking photos or videos of meals or providing descriptions of nutritional content of meals if available. For example, the patient can upload an image of a cheeseburger. The system can provide estimated nutritional facts of the cheeseburger based on the image provided by the patient. The system can monitor the metabolic effect of the cheeseburger on the patient by detecting biometrics over time, for example, blood glucose level after consumption. The system can recommend alternative food options that are more compatible with personal taste preferences of the patient based on detected dietary habits, as well as the patient's health goals. For example, the system can learn that a cheeseburger results in elevated triglyceride levels, elevated blood glucose levels, and reduced insulin sensitivity. Thus, consumption of a cheeseburger is not incompatible with the patient's prescribed health recommendation. As a result, the system can suggest a cheeseburger alternative that has reduced fat and calorie content. Over time, the system can progressively influence the patient to make more healthful choices to achieve the patient's health goals.

Figure 18:
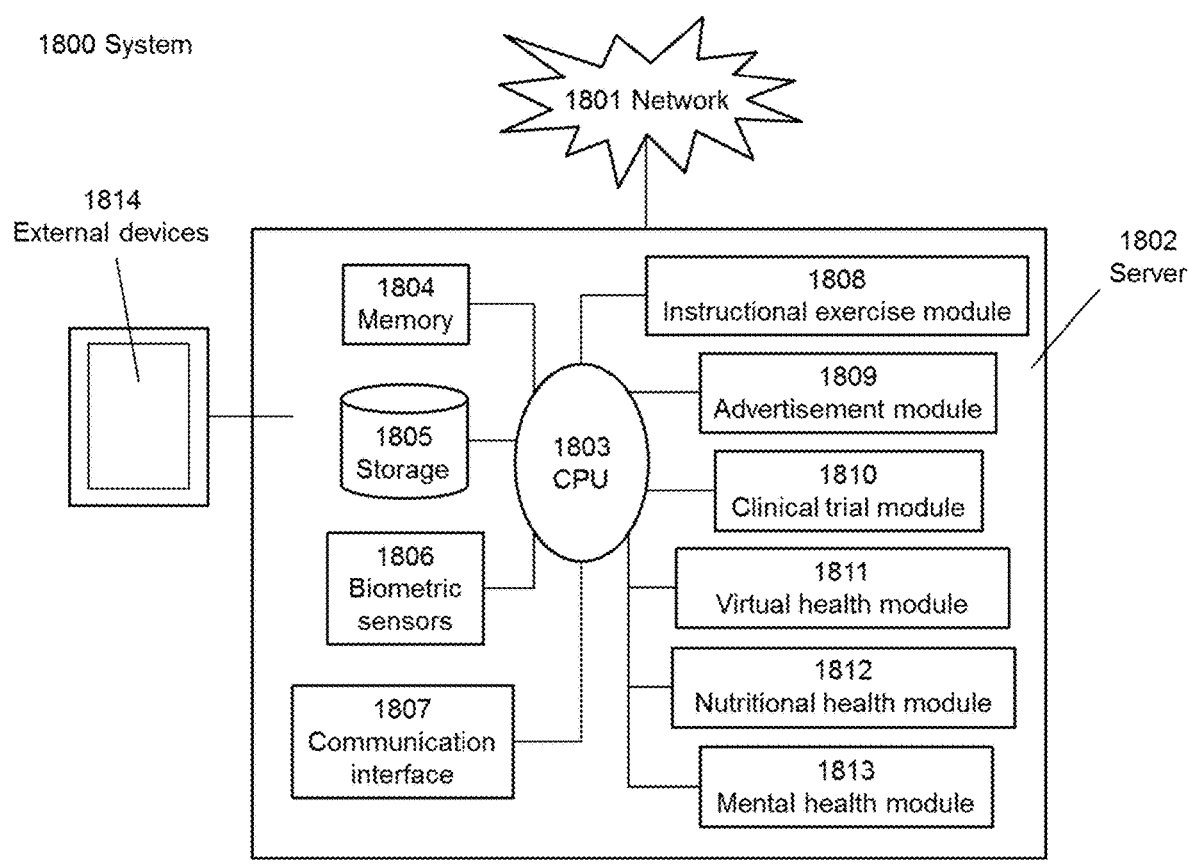
FIG. 18 illustrates a computer system for facilitating methods, systems, kits, or devices of the disclosure.

FIG. 18 illustrates a computer system 1800 programmed or otherwise configured to allow monitoring of a biometric of a subject by biometric sensors 1806 or external biometric devices 1814, present an instructional exercise by instructional exercise module 1808, and optionally present an advertisement by the advertisement module 1809, determine subject eligibility in a clinical trial by the clinical trial module 1810, provide health guidance by the virtual health module 1811, provide nutritional health guidance by the nutritional health module 1812, or provide mental health guidance by the mental health module 1813, in accordance with various embodiments of the disclosure. The computer system 1800 includes a server 1802, a CPU 1803, a memory 1804, a storage unit 1805, biometric sensors 1806, and a communication interface 1807.

Embodiments

Embodiment 101. A method comprising: a) administering to a subject a basal dose of insulin, wherein the subject is in need thereof, and wherein the subject is diabetic; b) subsequent to the administering to the subject the basal dose of insulin, administering to the subject an adjusted dose of insulin, wherein the adjusted dose of insulin is from about 5% to about 95% of the basal dose of insulin; c) subsequent to the administering to the subject the adjusted dose of insulin, sustaining the subject's heart rate at a level that is from 10%-50% of the subject's maximum heart rate for at least 30 minutes; and d) subsequent to the sustaining the subject's heart rate at the level that is from 10%-50% of the subject's maximum heart rate for at least 30 minutes, elevating the subject's heart rate to a level that is at least 50% of the subject's maximum heart rate.

Embodiment 102. The method of embodiment 101, wherein the subject has type-1 diabetes.

Embodiment 103. The method of embodiment 101, wherein the subject has type-2 diabetes.

Embodiment 104. The method of any one of embodiments 101-103, further comprising administering glucagon to the subject.

Embodiment 105. The method of any one of embodiments 101-104, wherein the adjusted dose of insulin is about 15% of the basal dose of insulin, and the subject's heart rate is elevated to 50-60% of the subject's maximum heart rate.

Embodiment 106. The method of any one of embodiments 101-104, wherein the adjusted dose of insulin is about 15% of the basal dose of insulin, and the subject's heart rate is elevated to 60-70% of the subject's maximum heart rate.

Embodiment 107. The method of any one of embodiments 101-104, wherein the adjusted dose of insulin is about 50% of the basal dose of insulin, and the subject's heart rate is elevated to 70-80% of the subject's maximum heart rate.

Embodiment 108. The method of any one of embodiments 101-104, wherein the adjusted dose of insulin is about 85% of the basal dose of insulin, and the subject's heart rate is elevated to 80-90% of the subject's maximum heart rate.

Embodiment 109. The method of any one of embodiments 101-104, wherein the adjusted dose of insulin is about 90% of the basal dose of insulin, and the subject's heart rate is elevated to 90-100% of the subject's maximum heart rate.

Embodiment 110. The method of any one of embodiments 101-109, wherein the basal dose of insulin and the adjusted dose of insulin are administered to the subject via an external medical device.

Embodiment 111. The method of any one of embodiments 101-110, wherein the basal dose of insulin and the adjusted dose of insulin are administered to the subject via an insulin pump.

Embodiment 112. The method of any one of embodiments 101-111, wherein the subject's heart rate is sustained at a level that is from 10%-50% of the subject's maximum heart rate for at least 60 minutes.

Embodiment 113. The method of any one of embodiments 101-112, wherein the subject's heart rate is sustained at a level that is from 10%-50% of the subject's maximum heart rate by promoting a state of physical rest for the subject.

Embodiment 114. The method of any one of embodiments 101-113, wherein the subject's heart rate is elevated to a level that is at least 50% of the subject's maximum heart rate by promoting a state of physical exercise for the subject.

Embodiment 115. The method of any one of embodiments 101-113, wherein the subject's heart rate is elevated to a level that is at least 50% of the subject's maximum heart rate by promoting a state of physical exercise for the subject, wherein the state of physical exercise is promoted by presenting to the subject an exercise instruction via an electronic communication medium.

Embodiment 116. The method of any one of embodiments 101-113, wherein the subject's heart rate is elevated to a level that is at least 50% of the subject's maximum heart rate by promoting a state of physical exercise for the subject, wherein the state of physical exercise is promoted by presenting to the subject an exercise instruction via an electronic communication medium, wherein the electronic communication medium is processed by a computer system that is in communication with a biometric device that is in contact with the subject.

Embodiment 117. The method of any one of embodiments 101-113, wherein the subject's heart rate is elevated to a level that is at least 50% of the subject's maximum heart rate by promoting a state of physical exercise for the subject, wherein the state of physical exercise is promoted by presenting to the subject an exercise instruction via an electronic communication medium, wherein the electronic communication medium is processed by a computer system that is in communication with a biometric device that is in contact with the subject, wherein the computer system: 1) receives a reading of a biometric parameter of the subject at a time point from the biometric device; and 2) displays the reading of the biometric parameter on the electronic communication medium.

Embodiment 118. The method of any one of embodiments 101-113, wherein the subject's heart rate is elevated to a level that is at least 50% of the subject's maximum heart rate by promoting a state of physical exercise for the subject, wherein the state of physical exercise is promoted by presenting to the subject an exercise instruction via an electronic communication medium, wherein the electronic communication medium is processed by a computer system that is in communication with a biometric device that is in contact with the subject, wherein the computer system: 1) receives a reading of a biometric parameter of the subject at a time point from the biometric device; and 2) determines based on the biometric parameter the suitability at the time point for the subject of an exercise instruction presented to the subject.

Embodiment 119. The method of any one of embodiments 101-113, wherein the subject's heart rate is elevated to a level that is at least 50% of the subject's maximum heart rate by promoting a state of physical exercise for the subject, wherein the state of physical exercise is promoted by presenting to the subject an exercise instruction via an electronic communication medium, wherein the electronic communication medium is processed by a computer system that is in communication with a biometric device that is in contact with the subject, wherein the computer system: 1) receives a reading of a biometric parameter of the subject at a time point from the biometric device; 2) determines based on the biometric parameter that an exercise instruction presented to the subject is unsuitable for the subject at the time point; 3) alerts the subject that the biometric parameter has deviated from a target range; 4) stops the presentation of the electronic communication medium; and 5) presents to the subject, based on the biometric parameter, an alternative electronic communication medium that provides an alternative exercise instruction that is suitable for the subject.

Embodiment 120. The method of any one of embodiments 116-119, wherein the biometric device monitors the subject's glucose level.

Embodiment 121. The method of any one of embodiments 116-120, wherein the biometric device monitors the subject's heart rate.

Embodiment 122. The method of any one of embodiment 115-121, wherein the electronic communication medium is a video.

Embodiment 201. A method comprising: a) administering to a subject a basal dose of insulin, wherein the subject is in need thereof, and wherein the subject is diabetic; b) receiving from the subject a selection of an exercise that the subject is to perform; c) determining based on the exercise that the subject is to perform an adjusted dose of insulin for administration to the subject, wherein the adjusted dose of insulin is from about 5% to about 95% of the basal dose of insulin; d) administering to the subject the adjusted dose of insulin; e) subsequent to the administering to the subject the adjusted dose of insulin, sustaining the subject's heart rate at a level that is from 10%-50% of the subject's maximum heart rate for at least 30 minutes; and f) subsequent to the sustaining the subject's heart rate at the level that is from 10%-50% of the subject's maximum heart rate for at least 30 minutes, monitoring the subject's heart rate to detect an elevation in the subject's heart rate, wherein the elevation in the subject's heart rate is to a level that is at least 50% of the subject's maximum heart rate.

Embodiment 202. The method of embodiment 201, wherein the subject has type-1 diabetes.

Embodiment 203. The method of embodiment 201, wherein the subject has type-2 diabetes.

Embodiment 204. The method of any one of embodiments 201-203, further comprising administering glucagon to the subject.

Embodiment 205. The method of any one of embodiments 201-204, wherein the adjusted dose of insulin is about 15% of the basal dose of insulin, and the elevation in the subject's heart rate is to 50-60% of the subject's maximum heart rate.

Embodiment 206. The method of any one of embodiments 201-204, wherein the adjusted dose of insulin is about 15% of the basal dose of insulin, and the elevation in the subject's heart rate is to 60-70% of the subject's maximum heart rate.

Embodiment 207. The method of any one of embodiments 201-204, wherein the adjusted dose of insulin is about 50% of the basal dose of insulin, and the elevation in the subject's heart rate is to 70-80% of the subject's maximum heart rate.

Embodiment 208. The method of any one of embodiments 201-204, wherein the adjusted dose of insulin is about 85% of the basal dose of insulin, and the elevation in the subject's heart rate is to 80-90% of the subject's maximum heart rate.

Embodiment 209. The method of any one of embodiments 201-204, wherein the adjusted dose of insulin is about 90% of the basal dose of insulin, and the elevation in the subject's heart rate is to 90-100% of the subject's maximum heart rate.

Embodiment 210. The method of any one of embodiments 201-209, wherein the basal dose of insulin and the adjusted dose of insulin are administered to the subject via an external medical device.

Embodiment 211. The method of any one of embodiments 201-209, wherein the basal dose of insulin and the adjusted dose of insulin are administered to the subject via an insulin pump.

Embodiment 212. The method of any one of embodiments 201-211, wherein the subject's heart rate is sustained at a level that is from 10%-50% of the subject's maximum heart rate for at least 60 minutes.

Embodiment 213. The method of any one of embodiments 201-212, wherein the subject's heart rate is sustained at a level that is from 10%-50% of the subject's maximum heart rate by promoting a state of physical rest for the subject.

Embodiment 214. The method of any one of embodiments 201-213, further comprising presenting to the subject an exercise instruction via an electronic communication medium.

Embodiment 215. The method of any one of embodiments 201-213, further comprising presenting to the subject an exercise instruction via an electronic communication medium, wherein the electronic communication medium is processed by a computer system that is in communication with a biometric device that is in contact with the subject.

Embodiment 216. The method of any one of embodiments 201-213, further comprising presenting to the subject an exercise instruction via an electronic communication medium, wherein the electronic communication medium is processed by a computer system that is in communication with a biometric device that is in contact with the subject, wherein the computer system: 1) receives a reading of a biometric parameter of the subject at a time point from the biometric device; and 2) displays the reading of the biometric parameter on the electronic communication medium.

Embodiment 217. The method of any one of embodiments 201-213, further comprising presenting to the subject an exercise instruction via an electronic communication medium, wherein the electronic communication medium is processed by a computer system that is in communication with a biometric device that is in contact with the subject, wherein the computer system: 1) receives a reading of a biometric parameter of the subject at a time point from the biometric device; and 2) determines based on the biometric parameter the suitability at the time point for the subject of an exercise instruction presented to the subject.

Embodiment 218. The method of any one of embodiments 201-213, further comprising presenting to the subject an exercise instruction via an electronic communication medium, wherein the electronic communication medium is processed by a computer system that is in communication with a biometric device that is in contact with the subject, wherein the computer system: 1) receives a reading of a biometric parameter of the subject at a time point from the biometric device; 2) determines based on the biometric parameter that an exercise instruction presented to the subject is unsuitable for the subject at the time point; 3) alerts the subject that the biometric parameter has deviated from a target range; 4) stops the presentation of the electronic communication medium; and 5) presents to the subject, based on the biometric parameter, an alternative electronic communication medium that provides an alternative exercise instruction that is suitable for the subject.

Embodiment 219. The method of any one of embodiments 215-218, wherein the biometric device monitors the subject's glucose level.

Embodiment 220. The method of any one of embodiments 215-218, wherein the biometric device monitors the subject's heart rate.

Embodiment 221. The method of any one of embodiments 214-220, wherein the electronic communication medium is a video.

Embodiment 301. A method comprising: a) receiving by a subject a basal dose of insulin, wherein the subject is in need thereof, and wherein the subject is diabetic; b) subsequent to the receiving the basal dose of insulin, receiving by the subject an adjusted dose of insulin, wherein the adjusted dose of insulin is from about 5% to about 95% of the basal dose of insulin; c) subsequent to the receiving by the subject the adjusted dose of insulin, sustaining by the subject the subject's heart rate at a level that is from 10%-50% of the subject's maximum heart rate for at least 30 minutes; and d) subsequent to the sustaining the subject's heart rate at the level that is from 10%-50% of the subject's maximum heart rate for at least 30 minutes, elevating by the subject the subject's heart rate to a level that is at least 50% of the subject's maximum heart rate.

Embodiment 302. The method of embodiment 301, wherein the subject has type-1 diabetes.

Embodiment 303. The method of embodiment 301, wherein the subject has type-2 diabetes.

Embodiment 304. The method of any one of embodiments 301-303, further comprising receiving a dose of glucagon by the subject.

Embodiment 305. The method of any one of embodiments 301-304, wherein the adjusted dose of insulin is about 15% of the basal dose of insulin, and the subject's heart rate is elevated to 50-60% of the subject's maximum heart rate.

Embodiment 306. The method of any one of embodiments 301-304, wherein the adjusted dose of insulin is about 15% of the basal dose of insulin, and the subject's heart rate is elevated to 60-70% of the subject's maximum heart rate.

Embodiment 307. The method of any one of embodiments 301-304, wherein the adjusted dose of insulin is about 50% of the basal dose of insulin, and the subject's heart rate is elevated to 70-80% of the subject's maximum heart rate.

Embodiment 308. The method of any one of embodiments 301-304, wherein the adjusted dose of insulin is about 85% of the basal dose of insulin, and the subject's heart rate is elevated to 80-90% of the subject's maximum heart rate.

Embodiment 309. The method of any one of embodiments 301-304, wherein the adjusted dose of insulin is about 90% of the basal dose of insulin, and the subject's heart rate is elevated to 90-100% of the subject's maximum heart rate.

Embodiment 310. The method of any one of embodiments 301-309, wherein the subject receives the basal dose of insulin and the adjusted dose of insulin via an external medical device.

Embodiment 311. The method of any one of embodiments 301-309, wherein the subject receives the basal dose of insulin and the adjusted dose of insulin via an insulin pump.

Embodiment 312. The method of any one of embodiments 301-311, wherein the subject's heart rate is sustained at a level that is from 10%-50% of the subject's maximum heart rate for at least 60 minutes.

Embodiment 313. The method of any one of embodiments 301-312, wherein the subject's heart rate is sustained at a level that is from 10%-50% of the subject's maximum heart rate by a state of physical rest.

Embodiment 314. The method of any one of embodiments 301-313, wherein the subject's heart rate is elevated to a level that is at least 50% of the subject's maximum heart rate by a state of physical exercise.

Embodiment 315. The method of any one of embodiments 301-313, wherein the subject's heart rate is elevated to a level that is at least 50% of the subject's maximum heart rate by a state of physical exercise, wherein the state of physical exercise is promoted by receiving by the subject an electronic communication medium that provides exercise instruction.

Embodiment 316. The method of any one of embodiments 301-313, wherein the subject's heart rate is elevated to a level that is at least 50% of the subject's maximum heart rate by a state of physical exercise, wherein the state of physical exercise is promoted by receiving by the subject an electronic communication medium that provides exercise instruction, wherein the electronic communication medium is processed by a computer system that is in communication with a biometric device that is in contact with the subject.

Embodiment 317. The method of any one of embodiments 301-313, wherein the subject's heart rate is elevated to a level that is at least 50% of the subject's maximum heart rate by promoting a state of physical exercise for the subject, wherein the state of physical exercise is promoted by receiving by the subject an electronic communication medium that provides exercise instruction, wherein the electronic communication medium is processed by a computer system that is in communication with a biometric device that is in contact with the subject, wherein the computer system: 1) receives a reading of a biometric parameter of the subject at a time point from the biometric device; and 2) communicates the reading of the biometric parameter to the subject.

Embodiment 318. The method of any one of embodiments 301-313, wherein the subject's heart rate is elevated to a level that is at least 50% of the subject's maximum heart rate by a state of physical exercise, wherein the state of physical exercise is promoted by receiving by the subject an electronic communication medium that provides exercise instruction, wherein the electronic communication medium is processed by a computer system that is in communication with a biometric device that is in contact with the subject, wherein the computer system: 1) receives a reading of a biometric parameter of the subject at a time point from the biometric device; and 2) determines based on the biometric parameter the suitability at the time point for the subject of an exercise instruction presented to the subject.

Embodiment 319. The method of any one of embodiments 301-313, wherein the subject's heart rate is elevated to a level that is at least 50% of the subject's maximum heart rate by a state of physical exercise, wherein the state of physical exercise is promoted by receiving by the subject an electronic communication medium that provides exercise instruction, wherein the electronic communication medium is processed by a computer system that is in communication with a biometric device that is in contact with the subject, wherein the computer system: 1) receives a reading of a biometric parameter of the subject at a time point from the biometric device; 2) determines based on the biometric parameter that an exercise instruction presented to the subject is unsuitable for the subject at the time point; 3) alerts the subject that the biometric parameter has deviated from a target range; 4) stops the presentation of the electronic communication medium; and 5) presents to the subject, based on the biometric parameter, an alternative electronic communication medium that provides an alternative exercise instruction that is suitable for the subject.

Embodiment 320. The method of any one of embodiments 301-319, wherein the subject communicates a selection of an exercise to perform to a computer system, wherein the computer system determines a level of the adjusted dose of insulin based on the exercise to perform and a reading of a biometric device that is in contact with the subject.

Embodiment 321. The method of embodiment 320, wherein the subject receives exercise instruction from the computer system based on the exercise to perform and the reading of the biometric device that is in contact with the subject.

Embodiment 322. The method of any one of embodiments 315-321, wherein the electronic communication medium is a video.

Embodiment 323. The method of any one of embodiments 316-322, wherein the biometric device monitors the subject's glucose level.

Embodiment 324. The method of any one of embodiments 316-323, wherein the biometric device monitors the subject's heart rate.

Embodiment 325. The method of any one of embodiments 320-321, wherein the subject receives from the computer system an indication of the suitability of the exercise for the subject based on the reading of the biometric device that is in contact with the subject.

Embodiment 326. The method of any one of embodiments 320-321, wherein the subject receives from the computer system an indication that the exercise is unsuitable for the subject based on the reading of the biometric device that is in contact with the subject.

Embodiment 327. The method of any one of embodiments 320-321, wherein the subject receives from the computer system an instruction to perform an alternative exercise instruction that is suitable for the subject based on the reading of the biometric device that is in contact with the subject.

Embodiment 401. A system comprising: a) a telecommunications device; b) an insulin delivery device that is: 1) in contact with a subject; 2) in communication with the telecommunications device; 3) configured to administer insulin to the subject; and 4) configured to receive from the telecommunications device a transmission of an instruction to administer to the subject a dose of insulin; and c) a glucose monitoring device that is: 1) in contact with the subject; 2) in communication with the telecommunications device; 3) configured to detect a glucose level in the subject; and 4) configured to transmit to the telecommunications device a reading of the glucose level in the subject, wherein the telecommunications device sends a transmission from the telecommunications device to the insulin delivery device, wherein the transmission instructs the insulin delivery device to administer to the subject an adjusted dose of insulin over a period of at least 30 minutes, wherein the adjusted dose of insulin is from about 5% to about 95% of a basal dose of insulin for the subject.

Embodiment 402. The system of embodiment 1, wherein the telecommunications device is configured to display the glucose level detected in the subject by the glucose monitoring device.

Embodiment 403. The system of any one of embodiments 401-402, wherein the insulin delivery device is configured to adjust an amount of insulin that is administered to the subject based on the glucose level detected in the subject by the glucose monitoring device.

Embodiment 404. The system of any one of embodiments 401-403, wherein the insulin delivery device and the glucose monitoring device are in a common housing.

Embodiment 405. The system of any one of embodiments 401-403, wherein the insulin delivery device, the glucose monitoring device, and the telecommunications device are in a common housing.

Embodiment 406. The system of any one of embodiments 401-403, further comprising a glucagon delivery device that is: 1) in contact with the subject; 2) in communication with the telecommunications device; 3) configured to administer glucagon to the subject; and 4) configured to receive from the telecommunications device an instruction to administer to the subject a dose of glucagon.

Embodiment 407. The system of embodiment 406, wherein the insulin delivery device and the glucagon delivery device are in a common housing.

Embodiment 408. The system of embodiment 406, wherein the insulin delivery device, the glucose monitoring device, and the glucagon delivery device are in a common housing.

Embodiment 409. The system of embodiment 406, wherein the insulin delivery device, the glucose monitoring device, the glucagon delivery device, and the telecommunications device are in a common housing.

Embodiment 410. The system of any one of embodiments 406-409, wherein the glucagon delivery device is configured to adjust an amount of glucagon that is administered to the subject based on the glucose level detected in the subject by the glucose monitoring device.

Embodiment 411. The system of any one of embodiments 401-410, wherein the transmission from the telecommunications device to the insulin delivery device instructs the insulin delivery device to administer to the subject an adjusted dose of insulin over a period of at least 60 minutes.

Embodiment 412. The system of any one of embodiments 401-411, wherein the adjusted dose of insulin is about 15% of the basal dose of insulin.

Embodiment 413. The system of any one of embodiments 401-411, wherein the adjusted dose of insulin is about 50% of the basal dose of insulin.

Embodiment 414. The system of any one of embodiments 401-411, wherein the adjusted dose of insulin is about 85% of the basal dose of insulin.

Embodiment 415. The system of any one of embodiments 401-411, wherein the adjusted dose of insulin is about 90% of the basal dose of insulin.

Embodiment 416. The system of any one of embodiments 401-415, wherein the telecommunications device is in communication with a media device, wherein the telecommunications device instructs the media device to present to the subject an instructional exercise electronic communication medium based on the glucose level detected in the subject by the glucose monitoring device.

Embodiment 417. The system of embodiment 416, wherein the electronic communication medium is a video.

Embodiment 418. The system of any one of embodiments 401-417, wherein the telecommunications device is configured to determine a level of the dose of insulin based on an input of an exercise to be performed by the subject and the reading of the glucose level in the subject by the glucose monitoring device.

Embodiment 419. The system of any one of embodiments 401-418, wherein any device or housing is implanted in the subject.

Embodiment 501. A system comprising: a) a telecommunications device; b) an insulin delivery device that is: 1) in contact with a subject; 2) in communication with the telecommunications device; 3) configured to administer insulin to the subject; and 4) configured to receive from the telecommunications device a transmission of an instruction to administer to the subject a dose of insulin; c) a glucose monitoring device that is: 1) in contact with the subject; 2) in communication with the telecommunications device; 3) configured to detect a glucose level in the subject; and 4) configured to transmit to the telecommunications device a reading of the glucose level in the subject; and d) a heart rate monitor device that is: 1) in contact with the subject; 2) in communication with the telecommunications device; 3) configured to detect a heart rate in the subject; and 4) configured to transmit to the telecommunications device a reading of the heart rate in the subject, wherein the telecommunications device sends a transmission from the telecommunications device to the insulin delivery device, wherein the transmission instructs the insulin delivery device, based on the reading of the heart rate of the subject, to administer to the subject an adjusted dose of insulin over a period of at least 30 minutes, wherein the adjusted dose of insulin is from about 5% to about 95% of a basal dose of insulin for the subject.

Embodiment 502. The system of embodiment 501, wherein the telecommunications device is configured to display the glucose level detected in the subject by the glucose monitoring device and the heart rate detected in the subject by the heart rate monitoring device.

Embodiment 503. The system of any one of embodiments 501-502, wherein the insulin delivery device is configured to adjust an amount of insulin that is administered to the subject based on the glucose level detected in the subject by the glucose monitoring device and the heart rate detected in the subject by the heart rate monitoring device.

Embodiment 504. The system of any one of embodiments 501-503, wherein the insulin delivery device and the glucose monitoring device are in a common housing.

Embodiment 505. The system of any one of embodiments 501-503, wherein the insulin delivery device, the glucose monitoring device, and the heart rate monitoring device are in a common housing.

Embodiment 506. The system of any one of embodiments 501-503, wherein the insulin delivery device, the glucose monitoring device, and the telecommunications device are in a common housing.

Embodiment 507. The system of any one of embodiments 501-503, wherein the insulin delivery device, the glucose monitoring device, the heart rate monitoring device, and the telecommunications device are in a common housing Embodiment 508. The system of any one of embodiments 501-507, further comprising a glucagon delivery device that is: 1) in contact with the subject; 2) in communication with the telecommunications device; 3) configured to administer glucagon to the subject; and 4) configured to receive from the telecommunications device an instruction to administer to the subject a dose of glucagon.

Embodiment 509. The system of embodiment 508, wherein the insulin delivery device and the glucagon delivery device are in a common housing.

Embodiment 510. The system of embodiment 508, wherein the insulin delivery device, the glucose monitoring device, the heart rate monitoring device, and the glucagon delivery device are in a common housing.

Embodiment 511. The system of embodiment 508, wherein the insulin delivery device, the glucose monitoring device, the heart rate monitoring device, the glucagon delivery device, and the telecommunications device are in a common housing.

Embodiment 512. The system of embodiment 508, wherein the glucagon delivery device is configured to adjust an amount of glucagon that is administered to the subject based on the glucose level detected in the subject by the glucose monitoring device and the heart rate detected in the subject by the heart rate monitoring device.

Embodiment 513. The system of any one of embodiments 501-512, wherein the transmission from the telecommunications device to the insulin delivery device instructs the insulin delivery device to administer to the subject an adjusted dose of insulin over a period of at least 60 minutes.

Embodiment 514. The system of any one of embodiments 501-513, wherein the adjusted dose of insulin is about 15% of the basal dose of insulin.

Embodiment 515. The system of any one of embodiments 501-513, wherein the adjusted dose of insulin is about 50% of the basal dose of insulin.

Embodiment 516. The system of any one of embodiments 501-513, wherein the adjusted dose of insulin is about 85% of the basal dose of insulin.

Embodiment 517. The system of any one of embodiments 501-513, wherein the adjusted dose of insulin is about 90% of the basal dose of insulin.

Embodiment 518. The system of any one of embodiments 501-517, wherein the telecommunications device is in communication with a media device, wherein the telecommunications device instructs the media device to present to the subject an instructional exercise electronic communication medium based on the glucose level detected in the subject by the glucose monitoring device and the heart rate detected in the subject by the heart rate monitoring device.

Embodiment 519. The system of embodiment 518, wherein the electronic communication medium is a video.

Embodiment 520. The system of any one of embodiments 501-519, wherein the telecommunications device is configured to determine a level of the dose of insulin based on an input of an exercise to be performed by the subject, the reading of the glucose level in the subject by the glucose monitoring device, and the heart rate detected in the subject by the heart rate monitoring device.

Embodiment 521. The system of any one of embodiments 501-520, wherein any device or housing is implanted in the subject.

Embodiment 601. A system comprising: a) an insulin delivery device that is: 1) in contact with a subject; 2) configured to administer insulin to the subject; and 3) configured to receive a transmission of an instruction to administer to the subject a dose of insulin; and b) a glucose monitoring device that is: 1) in contact with the subject; 2) in communication with the insulin delivery device; 3) configured to detect a glucose level in the subject; and 4) configured to transmit to the insulin delivery device an instruction to administer to the subject the dose of insulin based on the detected glucose level in the subject, wherein the insulin delivery device comprises a processor and a computer-readable medium with a computer-executable code encoded thereon, wherein the computer-executable code instructs the insulin delivery device to administer to the subject an adjusted dose of insulin over a period of at least 30 minutes, wherein the adjusted dose of insulin is from about 5% to about 95% of a basal dose of insulin for the subject, and wherein the processor processes the computer-executable code.

Embodiment 602. The system of embodiment 601, wherein the insulin delivery device is configured to adjust an amount of insulin that is administered to the subject based on the glucose level detected in the subject by the glucose monitoring device.

Embodiment 603. The system of any one of embodiments 601-602, further comprising a glucagon delivery device that is: 1) in contact with the subject; 2) in communication with the insulin delivery device; 3) configured to administer glucagon to the subject; and 4) configured to receive from the insulin delivery device an instruction to administer to the subject a dose of glucagon.

Embodiment 604. The system of embodiment 603, wherein the insulin delivery device and the glucagon delivery device are in a common housing.

Embodiment 605. The system of any one of embodiments 603-604, wherein the glucagon delivery device is configured to adjust an amount of glucagon that is administered to the subject based on the glucose level detected in the subject by the glucose monitoring device.

Embodiment 606. The system of any one of embodiments 601-605, wherein the transmission instructs the insulin delivery device to administer to the subject an adjusted dose of insulin over a period of at least 60 minutes.

Embodiment 607. The system of any one of embodiments 601-606, wherein the adjusted dose of insulin is about 15% of the basal dose of insulin.

Embodiment 608. The system of any one of embodiments 601-606, wherein the adjusted dose of insulin is about 50% of the basal dose of insulin.

Embodiment 609. The system of any one of embodiments 601-606, wherein the adjusted dose of insulin is about 85% of the basal dose of insulin.

Embodiment 610. The system of any one of embodiments 601-606, wherein the adjusted dose of insulin is about 90% of the basal dose of insulin.

Embodiment 611. The system of any one of embodiments 601-610, further comprising a telecommunications device that is: 1) in communication with the insulin delivery device; 2) in communication with the glucose monitoring device; 3) configured to transmit to the insulin delivery device an instruction to administer to the subject the dose of insulin; and 4) configured to receive from the glucose monitoring device a transmission of a reading of the glucose level in the subject, wherein the insulin delivery device is configured to receive from the telecommunications device an instruction to administer to the subject the dose of insulin; and the glucose monitoring device is configured to transmit to the telecommunications device the reading of the glucose level in the subject.

Embodiment 612. The system of embodiment 611, wherein the telecommunications device is configured to display the glucose level detected in the subject by the glucose monitoring device.

Embodiment 613. The system of any one of embodiments 611-612, wherein the telecommunications device is in communication with a media device, wherein the telecommunications device instructs the media device to present to the subject an instructional exercise electronic communication medium based on the glucose level detected in the subject by the glucose monitoring device.

Embodiment 614. The system of embodiment 613, wherein the electronic communication medium is a video.

Embodiment 615. The system of any one of embodiments 601-614, wherein any device or housing is implanted in the subject.

Embodiment 701. A system comprising: a) an insulin delivery device that is: 1) in contact with a subject; 2) configured to administer insulin to the subject; and 3) configured to receive a transmission of an instruction to administer to the subject a dose of insulin; and b) a glucose monitoring device that is: 1) in contact with the subject; 2) in communication with the insulin delivery device; 3) configured to detect a glucose level in the subject; and 4) configured to transmit to the insulin delivery device an instruction to administer to the subject the dose of insulin based on the detected glucose level in the subject, wherein the glucose monitoring device sends a transmission from the glucose monitoring device to the insulin delivery device, wherein the transmission instructs the insulin delivery device to administer to the subject an adjusted dose of insulin over a period of at least 30 minutes, wherein the adjusted dose of insulin is from about 5% to about 95% of a basal dose of insulin for the subject.

Embodiment 702. The system of embodiment 701, wherein the insulin delivery device is configured to adjust an amount of insulin that is administered to the subject based on the glucose level detected in the subject by the glucose monitoring device.

Embodiment 703. The system of any one of embodiments 701-702, further comprising a glucagon delivery device that is: 1) in contact with the subject; 2) in communication with the glucose monitoring device; 3) configured to administer glucagon to the subject; and 4) configured to receive from the glucose monitoring device an instruction to administer to the subject a dose of glucagon.

Embodiment 704. The system of embodiment 703, wherein the insulin delivery device and the glucagon delivery device are in a common housing.

Embodiment 705. The system of any one of embodiments 703-704, wherein the glucagon delivery device is configured to adjust an amount of glucagon that is administered to the subject based on the glucose level detected in the subject by the glucose monitoring device.

Embodiment 706. The system of any one of embodiments 701-705, wherein the transmission instructs the insulin delivery device to administer to the subject an adjusted dose of insulin over a period of at least 60 minutes.

Embodiment 707. The system of any one of embodiments 701-706, wherein the adjusted dose of insulin is about 15% of the basal dose of insulin.

Embodiment 708. The system of any one of embodiments 701-706, wherein the adjusted dose of insulin is about 50% of the basal dose of insulin.

Embodiment 709. The system of any one of embodiments 701-706, wherein the adjusted dose of insulin is about 85% of the basal dose of insulin.

Embodiment 710. The system of any one of embodiments 701-706, wherein the adjusted dose of insulin is about 90% of the basal dose of insulin.

Embodiment 711. The system of any one of embodiments 701-710, further comprising a telecommunications device that is: 1) in communication with the insulin delivery device; 2) in communication with the glucose monitoring device; 3) configured to transmit to the insulin delivery device an instruction to administer to the subject the dose of insulin; and 4) configured to receive from the glucose monitoring device a transmission of a reading of the glucose level in the subject, wherein the insulin delivery device is configured to receive from the telecommunications device an instruction to administer to the subject the dose of insulin; and the glucose monitoring device is configured to transmit to the telecommunications device the reading of the glucose level in the subject.

Embodiment 712. The system of embodiment 711, wherein the telecommunications device is configured to display the glucose level detected in the subject by the glucose monitoring device.

Embodiment 713. The system of any one of embodiments 711-712, wherein the telecommunications device is in communication with a media device, wherein the telecommunications device instructs the media device to present to the subject an instructional exercise electronic communication medium based on the glucose level detected in the subject by the glucose monitoring device.

Embodiment 714. The system of embodiment 713, wherein the electronic communication medium is a video.

Embodiment 715. The system of any one of embodiments 701-714, wherein any device or housing is implanted in the subject.

Embodiment 801. A kit comprising: a) an insulin delivery device; and b) a glucose monitoring device, wherein the insulin delivery device comprises a processor and a computer-readable medium with a computer-executable code encoded thereon, wherein the computer-executable code instructs the insulin delivery device to administer to a subject an adjusted dose of insulin over a period of at least 30 minutes, wherein the adjusted dose of insulin is from about 5% to about 95% of a basal dose of insulin for the subject, and wherein the processor processes the computer-executable code.

Embodiment 802. The kit of embodiment 801, further comprising a glucagon delivery device.

Embodiment 803. The kit of embodiment 802, wherein the insulin delivery device and the glucagon delivery device are in a common housing.

Embodiment 804. The kit of any one of embodiments 801-803, wherein the computer-executable code instructs the insulin delivery device to administer to a subject the adjusted dose of insulin over a period of at least 60 minutes.

Embodiment 805. The kit of any one of embodiments 801-804, wherein the adjusted dose of insulin is about 15% of the basal dose of insulin.

Embodiment 806. The kit of any one of embodiments 801-804, wherein the adjusted dose of insulin is about 50% of the basal dose of insulin.

Embodiment 807. The kit of any one of embodiments 801-804, wherein the adjusted dose of insulin is about 85% of the basal dose of insulin.

Embodiment 808. The kit of any one of embodiments 801-804, wherein the adjusted dose of insulin is about 90% of the basal dose of insulin.

Embodiment 809. The kit of any one of embodiments 801-804, further comprising a telecommunications device.

Embodiment 810. The kit of embodiment 1, further comprising a heart rate monitor device.

Embodiment 901. A kit comprising: a) a telecommunications device; b) an insulin delivery device; and c) a glucose monitoring device, wherein the telecommunications device comprises a processor and a computer-readable medium with a computer-executable code encoded thereon, wherein the computer-executable code instructs the telecommunications device to transmit to the insulin delivery device an instruction to administer to a subject an adjusted dose of insulin over a period of at least 30 minutes, wherein the adjusted dose of insulin is from about 5% to about 95% of a basal dose of insulin for the subject, and wherein the processor processes the computer-executable code.

Embodiment 902. The kit of embodiment 901, further comprising a glucagon delivery device.

Embodiment 903. The kit of embodiment 902, wherein the insulin delivery device and the glucagon delivery device are in a common housing.

Embodiment 904. The kit of any one of embodiments 901-903, wherein the computer-executable code instructs the insulin delivery device to administer to a subject the adjusted dose of insulin over a period of at least 60 minutes.

Embodiment 905. The kit of any one of embodiments 901-904, wherein the adjusted dose of insulin is about 15% of the basal dose of insulin.

Embodiment 906. The kit of any one of embodiments 901-904, wherein the adjusted dose of insulin is about 50% of the basal dose of insulin.

Embodiment 907. The kit of any one of embodiments 901-904, wherein the adjusted dose of insulin is about 85% of the basal dose of insulin.

Embodiment 908. The kit of any one of embodiments 901-904, wherein the adjusted dose of insulin is about 90% of the basal dose of insulin.

Embodiment 909. The kit of any one of embodiments 901-908, further comprising a heart rate monitor device.

Embodiment 1001. A kit comprising: a) an insulin delivery device; and b) a glucose monitoring device, wherein the glucose monitoring device comprises a processor and a computer-readable medium with a computer-executable code encoded thereon, wherein the computer-executable code instructs the glucose monitoring device to transmit to the insulin delivery device an instruction to administer to a subject an adjusted dose of insulin over a period of at least 30 minutes, wherein the adjusted dose of insulin is from about 5% to about 95% of a basal dose of insulin for the subject, and wherein the processor processes the computer-executable code.

Embodiment 1002. The kit of embodiment 1001, further comprising a glucagon delivery device.

Embodiment 1003. The kit of embodiment 1002, wherein the insulin delivery device and the glucagon delivery device are in a common housing.

Embodiment 1004. The kit of any one of embodiments 1001-1003, wherein the computer-executable code instructs the insulin delivery device to administer to a subject the adjusted dose of insulin over a period of at least 60 minutes.

Embodiment 1005. The kit of any one of embodiments 1001-1004, wherein the adjusted dose of insulin is about 15% of the basal dose of insulin.

Embodiment 1006. The kit of any one of embodiments 1001-1004, wherein the adjusted dose of insulin is about 50% of the basal dose of insulin.

Embodiment 1007. The kit of any one of embodiments 1001-1004, wherein the adjusted dose of insulin is about 85% of the basal dose of insulin.

Embodiment 1008. The kit of any one of embodiments 1001-1004, wherein the adjusted dose of insulin is about 90% of the basal dose of insulin.

Embodiment 1009. The kit of any one of embodiments 1001-1008, further comprising a telecommunications device.

Embodiment 1010. The kit of any one of embodiments 1001-1009, further comprising a heart rate monitor device.

Embodiment 1101. A method comprising: a) presenting by a media device to a subject an electronic communication medium that provides instruction for physical exercise, wherein the subject is diabetic, wherein the media device is in communication with a receiver; b) monitoring, contemporaneously with presenting to the subject the electronic communication medium that provides instruction for physical exercise, via a glucose monitoring device the subject during a state of physical exercise, wherein the glucose monitoring device detects a blood glucose level in the subject; c) transmitting by a biometric device the blood glucose level of the subject to the receiver; d) receiving by the receiver the blood glucose level of the subject; and e) presenting by the media device an indication of a change in the blood glucose level of the subject in real time contemporaneously with presenting the electronic communication medium that provides instruction for physical exercise.

Embodiment 1102. The method of embodiment 1101, wherein the subject has type-1 diabetes.

Embodiment 1103. The method of embodiment 1101, wherein the subject has type-2 diabetes.

Embodiment 1104. The method of any one of embodiments 1101-1103, wherein the electronic communication medium is a video.

Embodiment 1105. The method of any one of embodiments 1101-1104, further comprising presenting to the subject by the electronic communication medium a warning that a biometric parameter of the subject has reached a value associated with a state of high risk.

Embodiment 1106. The method of any one of embodiments 1101-1105, wherein the receiver is in communication with a processor, wherein the processor determines based on the blood glucose level of the subject the suitability for the subject of an exercise instruction presented to the subject.

Embodiment 1107. The method of any one of embodiments 1101-1105, wherein the receiver is in communication with a processor, wherein the processor determines based on the blood glucose level of the subject that an exercise instruction being presented to the subject is unsuitable for the subject, and instructs the media device to display to the subject an alternative electronic communication medium that provides an alternative exercise instruction that is suitable for the subject based on the blood glucose level of the subject.

Embodiment 1108. The method of any one of embodiments 1101-1107, further comprising monitoring the subject's heart rate by a heart rate monitor, and presenting by the media device an indication of the subject's heart rate contemporaneously with presenting the electronic communication medium that provides instruction for physical exercise.

Embodiment 1109. The method of embodiment 1108, wherein the receiver is in communication with a processor, wherein the processor determines based on the subject's heart rate the suitability for the subject of an exercise instruction presented to the subject.

Embodiment 1110. The method of embodiment 1108, wherein the receiver is in communication with a processor, wherein the processor determines based on the subject's heart rate that an exercise instruction being presented to the subject is unsuitable for the subject, and instructs the media device to display to the subject an alternative electronic communication medium that provides an alternative exercise instruction that is suitable for the subject based on the subject's heart rate.

Embodiment 1111. The method of any one of embodiments 1101-1110, further comprising administering to the subject a dose of insulin based on the blood glucose level of the subject.

Embodiment 1112. The method of any one of embodiments 1101-1111, further comprising administering to the subject a dose of glucose based on the blood glucose level of the subject.

Embodiment 1113. The method of any one of embodiments 1101-1112, further comprising administering to the subject a dose of glucagon based on the blood glucose level of the subject.

Embodiment 1114. The method of any one of embodiments 1101-1113, further comprising receiving by the media device an input of a selection by the subject of an exercise to perform, wherein the presenting by the media device to the subject the electronic communication medium that provides the instruction for the physical exercise is based on the input of the selection by the subject.

Embodiment 1201. A system comprising: a media device configured to present: a) an instructional exercise electronic communication based on a biometric measurement detected in a subject by a biometric device; and b) an advertisement electronic communication based on the biometric measurement detected in the subject.

Embodiment 1202. The system of embodiment 1201, further comprising a processor configured to generate the advertisement electronic communication based on the biometric measurement detected in the subject, wherein the processor is in communication with the media device.

Embodiment 1203. The system of embodiment 1202, further comprising a receiver configured to receive the biometric measurement detected in the subject, wherein the receiver is in communication with the media device.

Embodiment 1204. The system of embodiment 1203, wherein the media device, the processor, and the receiver are in a common housing.

Embodiment 1205. The system of embodiment 1203, wherein the media device, the processor, the receiver, and the biometric device are in a common housing.

Embodiment 1206. The system of any one of embodiments 1201-1205, wherein the biometric device is: a) in contact with the subject; b) in communication with the media device; c) configured to detect the biometric measurement in the subject; and d) configured to transmit to the media device a reading of the biometric measurement detected in the subject.

Embodiment 1207. The system of any one of embodiments 1201-1206, wherein the biometric device is a glucose monitoring device and the biometric measurement detected in the subject is a blood glucose level.

Embodiment 1208. The system of any one of embodiments 1201-1206, wherein the biometric device is a heart rate monitoring device and the biometric measurement detected in the subject is a heart rate.

Embodiment 1209. The system of any one of embodiments 1201-1208, wherein the advertisement electronic communication is a clinical trial enrollment opportunity advertisement associated with the biometric measurement detected in the subject.

Embodiment 1301. A method comprising: a) presenting by a media device to a subject an instructional exercise electronic communication that provides instruction for physical exercise based on a biometric measurement detected in the subject by a biometric device; and b) presenting by the media device to the subject an advertisement electronic communication that provides an advertisement based on the biometric measurement detected in the subject.

Embodiment 1302. The method of embodiment 1301, further comprising detecting by the biometric device the biometric measurement in the subject, wherein the biometric device is in contact with the subject.

Embodiment 1303. The method of embodiment 1302, wherein the detecting of the biometric measurement in the subject is during a state of physical exercise.

Embodiment 1304. The method of any one of embodiments 1301-1303, further comprising receiving by a receiver from the biometric device a reading of the biometric measurement detected in the subject, wherein the receiver is in communication with the media device.

Embodiment 1305. The method of embodiment 1304, further comprising transmitting by the biometric device the reading of the biometric measurement detected in the subject to the receiver.

Embodiment 1306. The method of any one of embodiments 1301-1305, further comprising presenting, contemporaneously with presenting the instructional exercise electronic communication, by the media device to the subject an indication of a change in the biometric measurement detected in the subject in real-time by the biometric device.

Embodiment 1307. The method of any one of embodiments 1301-1306, wherein the biometric device is a glucose monitoring device and the biometric measurement detected in the subject is a blood glucose level.

Embodiment 1308. The method of any one of embodiments 1301-1306, wherein the biometric device is a heart rate monitoring device and the biometric measurement detected in the subject is a heart rate.

Embodiment 1309. The method of any one of embodiments 1301-1308, wherein the subject is diabetic.

Embodiment 1401. A computer program product comprising a non-transitory computer-readable medium having computer-executable code encoded therein, the computer-executable code adapted to be executed to implement a method of advertising to a subject, the method comprising: a) processing an advertisement system, wherein the advertisement system comprises: i) an instructional exercise communication module; ii) an advertisement communication module; and iii) an output module; b) generating by the instructional exercise communication module an instructional exercise communication based on a reading of a biometric measurement detected in the subject by a biometric device; c) generating by the advertisement communication module an advertisement based on the reading of the biometric measurement detected in the subject; d) communicating by the output module the instructional exercise communication to an output media device; and e) communicating by the output module the advertisement to the output media device.

Embodiment 1402. The computer program product of embodiment 1401, wherein the advertisement system further comprises a biometric data receiving module, and the method further comprises receiving by the biometric data receiving module the reading of the biometric measurement in the subject.

Embodiment 1403. The computer program product of embodiment 1401 or 1402, wherein the advertisement system further comprises a biometric detecting module, and the method further comprises detecting by the biometric detecting module the biometric measurement in the subject.

Embodiment 1404. The computer program product of any one of embodiments 1401-1403, wherein the communicating of the advertisement to the output media device is contemporaneous with the communicating of the instructional exercise electronic communication to the output media device.

Embodiment 1501. A method comprising: a) reviewing by a user from a media device an instructional exercise electronic communication; b) performing by the user an exercise suggested by the instructional exercise electronic communication; and c) receiving by the user from the media device an advertisement electronic communication that provides an advertisement based on a biometric measurement detected in the user by a biometric device.

Embodiment 1502. A method comprising: a) performing by a user an exercise; b) receiving by the user from a media device an instructional exercise electronic communication based on a biometric measurement detected in the user by a biometric device; and c) receiving by the user from the media device an advertisement electronic communication that provides an advertisement based on the biometric measurement detected in the user by the biometric device.

Embodiment 1503. The method of embodiment 1501 or 1502, wherein the advertisement is provided when the biometric measurement detected in the subject is determined to be unsafe.

Embodiment 1504. The method of any one of embodiments 1501-1503, wherein the biometric device is a glucose monitoring device and the biometric measurement detected in the subject is a blood glucose level.

Embodiment 1505. The method of any one of embodiments 1501-1503, wherein the biometric device is a heart rate monitoring device and the biometric measurement detected in the subject is a heart rate.

Embodiment 1506. The method of embodiment 1505, wherein the advertisement is provided when the heart rate detected in the subject is determined to be in a zone from 40% to 100% of a maximum heart rate in the user.

Embodiment 1507. The method of any one of embodiments 1501-1506, further comprising selecting by the user on the media device the received advertisement electronic communication.

Embodiment 1508. The method of any one of embodiments 1501-1507, further comprising purchasing by the user a product or a service described in the received advertisement.

Embodiment 1509. The method of any one of embodiments 1501-1508, wherein the advertisement is provided during the performing of the exercise by the user.

Embodiment 1510. The method of any one of embodiments 1501-1508, wherein the advertisement is provided before the performing of the exercise by the user.

Embodiment 1511. The method of any one of embodiments 1501-1508, wherein the advertisement is provided after the performing of the exercise by the user.

Embodiment 1512. The method of any one of embodiments 1501-1511, wherein the user is diabetic.

Embodiment 1601. A system comprising: a) a heart rate monitoring device configured to detect a heart rate in a subject; and b) a media device configured to present an advertisement electronic communication based on the heart rate detected in the subject by the heart rate monitoring device, wherein the heart rate monitoring device is configured to transmit to the media device a reading of the heart rate in the subject, wherein the media device is configured to present the advertisement electronic communication upon determination that the heart rate in the subject detected by the heart rate monitoring device is in a zone from 40% to 100% of a maximum heart rate in the subject.

Embodiment 1602. The system of embodiment 1601, further comprising a processor configured to generate the advertisement electronic communication based on the heart rate detected in the subject, wherein the processor is in communication with the media device.

Embodiment 1603. The system of embodiment 1602, further comprising a receiver configured to receive the heart rate detected in the subject, wherein the receiver is in communication with the media device.

Embodiment 1604. The system of embodiment 1603, wherein the media device, the processor, and the receiver are in a common housing.

Embodiment 1605. The system of embodiment 1603, wherein the media device, the processor, the receiver, and the heart rate monitoring device are in a common housing.

Embodiment 1606. The system of any one of embodiments 1601-1605, wherein the heart rate monitoring device is in contact with the subject.

Embodiment 1607. The system of any one of embodiments 1601-1606, wherein the advertisement electronic communication is a clinical trial enrollment opportunity advertisement associated with the heart rate detected in the subject.

Embodiment 1701. A method comprising presenting to a subject by a media device an advertisement electronic communication that provides an advertisement based on a heart rate detected in the subject by a heart rate monitoring device, wherein the subject is performing an exercise in a zone from 40% to 100% of a maximum heart rate in the subject.

Embodiment 1702. The method of embodiment 1701, further comprising detecting by the heart rate monitoring device the heart rate in the subject, wherein the heart rate monitoring device is in contact with the subject.

Embodiment 1703. The method of embodiment 1701 or 1702, wherein the detecting of the heart rate in the subject is during a state of physical exercise.

Embodiment 1704. The method of any one of embodiments 1701-1703, further comprising receiving by a receiver from the heart rate monitoring device a reading of the heart rate detected in the subject, wherein the receiver is in communication with the media device.

Embodiment 1705. The method of embodiment 1704, further comprising transmitting by the heart rate monitoring device the reading of the heart rate detected in the subject to the receiver.

Embodiment 1706. The method of any one of embodiments 1701-1705, further comprising presenting, contemporaneously with presenting the instructional exercise electronic communication, by the media device to the subject an indication of a change in the heart rate detected in the subject in real-time by the heart rate monitoring device.

Embodiment 1707. The method of any one of embodiments 1701-1706, wherein the subject is diabetic.

Embodiment 1801. A computer program product comprising a non-transitory computer-readable medium having computer-executable code encoded therein, the computer-executable code adapted to be executed to implement a method of advertising to a subject, the method comprising: a) processing an advertisement system, wherein the advertisement system comprises: i) a biometric data receiving module; ii) an advertisement communication module; and iii) an output module; b) receiving by the biometric data receiving module a reading of a heart rate detected in the subject by a heart rate monitoring device and determining that the heart rate detected in the subject is from 40% to 100% of a maximum heart rate in the subject; c) generating by the advertisement communication module an advertisement based on the reading of the heart rate detected in the subject; and d) communicating by the output module the advertisement to an output media device.

Embodiment 1802. The computer program product of embodiment 1801, wherein the advertisement system further comprises an instructional exercise communication module, and the method further comprises generating by the instructional exercise communication module an instructional exercise communication based on the reading of the heart rate detected in the subject.

Embodiment 1803. The computer program product of embodiment 1801 or 1802, wherein the method further comprises communicating by the output module the instructional exercise communication to the output media device.

Embodiment 1804. The computer program product of embodiment 1803, wherein the communicating of the advertisement to the output media device is contemporaneous with the communicating of the instructional exercise electronic communication to the output media device.

Embodiment 1805. The computer program product of any one of embodiments 1801-1804, wherein the advertisement system further comprises a heart rate detecting module, and the method further comprises detecting by the heart rate detecting module the heart rate in the subject.

Embodiment 1901. A method comprising: a) reviewing by a user from a media device an instructional exercise electronic communication; b) performing by the user an exercise suggested by the instructional exercise electronic communication; and c) receiving by the user from the media device an advertisement electronic communication that provides an advertisement upon determination that a heart rate in the user detected by a heart rate monitoring device is in a zone from 40% to 100% of a maximum heart rate in the user.

Embodiment 1902. The method of embodiment 1901, further comprising selecting by the user on the media device the received advertisement electronic communication.

Embodiment 1903. The method of embodiment 1901 or 1902, further comprising purchasing by the user a product or a service described in the received advertisement.

Embodiment 1904. The method of any one of embodiments 1901-1903, wherein the advertisement electronic communication is provided during the performing of the exercise by the user.

Embodiment 1905. The method of any one of embodiments 1901-1903, wherein the advertisement electronic communication is provided before the performing of the exercise by the user.

Embodiment 1906. The method of any one of embodiments 1901-1903, wherein the advertisement electronic communication is provided after the performing of the exercise by the user.

Embodiment 1907. The method of any one of embodiments 1901-1906, wherein the subject is diabetic.

Embodiment 2001. A system comprising: a media device configured to present: a) an instructional exercise electronic communication based on a biometric measurement detected in a subject by a biometric device; and b) a clinical trial electronic communication based on the biometric measurement detected in the subject.

Embodiment 2002. The system of embodiment 2001, further comprising a processor configured to determine eligibility of the subject in a clinical trial based on the biometric measurement detected in the subject, wherein the processor is in communication with the media device.

Embodiment 2003. The system of embodiment 2002, further comprising a receiver configured to receive the biometric measurement detected in a subject, wherein the receiver is in communication with the media device.

Embodiment 2004. The system of embodiment 2003, wherein the media device, the processor, and the receiver are in a common housing.

Embodiment 2005. The system of embodiment 2003, wherein the media device, the processor, the receiver, and the biometric device are in a common housing.

Embodiment 2006. The system of any one of embodiments 2001-2005, wherein the biometric device is: a) in contact with the subject; b) in communication with the media device; c) configured to detect the biometric measurement in the subject; and d) configured to transmit to the media device a reading of the biometric measurement detected in the subject.

Embodiment 2007. The system of any one of embodiments 2001-2006, wherein the biometric device is a glucose monitoring device and the biometric measurement detected in the subject is a blood glucose level.

Embodiment 2008. The system of any one of embodiments 2001-2006, wherein the biometric device is a heart rate monitoring device and the biometric measurement detected in the subject is a heart rate.

Embodiment 2101. A method comprising: a) presenting by a media device to a subject an instructional exercise electronic communication based on a biometric measurement detected in the subject by a biometric device; and b) determining eligibility of the subject in a clinical trial based on the biometric measurement detected in the subject.

Embodiment 2102. The method of embodiment 2101, further comprising detecting by the biometric device the biometric measurement in the subject, wherein the biometric device is in contact with the subject.

Embodiment 2103. The method of embodiment 2102, wherein the detecting of the biometric measurement in the subject is during a state of physical exercise.

Embodiment 2104. The method of any one of embodiments 2101-2103, further comprising receiving by a receiver from the biometric device a reading of the biometric measurement detected in the subject, wherein the receiver is in communication with the media device.

Embodiment 2105. The method of embodiment 2104, further comprising transmitting by the biometric device the reading of the biometric measurement detected in the subject to the receiver.

Embodiment 2106. The method of any one of embodiments 2101-2105, further comprising presenting, contemporaneously with presenting the instructional exercise electronic communication, by the media device to the subject an indication of a change in the biometric measurement detected in the subject in real-time by the biometric device.

Embodiment 2107. The method of any one of embodiments 2101-2106, wherein the biometric device is a glucose monitoring device and the biometric measurement detected in the subject is a blood glucose level.

Embodiment 2108. The method of any one of embodiments 2101-2106, wherein the biometric device is a heart rate monitoring device and the biometric measurement detected in the subject is a heart rate.

Embodiment 2109. The method of any one of embodiments 2101-2108, wherein the subject is diabetic.

Embodiment 2201. A computer program product comprising a non-transitory computer-readable medium having computer-executable code encoded therein, the computer-executable code adapted to be executed to implement a method of recruiting a subject in a clinical trial, the method comprising: a) processing a clinical trial recruitment system, wherein the clinical trial recruitment system comprises: i) an instructional exercise communication module; ii) an clinical trial communication module; and iii) an output module; b) generating by the instructional exercise communication module an instructional exercise communication based on a reading of a biometric measurement detected in the subject by a biometric device; c) generating by the clinical trial communication module a clinical trial electronic communication based on the reading of the biometric measurement in the subject; d) communicating by the output module the instructional exercise communication to an output media device; and e) communicating by the output module the clinical trial electronic communication to the output media device.

Embodiment 2202. The computer program product of embodiment 2201, wherein the clinical trial recruitment system further comprises a biometric data receiving module, and the method further comprises receiving by the biometric data receiving module the reading of the biometric measurement in the subject.

Embodiment 2203. The computer program product of embodiment 2201 or 2202, wherein the clinical trial recruitment system further comprises a biometric detecting module, and the method further comprises detecting by the biometric detecting module the biometric measurement in the subject.

Embodiment 2204. The computer program product of any one of embodiments 2201-2203, wherein the communicating of the clinical trial electronic communication to the output media device is contemporaneous with the communicating of the instructional exercise electronic communication to the output media device.

Embodiment 2301. A method comprising: a) receiving by the user from a media device an instructional exercise electronic communication; b) performing by the user an exercise provided by the instructional exercise electronic communication; and c) receiving by the user from the media device a clinical trial communication that provides a notification of a clinical trial based on a biometric measurement in the user by a biometric device.

Embodiment 2302. The method of embodiment 2301, wherein the biometric device is a glucose monitoring device and the biometric measurement detected in the user is a blood glucose level.

Embodiment 2303. The method of embodiment 2301, wherein the biometric device is a heart rate monitoring device and the biometric measurement detected in the user is a heart rate.

Embodiment 2304. The method of embodiment 2303, wherein the clinical trial communication is received when the heart rate detected in the user is determined to be in a zone from 40% to 100% of a maximum heart rate in the user.

Embodiment 2305. The method of any one of embodiments 2301-2304, further comprising selecting by the user the received notification of the clinical trial.

Embodiment 2306. The method of any one of embodiments 2301-2305, wherein the clinical trial communication is provided during the performing of the exercise by the user.

Embodiment 2307. The method of any one of embodiments 2301-2305, wherein the clinical trial communication is provided before the performing of the exercise by the user.

Embodiment 2308. The method of any one of embodiments 2301-2305, wherein the clinical trial communication is provided after the performing of the exercise by the user.

Embodiment 2309. The method of any one of embodiments 2301-2308, wherein the user is diabetic.

Embodiment 2401. A system comprising: a media device configured to present: a) an instructional exercise electronic communication based on a biometric measurement detected in a subject by a biometric device; and b) a non-exercise health recommendation to the subject based on the biometric measurement detected in the subject.

Embodiment 2402. The system of embodiment 2401, further comprising a processor configured to generate the non-exercise health recommendation based on the biometric measurement detected in the subject, wherein the processor is in communication with the media device.

Embodiment 2403. The system of embodiment 2402, further comprising a receiver configured to receive the biometric measurement detected in the subject, wherein the receiver is in communication with the media device.

Embodiment 2404. The system of embodiment 2403, wherein the media device, the processor, and the receiver are in a common housing.

Embodiment 2405. The system of embodiment 2403, wherein the media device, the processor, the receiver, and the biometric device are in a common housing.

Embodiment 2406. The system of any one of embodiments 2401-2405, wherein the biometric device is: a) in contact with the subject; b) in communication with the media device; c) configured to detect the biometric measurement in the subject; and d) configured to transmit to the media device a reading of the biometric measurement detected in the subject.

Embodiment 2407. The system of any one of embodiments 2401-2406, wherein the biometric device is a glucose monitoring device and the biometric measurement detected in the subject is a blood glucose level.

Embodiment 2408. The system of any one of embodiments 2401-2406, wherein the biometric device is a heart rate monitoring device and the biometric measurement detected in the subject is a heart rate.

Embodiment 2501. A method comprising: a) receiving by a user from a media device an instructional exercise electronic communication; b) performing by the user an exercise provided by the instructional exercise electronic communication; and c) receiving by the user from the media device a non-exercise health recommendation based on a biometric measurement detected in the user by a biometric device.

Embodiment 2502. The method of embodiment 2501, wherein the non-exercise health recommendation is received when the biometric measurement detected in the user is determined to be unsafe.

Embodiment 2503. The method of embodiment 2501 or 2502, wherein the biometric device is a glucose monitoring device and the biometric measurement detected in the user is a blood glucose level.

Embodiment 2504. The method of embodiment 2501 or 2502, wherein the biometric device is a heart rate monitoring device and the biometric measurement detected in the user is a heart rate.

Embodiment 2505. The method of embodiment 2504, wherein the non-exercise health recommendation is received when the heart rate detected in the user is determined to be in a zone from 40% to 100% of a maximum heart rate in the user.

Embodiment 2506. The method of any one of embodiments 2501-2504, wherein the non-exercise health recommendation is received during the performing of the exercise by the user.

Embodiment 2507. The method of any one of embodiments 2501-2504, wherein the non-exercise health recommendation is received before the performing of the exercise by the user.

Embodiment 2508. The method of any one of embodiments 2501-2504, wherein the non-exercise health recommendation is received after the performing of the exercise by the user.

Embodiment 2509. The method of any one of embodiments 2501-2504, wherein the user is diabetic.

What is claimed is:

1. A method comprising:
    a) presenting by a media device to a user an instructional exercise electronic communication that provides instruction for physical exercise based on a biometric measurement detected in the user by a biometric device; and
    b) automatically presenting by the media device to the user an advertisement electronic communication that provides an advertisement based on the biometric measurement detected in the user.

2. The method of claim 1, further comprising detecting by the biometric device the biometric measurement in the user.

3. The method of claim 2, wherein the detecting of the biometric measurement in the user is during a state of physical exercise.

4. The method of claim 2, wherein the biometric device is in contact with the user.

5. The method of claim 1, further comprising receiving by a receiver from the biometric device a reading of the biometric measurement detected in the user, wherein the receiver is in communication with the media device.

6. The method of claim 1, further comprising transmitting by the biometric device a reading of the biometric measurement detected in the user to a receiver.

7. The method of claim 1, further comprising presenting, contemporaneously with presenting the instructional exercise electronic communication, by the media device to the user an indication of a change in the biometric measurement detected in the user in real-time by the biometric device.

8. The method of claim 1, wherein the biometric device is a glucose monitoring device and the biometric measurement detected in the user is a blood glucose level.

9. The method of claim 1, wherein the biometric device is a heart rate monitoring device and the biometric measurement detected in the user is a heart rate.

10. The method of claim 9, wherein the media device presents the advertisement electronic communication to the user when the heart rate detected in the user is determined to be in a zone from 40% to 100% of a maximum heart rate in the user.

11. The method of claim 1, wherein the user is diabetic.

12. A computer program product comprising a non-transitory computer-readable medium having computer-executable code encoded therein, the computer-executable code adapted to be executed to implement a method of advertising to a user, the method comprising:
 a) processing an advertisement system, wherein the advertisement system comprises:
  i) an instructional exercise communication module;
  ii) an advertisement communication module; and
  iii) an output module;
 b) generating by the instructional exercise communication module an instructional exercise communication based on a reading of a biometric measurement detected in the user by a biometric device;
 c) automatically generating by the advertisement communication module an advertisement based on the reading of the biometric measurement detected in the user;
 d) communicating by the output module the instructional exercise communication to an output media device; and
 e) communicating by the output module the advertisement to the output media device.

13. The computer program product of claim 12, wherein the advertisement system further comprises a biometric data receiving module, and the method further comprises receiving by the biometric data receiving module the reading of the biometric measurement in the user.

14. The computer program product of claim 12, wherein the advertisement system further comprises a biometric detecting module, and the method further comprises detecting by the biometric detecting module the biometric measurement in the user.

15. The computer program product of claim 14, wherein the detecting of the biometric measurement in the user is during a state of physical exercise.

16. The computer program product of claim 12, wherein the communicating of the advertisement to the output media device is contemporaneous with the communicating of the instructional exercise electronic communication to the output media device.

17. The computer program product of claim 12, wherein the method further comprises communicating, contemporaneously with communicating the instructional exercise electronic communication, by the output media device to the user an indication of a change in the biometric measurement detected in the user in real-time by the biometric device.

18. The computer program product of claim 12, wherein the biometric device is a glucose monitoring device and the biometric measurement detected in the user is a blood glucose level.

19. The computer program product of claim 12, wherein the biometric device is a heart rate monitoring device and the biometric measurement detected in the user is a heart rate.

20. The computer program product of claim 19, wherein the output module communicates the advertisement to the output media device when the heart rate detected in the user is determined to be in a zone from 40% to 100% of a maximum heart rate in the user.

21. The computer program product of claim 12, wherein the advertisement system is coded for use with a diabetic user.

* * * * *